(12) United States Patent
Zinzalla et al.

(10) Patent No.: US 11,578,129 B2
(45) Date of Patent: Feb. 14, 2023

(54) LRP5 AND PD-1 ANTAGONIST ANTICANCER COMBINATION THERAPY

(71) Applicant: Boehringer Ingelheim International GmbH, Ingelheim am Rhein (DE)

(72) Inventors: Vittoria Zinzalla, Vienna (AT); Markus Johann Bauer, Vienna (AT); Barbara Drobits-Handl, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 173 days.

(21) Appl. No.: 16/830,322

(22) Filed: Mar. 26, 2020

(65) Prior Publication Data

US 2020/0308283 A1    Oct. 1, 2020

(30) Foreign Application Priority Data

Mar. 29, 2019   (EP) .................................... 19166372

(51) Int. Cl.
| | | |
|---|---|---|
| *A61K 39/395* | (2006.01) | |
| *C07K 16/28* | (2006.01) | |
| *A61P 35/00* | (2006.01) | |
| *C07K 16/30* | (2006.01) | |
| *A61K 39/00* | (2006.01) | |

(52) U.S. Cl.
CPC .. *C07K 16/2818* (2013.01); *A61K 39/001129* (2018.08); *A61P 35/00* (2018.01); *C07K 16/28* (2013.01); *C07K 16/30* (2013.01); *A61K 2039/505* (2013.01); *A61K 2039/545* (2013.01); *C07K 2317/51* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 2012/0276089 A1 | 11/2012 | Lee | |
| 2017/0334995 A1* | 11/2017 | Zettl | ........................ A61P 43/00 |
| 2018/0344868 A1* | 12/2018 | Zinzalla | ................. C07K 16/28 |

FOREIGN PATENT DOCUMENTS

| | | |
|---|---|---|
| WO | 2011119661 | 9/2011 |
| WO | 2011138391 | 11/2011 |
| WO | 2011138392 A1 | 11/2011 |
| WO | 2017093478 | 1/2018 |
| WO | 2018220080 | 6/2018 |
| WO | 2016004055 | 7/2018 |
| WO | WO-2018174984 A1 * | 9/2018 ......... A61K 39/3955 |

OTHER PUBLICATIONS

International Search Report and Written Opinion, for PCT.EP2020/058515, dated Jun. 26, 2020.
International Search Report for PCT/EP2020/05853 dated Jun. 26,2020.

(Continued)

*Primary Examiner* — Claire Kaufman
(74) *Attorney, Agent, or Firm* — Wendy M. Gombert

(57) ABSTRACT

The invention describes anti-cancer therapies comprising using an LRP5 antagonist in combination with an anti-PD1 antibody, each as described herein.

11 Claims, 1 Drawing Sheet
Specification includes a Sequence Listing.

A.

B.

(56) References Cited

OTHER PUBLICATIONS

Xiao, DKK2 imparts tumor immunity evasion through beta-catenin independent suppression of cytotoxic immune cell activation, Nature Medicine, vol. 24, 2018.

Anonymous, an open label, Phase I trial to detrmine the Maximum tolerated dose and investigate safety, pharmacokinetics and Efficacy of BI 905677 Administered Intravenously in Patients, retrieved from Internet, https://clinicaltrials.gov/ct2/history/NCT03604445?V12 retrieved Jun. 4, 2020, 2019.

Fenderico, Anti-LRP5/6 VHHs promote differentiation of Wnt-hypersensitive intestinal stem cells, Nature Communications, vol. 10, 2019.

Bas, a holistic Evalustion of Articles on PD-1 and PD-L1 Published between 1975 and 2017, Cancer INformatics, vol. 18, 2019, 8 pages.

Ren, LRP5 and LRP6 in Wnt signaling, Frontiers in Cell and Developmental Biology, vol. 9, 2021, 11 pages.

Stancovski, Mechanistic aspects of the opposing effects of monoclonal antibodies to the ERBB2 receptor on tumor growth, Proc. Natl. Acad Sci, vol. 88, 1991, 5 pages.

Topalian, Safety, Activity, and Immune Correlates of Anit-PD-1 Antibody in Cancer, The N.E. Journal of Medicine, vol. 366, 2012, 12 pages.

\* cited by examiner

Fig. 1A-H
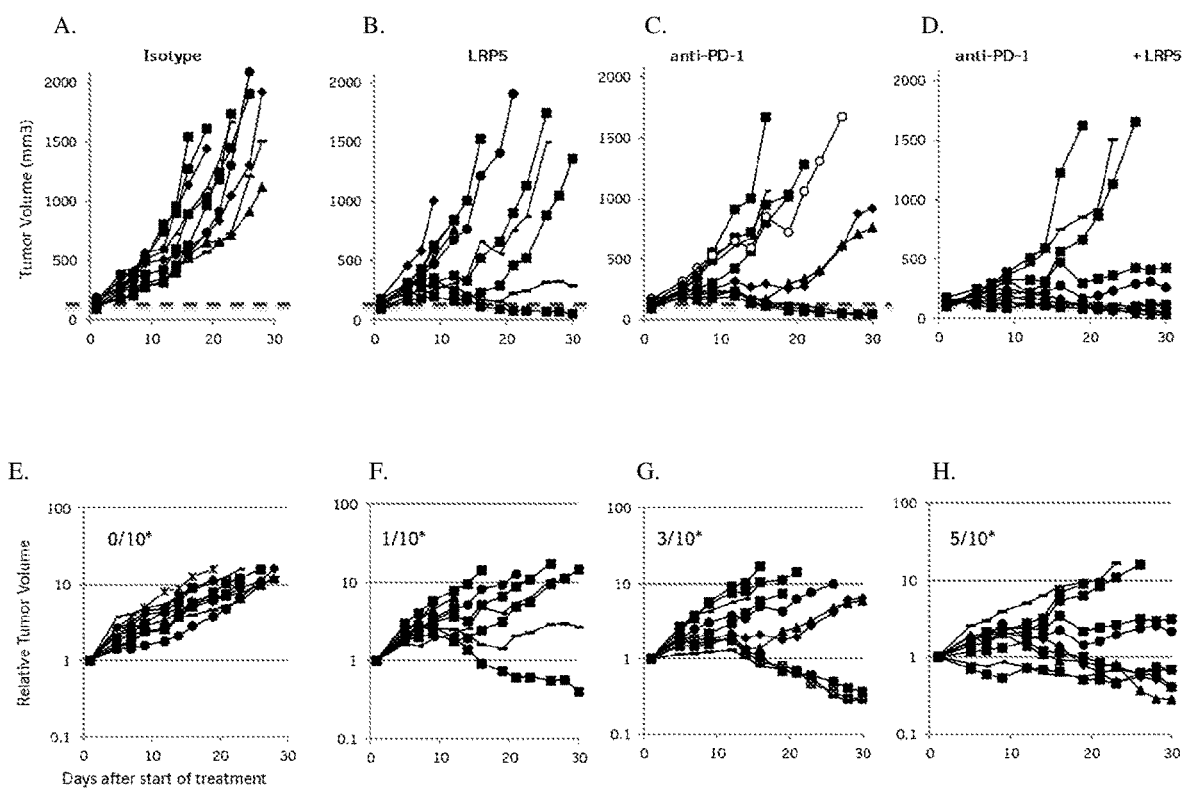
*Responses at the end of the study = tumor shrinkage (Tumor volume end/Tumor volume start <1)

LRP5 AND PD-1 ANTAGONIST ANTICANCER COMBINATION THERAPY

This application contains a sequence listing in accordance with 37 C.F.R. 1.821-1.825. The content of the ASCII text file of the sequence listing named 120438SequenceListing.txt which is 64,617 bytes in size was created on Mar. 27, 2020, and electronically submitted via EFS-Web herewith the application is incorporated herein by reference in its entirety.

FIELD OF THE INVENTION

The present invention relates to a combination therapy in the treatment of cancer and to compounds for use in such a combination therapy. The compounds for combination are an LRP5 antagonist and a PD-1 antagonist.

BACKGROUND OF THE INVENTION

Activation of the Wnt signaling pathway requires binding of extracellular Wnt ligands to the Frizzled receptor and to the co-receptor LRP5 (Accession number: UniProtKB-O75197/LRP5_HUMAN) or its closely related homologue LRP6 (Accession number: UniProtKB—O75581/LRP6_HUMAN). There are 19 Wnt proteins and 10 Frizzled receptors in mammalian cells. In the absence of Wnt ligand, cytoplasmic beta-catenin is phosphorylated by a protein complex consisting of the scaffolding proteins Axin and APC and the kinases GSK3beta and CK1a. Subsequent recognition by the ubiquitin ligase beta-TrcP leads to ubiquitin-mediated degradation of beta-catenin. In the presence of Wnt ligand, binding of Wnt to Frizzled and LRP5 leads to recruitment of the cytoplasmic effector protein Dvl and phosphorylation of the LRP5 cytoplasmic tail, which provides the docking site for Axin. Axin sequestration by LRP5 leads to the inactivation of the Axin-APC-GSK3beta complex and, therefore, intracellular beta-catenin stabilization and accumulation. Hence, cytoplasmic levels of beta-catenin rise, and beta-catenin migrates to the nucleus and complexes with members of the T-cell factor (TCF)/Lymphoid enhancer-binding factor (LEF) family of transcription factors. Basal transcription machinery and transcriptional co-activators are then recruited, including cAMP response element-binding protein (CREB)-binding protein (CBP) or its homolog p300, leading to expression of various target genes, including Axin2, cyclin D1, Naked1, Notum and c-Myc.

An additional level of ligand-dependent Wnt pathway regulation is mediated by the E3 ligase RNF43, and its closely related homologue ZNRF3, and by the secreted R-Spondin proteins (de Lau et al. "The R-spondin/Lgr5/Rnf43 module: regulator of Wnt signal strength". *Genes Dev.* 2014; 28(4):305-16). RNF43 mediates the ubiquitination of the Frizzled/LRP5 receptor complex at the cell surface, leading to its degradation and, thereby, inhibiting ligand-dependent Wnt pathway activity. The activity of RNF43 is counteracted by the R spondin family members (R-spondin 1 to 4 ligands). When R-Spondin ligand is present, it removes RNF43 from the cell surface, allowing Frizzled/LRP5 complex accumulation and enhancement of Wnt signaling in the presence of Wnt ligands.

Hyperactivation of Wnt signaling is involved in the pathogenesis of various, albeit not all, types of cancer in at least two different ways: in some cancer types frequent mutations in downstream signaling molecules contribute to constitutively activated Wnt pathway (e.g. APC mutations in colorectal cancer; beta-catenin activating mutation in hepatocellular carcinoma), while in other types of cancer, such as e.g. Triple Negative Breast Cancer (TNBC), Non Small Cell Lung Cancer (NSCLC), pancreatic adenocarcinoma and in a subset of Colo-Rectal Cancer (CRC) and endometrial cancers, Wnt signaling activation is driven by a ligand dependent mechanism (i.e. by an autocrine/paracrine Wnt activation), as detected by beta-catenin intracellular accumulation. In NSCLC, TNBC and pancreatic adenocarcinoma, ligand dependent Wnt activation is mediated by multiple mechanisms, including increased expression of the Wnt ligands and/or of LRP5 receptors, or silencing of LRP5 negative regulator DKK1 (TNBC: Khramtsov et al. "Wnt/beta-catenin pathway activation is enriched in basal-like breast cancers and predicts poor outcome". *Am J Pathol.* 2010; 176(6): 2911-20; NSCLC: Nakashima et al. "Wnt1 overexpression associated with tumor proliferation and a poor prognosis in non-small cell lung cancer patients". *Oncol Rep.* 2008; 19(1):203-9; Pancreatic cancer: Zhang et al. "Canonical wnt signaling is required for pancreatic carcinogenesis". *Cancer Res.* 2013; 73(15):4909-22). In particular, published data have shown that in healthy tissues (e.g. mammary and lung epithelium), beta-catenin is localized solely at the plasma membrane. In contrast, the majority of TNBC, NSCLC and pancreatic adenocarcinoma primary clinical samples showed beta-catenin intracellular accumulation (i.e. in the cytoplasm/nucleus; biomarker of Wnt signaling activation), due to aberrant Wnt signaling.

Because LRP5 functions as gatekeeper of ligand dependent Wnt signaling activation, it may be considered as target to achieve complete blockade of the pathway mediated by all 19 Wnt ligands and 10 Frizzled receptors.

An alternative method to the above described approach of directly targeting the cancer/cancer cells is cancer immunotherapy. Cancer immunotherapy is a branch of oncology in which the immune system is used to treat cancer, which is in stark contrast to existing common methods of treatment in which the tumour is directly excised or treated. This therapeutic concept is based on the identification of a number of proteins on the surface of T-cells which act to inhibit the immune function of these cells. Listed among these proteins is PD-1 (Programmed cell Death 1).

PD-1 is a cell surface receptor protein expressed on T-cells. PD-1 has two ligands, PD-L1 and PD-L2, which interact with the cell surface receptor. On ligand-binding, PD-1 induces an intracellular signal which negatively regulates T-cell response. Thus, typically, the protein functions as an "immune checkpoint" inhibitor, i.e. it acts to modulate the activity of cells in the immune system so as to regulate and limit autoimmune diseases. It has been recently understood that many cancers can protect themselves from the immune system by modifying "immune checkpoint" inhibitors and thus avoid detection.

Accordingly, it has also been shown in a range of different cancer settings that antagonistic PD-1 antibody molecules, such as e.g. nivolumab and pembrolizumab, can be used to stimulate the immune system and thereby treat cancer.

Despite the above described advances in the treatment of cancer, there is still a need for new therapeutic concepts for the treatment of cancer which show advantages over standard therapies. These advantages may include in vivo efficacy (e.g. improved clinical response, extend of the response, increase of the rate of response, duration of response, disease stabilization rate, duration of stabilization, time to disease progression, progression free survival (PFS) and/or overall survival (OS), later occurrence of resistance and the like), safe and well tolerated administration and reduced frequency and severity of adverse events. Specifically, there is a need for additional treatment options for patients with cancers like, e.g., lung cancer (e.g. NSCLC), melanoma, bladder and gastrointestinal cancers.

It is thus an object of the present invention to provide a novel treatment for cancer that is advantageous over treatments/methods of treatment currently used and/or known in the prior art.

BRIEF SUMMARY OF THE INVENTION

The present invention provides a method for treating a patient with a hyperproliferative disease with an LRP5 antagonist (this term is used interchangeably herein with the terms "polypeptide specifically binding to LRP5" or "polypeptide capable of specifically binding to LRP5"), together with an antibody specific for Programmed Cell Death 1 (PD-1) (this term is used interchangeably herein with the terms "anti PD-1 antibody", "PD-1 antibody" or "PD-1 antagonist"), thereby antagonizing the PD-1 signaling pathway. Accordingly, the present invention provides a combination therapy comprising an LRP5 antagonist and an anti-PD-1 antibody.

In one aspect, the invention provides an LRP5 antagonist for use in a method of treating and/or preventing a hyperproliferative disease, preferably cancer, the method comprising that the LRP5 antagonist is to be administered in combination with a PD-1 antibody to a patient in need thereof, the LRP5 antagonist being selected from the group consisting of (i) a polypeptide comprising a first immunoglobulin single variable domain (ISVD)
   (a) comprising the following CDR sequences:

```
                                    (SEQ ID NO: 40)
   CDR1: TYVMG (SEQ ID NO: 41)
   CDR2: AISWSGGSTYYADSVKG (SEQ ID NO: 42)
   CDR3: SRGTSTPSRASGVSRYDY,
``` and
   a second ISVD (b) comprising the following CDR sequences:

```
                                    (SEQ ID NO: 46)
   CDR1: IGAMG (SEQ ID NO: 47)
   CDR2: AVSSGGSTYYVDSVKG (SEQ ID NO: 48)
   CDR3: ETGPYGPPKRDY;
```

(ii) a polypeptide comprising a first ISVD (a) comprising the following CDR sequences:

```
                                    (SEQ ID NO: 40)
   CDR1: TYVMG (SEQ ID NO: 41)
   CDR2: AISWSGGSTYYADSVKG (SEQ ID NO: 42)
   CDR3: SRGTSTPSRASGVSRYDY,
``` and
   a second ISVD (b) comprising the following CDR sequences:

```
                                    (SEQ ID NO: 49)
   CDR1: INAMG (SEQ ID NO: 47)
   CDR2: AVSSGGSTYYVDSVKG (SEQ ID NO: 48)
   CDR3: ETGPYGPPKRDY;
```

(iii) a polypeptide comprising a first ISVD (a) comprising the following CDR sequences:

```
                                    (SEQ ID NO: 43)
   CDR1: RYAVA (SEQ ID NO: 44)
   CDR2: AITWSSGRIDYADSVKG (SEQ ID NO: 45)
   CDR3: DRRPRSTGRSGTGSPSTYDY,
``` and
   a second ISVD (b) comprising the following CDR sequences:

```
                                    (SEQ ID NO: 46)
   CDR1: IGAMG (SEQ ID NO: 47)
   CDR2: AVSSGGSTYYVDSVKG (SEQ ID NO: 48)
   CDR3: ETGPYGPPKRDY;
``` and
(iv) a polypeptide comprising a first ISVD (a) comprising the following CDR sequences:

```
                                    (SEQ ID NO: 43)
   CDR1: RYAVA (SEQ ID NO: 44)
   CDR2: AITWSSGRIDYADSVKG (SEQ ID NO: 45)
   CDR3: DRRPRSTGRSGTGSPSTYDY,
``` and
   a second ISVD (b) comprising the following CDR sequences:

```
                                    (SEQ ID NO: 49)
   CDR1: INAMG (SEQ ID NO: 47)
   CDR2: AVSSGGSTYYVDSVKG (SEQ ID NO: 48)
   CDR3: ETGPYGPPKRDY;
``` and the PD-1 antibody being selected from the group consisting of
(i) an anti-PD1 antibody comprising heavy chain CDRs comprising the amino acid sequence of SEQ ID NO:1

(HCDR1), SEQ ID NO:2 (HCDR2) and SEQ ID NO:3 (HCDR3) and light chain CDRs comprising the amino acid sequence of SEQ ID NO:4 (LCDR1), SEQ ID NO:5 (LCDR2) and SEQ ID NO:6 (LCDR3);
(ii) an anti-PD1 antibody comprising heavy chain CDRs comprising the amino acid sequence of SEQ ID NO:7 (HCDR1), SEQ ID NO:8 (HCDR2) and SEQ ID NO:9 (HCDR3) and light chain CDRs comprising the amino acid sequence of SEQ ID NO:10 (LCDR1), SEQ ID NO:11 (LCDR2) and SEQ ID NO:12 (LCDR3); and
(iii) an anti-PD1 antibody comprising heavy chain CDRs comprising the amino acid sequence of SEQ ID NO:13 (HCDR1), SEQ ID NO:14 (HCDR2) and SEQ ID NO:15 (HCDR3) and light chain CDRs comprising the amino acid sequence of SEQ ID NO:16 (LCDR1), SEQ ID NO:17 (LCDR2) and SEQ ID NO:18 (LCDR3).

In another aspect, the invention provides a method of treating and/or preventing a hyperproliferative disease, preferably cancer, comprising administering to a patient in need thereof a therapeutically effective amount of an LRP5 antagonist and a therapeutically effective amount of a PD-1 antibody,
the LRP5 antagonist being selected from the group consisting of
(i) a polypeptide comprising a first immunoglobulin single variable domain (ISVD) (a) comprising the following CDR sequences:

```
CDR1: TYVMG                             (SEQ ID NO: 40)

CDR2: AISWSGGSTYYADSVKG                 (SEQ ID NO: 41)

CDR3: SRGTSTPSRASGVSRYDY,               (SEQ ID NO: 42)
``` and
a second ISVD (b) comprising the following CDR sequences:

```
CDR1: IGAMG                             (SEQ ID NO: 46)

CDR2: AVSSGGSTYYVDSVKG                  (SEQ ID NO: 47)

CDR3: ETGPYGPPKRDY;                     (SEQ ID NO: 48)
```

(ii) a polypeptide comprising a first ISVD (a) comprising the following CDR sequences:

```
CDR1: TYVMG                             (SEQ ID NO: 40)

CDR2: AISWSGGSTYYADSVKG                 (SEQ ID NO: 41)

CDR3: SRGTSTPSRASGVSRYDY,               (SEQ ID NO: 42)
``` and
a second ISVD (b) comprising the following CDR sequences:

```
CDR1: INAMG                             (SEQ ID NO: 49)

CDR2: AVSSGGSTYYVDSVKG                  (SEQ ID NO: 47)

CDR3: ETGPYGPPKRDY;                     (SEQ ID NO: 48)
```

(iii) a polypeptide comprising a first ISVD (a) comprising the following CDR sequences:

```
CDR1: RYAVA                             (SEQ ID NO: 43)

CDR2: AITWSSGRIDYADSVKG                 (SEQ ID NO: 44)

CDR3: DRRPRSTGRSGTGSPSTYDY,             (SEQ ID NO: 45)
``` and
a second ISVD (b) comprising the following CDR sequences:

```
CDR1: IGAMG                             (SEQ ID NO: 46)

CDR2: AVSSGGSTYYVDSVKG                  (SEQ ID NO: 47)

CDR3: ETGPYGPPKRDY;                     (SEQ ID NO: 48)
``` and
(iv) a polypeptide comprising a first ISVD (a) comprising the following CDR sequences:

```
CDR1: RYAVA                             (SEQ ID NO: 43)

CDR2: AITWSSGRIDYADSVKG                 (SEQ ID NO: 44)

CDR3: DRRPRSTGRSGTGSPSTYDY,             (SEQ ID NO: 45)
``` and
a second ISVD (b) comprising the following CDR sequences:

```
CDR1: INAMG                             (SEQ ID NO: 49)

CDR2: AVSSGGSTYYVDSVKG                  (SEQ ID NO: 47)

CDR3: ETGPYGPPKRDY;                     (SEQ ID NO: 48)
``` and the PD-1 antibody being selected from the group consisting of
(i) an anti-PD1 antibody comprising heavy chain CDRs comprising the amino acid sequence of SEQ ID NO:1 (HCDR1), SEQ ID NO:2 (HCDR2) and SEQ ID NO:3 (HCDR3) and light chain CDRs comprising the amino acid sequence of SEQ ID NO:4 (LCDR1), SEQ ID NO:5 (LCDR2) and SEQ ID NO:6 (LCDR3);
(ii) an anti-PD1 antibody comprising heavy chain CDRs comprising the amino acid sequence of SEQ ID NO:7 (HCDR1), SEQ ID NO:8 (HCDR2) and SEQ ID NO:9 (HCDR3) and light chain CDRs comprising the amino acid sequence of SEQ ID NO:10 (LCDR1), SEQ ID NO:11 (LCDR2) and SEQ ID NO:12 (LCDR3); and (iii) an anti-PD1 antibody comprising heavy chain CDRs comprising the amino acid sequence of SEQ ID NO:13 (HCDR1), SEQ ID NO:14 (HCDR2) and SEQ ID NO:15 (HCDR3) and light chain CDRs comprising the amino acid sequence of SEQ ID NO:16 (LCDR1), SEQ ID NO:17 (LCDR2) and SEQ ID NO:18 (LCDR3).

In another aspect, the invention provides a PD-1 antibody for use in a method of treating and/or preventing a hyperproliferative disease, preferably cancer, the method comprising that a PD-1 antibody is to be administered in combination with a LRP5 antagonist to a patient in need thereof, the LRP5 antagonist being selected from the group consisting of (i) a polypeptide comprising a first immunoglobulin single variable domain (ISVD)
(a) comprising the following CDR sequences:

```
                                   (SEQ ID NO: 40)
CDR1: TYVMG (SEQ ID NO: 41)
CDR2: AISWSGGSTYYADSVKG (SEQ ID NO: 42)
CDR3: SRGTSTPSRASGVSRYDY,
``` and
a second ISVD (b) comprising the following CDR sequences:

```
                                   (SEQ ID NO: 46)
CDR1: IGAMG (SEQ ID NO: 47)
CDR2: AVSSGGSTYYVDSVKG (SEQ ID NO: 48)
CDR3: ETGPYGPPKRDY;
```

(ii) a polypeptide comprising a first ISVD (a) comprising the following CDR sequences:

```
                                   (SEQ ID NO: 40)
CDR1: TYVMG (SEQ ID NO: 41)
CDR2: AISWSGGSTYYADSVKG (SEQ ID NO: 42)
CDR3: SRGTSTPSRASGVSRYDY,
``` and
a second ISVD (b) comprising the following CDR sequences:

```
                                   (SEQ ID NO: 49)
CDR1: INAMG (SEQ ID NO: 47)
CDR2: AVSSGGSTYYVDSVKG (SEQ ID NO: 48)
CDR3: ETGPYGPPKRDY;
```

(iii) a polypeptide comprising a first ISVD (a) comprising the following CDR sequences:

```
                                   (SEQ ID NO: 43)
CDR1: RYAVA (SEQ ID NO: 44)
CDR2: AITWSSGRIDYADSVKG (SEQ ID NO: 45)
CDR3: DRRPRSTGRSGTGSPSTYDY,
``` and
a second ISVD (b) comprising the following CDR sequences:

```
                                   (SEQ ID NO: 46)
CDR1: IGAMG (SEQ ID NO: 47)
CDR2: AVSSGGSTYYVDSVKG (SEQ ID NO: 48)
CDR3: ETGPYGPPKRDY;
``` and
(iv) a polypeptide comprising a first ISVD (a) comprising the following CDR sequences:

```
                                   (SEQ ID NO: 43)
CDR1: RYAVA (SEQ ID NO: 44)
CDR2: AITWSSGRIDYADSVKG (SEQ ID NO: 45)
CDR3: DRRPRSTGRSGTGSPSTYDY,
``` and
a second ISVD (b) comprising the following CDR sequences:

```
                                   (SEQ ID NO: 49)
CDR1: INAMG (SEQ ID NO: 47)
CDR2: AVSSGGSTYYVDSVKG (SEQ ID NO: 48)
CDR3: ETGPYGPPKRDY;
``` and
and the PD-1 antibody being selected from the group consisting of (i) an anti-PD1 antibody comprising heavy chain CDRs comprising the amino acid sequence of SEQ ID NO:1 (HCDR1), SEQ ID NO:2 (HCDR2) and SEQ ID NO:3 (HCDR3) and light chain CDRs comprising the amino acid sequence of SEQ ID NO:4 (LCDR1), SEQ ID NO:5 (LCDR2) and SEQ ID NO:6 (LCDR3);

(ii) an anti-PD1 antibody comprising heavy chain CDRs comprising the amino acid sequence of SEQ ID NO:7 (HCDR1), SEQ ID NO:8 (HCDR2) and SEQ ID NO:9 (HCDR3) and light chain CDRs comprising the amino acid sequence of SEQ ID NO:10 (LCDR1), SEQ ID NO:11 (LCDR2) and SEQ ID NO:12 (LCDR3); and (iii) an anti-PD1 antibody comprising heavy chain CDRs comprising the amino acid sequence of SEQ ID NO:13 (HCDR1), SEQ ID NO:14 (HCDR2) and SEQ ID NO:15 (HCDR3) and light chain CDRs comprising the amino acid sequence of SEQ ID NO:16 (LCDR1), SEQ ID NO:17 (LCDR2) and SEQ ID NO:18 (LCDR3).

In another aspect, the invention provides for the use of an LRP5 antagonist for preparing a pharmaceutical composition for use in a method of treating and/or preventing a hyperproliferative disease, preferably cancer, wherein the LRP5-antagonist is to be used in combination with a PD-1 antibody, wherein the LRP5 antagonist is selected from the group consisting of (i) a polypeptide comprising a first immunoglobulin single variable domain (ISVD)

(a) comprising the following CDR sequences:

```
                                           (SEQ ID NO: 40)
    CDR1: TYVMG
                                           (SEQ ID NO: 41)
    CDR2: AISWSGGSTYYADSVKG
                                           (SEQ ID NO: 42)
    CDR3: SRGTSTPSRASGVSRYDY,
``` and a second ISVD (b) comprising the following CDR sequences:

```
                                           (SEQ ID NO: 46)
    CDR1: IGAMG
                                           (SEQ ID NO: 47)
    CDR2: AVSSGGSTYYVDSVKG
                                           (SEQ ID NO: 48)
    CDR3: ETGPYGPPKRDY;
```

(ii) a polypeptide comprising a first ISVD (a) comprising the following CDR sequences:

```
    CDR1:
                                           (SEQ ID NO: 40)
    TYVMG
    CDR2:
                                           (SEQ ID NO: 41)
    AISWSGGSTYYADSVKG
    CDR3:
                                           (SEQ ID NO: 42)
    SRGTSTPSRASGVSRYDY,
``` and a second ISVD (b) comprising the following CDR sequences:

```
    CDR1:
                                           (SEQ ID NO: 49)
    INAMG
    CDR2:
                                           (SEQ ID NO: 47)
    AVSSGGSTYYVDSVKG
    CDR3:
                                           (SEQ ID NO: 48)
    ETGPYGPPKRDY;
```

(iii) a polypeptide comprising a first ISVD (a) comprising the following CDR sequences:

```
    CDR1:
                                           (SEQ ID NO: 43)
    RYAVA
    CDR2:
                                           (SEQ ID NO: 44)
    AITWSSGRIDYADSVKG
    CDR3:
                                           (SEQ ID NO: 45)
    DRRPRSTGRSGTGSPSTYDY,
``` and a second ISVD (b) comprising the following CDR sequences:

```
    CDR1:
                                           (SEQ ID NO: 46)
    IGAMG
    CDR2:
                                           (SEQ ID NO: 47)
    AVSSGGSTYYVDSVKG
    CDR3:
                                           (SEQ ID NO: 48)
    ETGPYGPPKRDY;
``` and (iv) a polypeptide comprising a first ISVD (a) comprising the following CDR sequences:

```
    CDR1:
                                           (SEQ ID NO: 43)
    RYAVA
    CDR2:
                                           (SEQ ID NO: 44)
    AITWSSGRIDYADSVKG
    CDR3:
                                           (SEQ ID NO: 45)
    DRRPRSTGRSGTGSPSTYDY,
``` and a second ISVD (b) comprising the following CDR sequences:

```
    CDR1:
                                           (SEQ ID NO: 49)
    INAMG
    CDR2:
                                           (SEQ ID NO: 47)
    AVSSGGSTYYVDSVKG
    CDR3:
                                           (SEQ ID NO: 48)
    ETGPYGPPKRDY;
``` wherein the PD-1 antibody is selected from the group consisting of (i) an anti-PD1 antibody comprising heavy chain CDRs comprising the amino acid sequence of SEQ ID NO:1 (HCDR1), SEQ ID NO:2 (HCDR2) and SEQ ID NO:3 (HCDR3) and light chain CDRs comprising the amino acid sequence of SEQ ID NO:4 (LCDR1), SEQ ID NO:5 (LCDR2) and SEQ ID NO:6 (LCDR3);

(ii) an anti-PD1 antibody comprising heavy chain CDRs comprising the amino acid sequence of SEQ ID NO:7 (HCDR1), SEQ ID NO:8 (HCDR2) and SEQ ID NO:9 (HCDR3) and light chain CDRs comprising the amino acid sequence of SEQ ID NO:10 (LCDR1), SEQ ID NO:11 (LCDR2) and SEQ ID NO:12 (LCDR3); and (iii) an anti-PD1 antibody comprising heavy chain CDRs comprising the amino acid sequence of SEQ ID NO:13 (HCDR1), SEQ ID NO:14 (HCDR2) and SEQ ID NO:15 (HCDR3) and light chain CDRs comprising the amino acid sequence of SEQ ID NO:16 (LCDR1), SEQ ID NO:17 (LCDR2) and SEQ ID NO:18 (LCDR3).

In another aspect, the invention provides for the use of a PD-1 antibody for preparing a pharmaceutical composition for use in a method of treating and/or preventing a hyperproliferative disease, preferably cancer, wherein the PD-1-antibody is to be used in combination with a LRP5 antagonist;

wherein the LRP5 antagonist is selected from the group consisting of
(i) a polypeptide comprising a first immunoglobulin single variable domain (ISVD)
  (a) comprising the following CDR sequences:

```
CDR1:
                                      (SEQ ID NO: 40)
TYVMG

CDR2:
                                      (SEQ ID NO: 41)
AISWSGGSTYYADSVKG

CDR3:
                                      (SEQ ID NO: 42)
SRGTSTPSRASGVSRYDY,
``` and
a second ISVD (b) comprising the following CDR sequences:

```
CDR1:
                                      (SEQ ID NO: 46)
IGAMG

CDR2:
                                      (SEQ ID NO: 47)
AVSSGGSTYYVDSVKG

CDR3:
                                      (SEQ ID NO: 48)
ETGPYGPPKRDY;
```

(ii) a polypeptide comprising a first ISVD (a) comprising the following CDR sequences:

```
CDR1:
                                      (SEQ ID NO: 40)
TYVMG

CDR2:
                                      (SEQ ID NO: 41)
AISWSGGSTYYADSVKG

CDR3:
                                      (SEQ ID NO: 42)
SRGTSTPSRASGVSRYDY,
``` and
a second ISVD (b) comprising the following CDR sequences:

```
CDR1:
                                      (SEQ ID NO: 49)
INAMG

CDR2:
                                      (SEQ ID NO: 47)
AVSSGGSTYYVDSVKG

CDR3:
                                      (SEQ ID NO: 48)
ETGPYGPPKRDY;
```

(iii) a polypeptide comprising a first ISVD (a) comprising the following CDR sequences:

```
CDR1:
                                      (SEQ ID NO: 43)
RYAVA

CDR2:
                                      (SEQ ID NO: 44)
AITWSSGRIDYADSVKG

CDR3:
                                      (SEQ ID NO: 45)
DRRPRSTGRSGTGSPSTYDY,
``` and
a second ISVD (b) comprising the following CDR sequences:

```
CDR1:
                                      (SEQ ID NO: 46)
IGAMG

CDR2:
                                      (SEQ ID NO: 47)
AVSSGGSTYYVDSVKG

CDR3:
                                      (SEQ ID NO: 48)
ETGPYGPPKRDY;
``` and
(iv) a polypeptide comprising a first ISVD (a) comprising the following CDR sequences:

```
CDR1:
                                      (SEQ ID NO: 43)
RYAVA

CDR2:
                                      (SEQ ID NO: 44)
AITWSSGRIDYADSVKG

CDR3:
                                      (SEQ ID NO: 45)
DRRPRSTGRSGTGSPSTYDY,
``` and
a second ISVD (b) comprising the following CDR sequences:

```
CDR1:
                                      (SEQ ID NO: 49)
INAMG

CDR2:
                                      (SEQ ID NO: 47)
AVSSGGSTYYVDSVKG

CDR3:
                                      (SEQ ID NO: 48)
ETGPYGPPKRDY;
``` wherein the PD-1 antibody is selected from the group consisting of
(i) an anti-PD1 antibody comprising heavy chain CDRs comprising the amino acid sequence of SEQ ID NO:1 (HCDR1), SEQ ID NO:2 (HCDR2) and SEQ ID NO:3

(HCDR3) and light chain CDRs comprising the amino acid sequence of SEQ ID NO:4 (LCDR1), SEQ ID NO:5 (LCDR2) and SEQ ID NO:6 (LCDR3);

(ii) an anti-PD1 antibody comprising heavy chain CDRs comprising the amino acid sequence of SEQ ID NO:7 (HCDR1), SEQ ID NO:8 (HCDR2) and SEQ ID NO:9 (HCDR3) and light chain CDRs comprising the amino acid sequence of SEQ ID NO:10 (LCDR1), SEQ ID NO:11 (LCDR2) and SEQ ID NO:12 (LCDR3); and (iii) an anti-PD1 antibody comprising heavy chain CDRs comprising the amino acid sequence of SEQ ID NO:13 (HCDR1), SEQ ID NO:14 (HCDR2) and SEQ ID NO:15 (HCDR3) and light chain CDRs comprising the amino acid sequence of SEQ ID NO:16 (LCDR1), SEQ ID NO:17 (LCDR2) and SEQ ID NO:18 (LCDR3).

In another aspect, the invention provides for a pharmaceutical composition, comprising:

an LRP5 antagonist;

a PD-1 antibody; and, optionally, one or more pharmaceutically acceptable carriers, excipients and/or vehicles;

wherein the LRP5 antagonist is selected from the group consisting of (i) a polypeptide comprising a first immunoglobulin single variable domain (ISVD) (a) comprising the following CDR sequences:

```
CDR1:
                                          (SEQ ID NO: 40)
TYVMG

CDR2:
                                          (SEQ ID NO: 41)
AISWSGGSTYYADSVKG

CDR3:
                                          (SEQ ID NO: 42)
SRGTSTPSRASGVSRYDY,
``` and a second ISVD (b) comprising the following CDR sequences:

```
CDR1:
                                          (SEQ ID NO: 46)
IGAMG

CDR2:
                                          (SEQ ID NO: 47)
AVSSGGSTYYVDSVKG

CDR3:
                                          (SEQ ID NO: 48)
ETGPYGPPKRDY;
```

(ii) a polypeptide comprising a first ISVD (a) comprising the following CDR sequences:

```
CDR1:
                                          (SEQ ID NO: 40)
TYVMG

CDR2:
                                          (SEQ ID NO: 41)
AISWSGGSTYYADSVKG

CDR3:
                                          (SEQ ID NO: 42)
SRGTSTPSRASGVSRYDY,
``` and a second ISVD (b) comprising the following CDR sequences:

```
CDR1:
                                          (SEQ ID NO: 49)
INAMG

CDR2:
                                          (SEQ ID NO: 47)
AVSSGGSTYYVDSVKG

CDR3:
                                          (SEQ ID NO: 48)
ETGPYGPPKRDY;
```

(iii) a polypeptide comprising a first ISVD (a) comprising the following CDR sequences:

```
CDR1:
                                          (SEQ ID NO: 43)
RYAVA

CDR2:
                                          (SEQ ID NO: 44)
AITWSSGRIDYADSVKG

CDR3:
                                          (SEQ ID NO: 45)
DRRPRSTGRSGTGSPSTYDY,
``` and a second ISVD (b) comprising the following CDR sequences:

```
CDR1:
                                          (SEQ ID NO: 46)
IGAMG

CDR2:
                                          (SEQ ID NO: 47)
AVSSGGSTYYVDSVKG

CDR3:
                                          (SEQ ID NO: 48)
ETGPYGPPKRDY;
``` and (iv) a polypeptide comprising a first ISVD (a) comprising the following CDR sequences:

```
CDR1:
                                          (SEQ ID NO: 43)
RYAVA

CDR2:
                                          (SEQ ID NO: 44)
AITWSSGRIDYADSVKG
```

```
        CDR3:
                               (SEQ ID NO: 45)
        DRRPRSTGRSGTGSPSTYDY,
```
and a second ISVD (b) comprising the following CDR sequences:

```
        CDR1:
                               (SEQ ID NO: 49)
        INAMG

CDR2:
                               (SEQ ID NO: 47)
        AVSSGGSTYYVDSVKG

CDR3:
                               (SEQ ID NO: 48)
        ETGPYGPPKRDY;
``` wherein the PD-1 antibody is selected from the group consisting of
  (i) an anti-PD1 antibody comprising heavy chain CDRs comprising the amino acid sequence of SEQ ID NO:1 (HCDR1), SEQ ID NO:2 (HCDR2) and SEQ ID NO:3 (HCDR3) and light chain CDRs comprising the amino acid sequence of SEQ ID NO:4 (LCDR1), SEQ ID NO:5 (LCDR2) and SEQ ID NO:6 (LCDR3);
  (ii) an anti-PD1 antibody comprising heavy chain CDRs comprising the amino acid sequence of SEQ ID NO:7 (HCDR1), SEQ ID NO:8 (HCDR2) and SEQ ID NO:9 (HCDR3) and light chain CDRs comprising the amino acid sequence of SEQ ID NO:10 (LCDR1), SEQ ID NO:11 (LCDR2) and SEQ ID NO:12 (LCDR3); and
  (iii) an anti-PD1 antibody comprising heavy chain CDRs comprising the amino acid sequence of SEQ ID NO:13 (HCDR1), SEQ ID NO:14 (HCDR2) and SEQ ID NO:15 (HCDR3) and light chain CDRs comprising the amino acid sequence of SEQ ID NO:16 (LCDR1), SEQ ID NO:17 (LCDR2) and SEQ ID NO:18 (LCDR3).

In some embodiments, the pharmaceutical composition is for use in a method of treating and/or preventing a hyperproliferative disease, preferably cancer.

In another aspect, the invention provides for a kit comprising in one or more containers
  a first pharmaceutical composition or dosage form comprising an LRP5 antagonist and, optionally, one or more pharmaceutically acceptable carriers, excipients and/or vehicles;
  a second pharmaceutical composition or dosage form comprising a PD-1 antibody and, optionally, one or more pharmaceutically acceptable carriers, excipients and/or vehicles;
  and optionally a package insert comprising printed instructions;
wherein the LRP5 antagonist is selected from the group consisting of
  (i) a polypeptide comprising a first immunoglobulin single variable domain (ISVD) (a) comprising the following CDR sequences:

```
        CDR1:
                               (SEQ ID NO: 40)
        TYVMG

CDR2:
                               (SEQ ID NO: 41)
        AISWSGGSTYYADSVKG

CDR3:
                               (SEQ ID NO: 42)
        SRGTSTPSRASGVSRYDY,
```
and a second ISVD (b) comprising the following CDR sequences:

```
        CDR1:
                               (SEQ ID NO: 46)
        IGAMG

CDR2:
                               (SEQ ID NO: 47)
        AVSSGGSTYYVDSVKG

CDR3:
                               (SEQ ID NO: 48)
        ETGPYGPPKRDY;
```

(ii) a polypeptide comprising a first ISVD (a) comprising the following CDR sequences:

```
        CDR1:
                               (SEQ ID NO: 40)
        TYVMG

CDR2:
                               (SEQ ID NO: 41)
        AISWSGGSTYYADSVKG

CDR3:
                               (SEQ ID NO: 42)
        SRGTSTPSRASGVSRYDY,
```
and a second ISVD (b) comprising the following CDR sequences:

```
        CDR1:
                               (SEQ ID NO: 49)
        INAMG

CDR2:
                               (SEQ ID NO: 47)
        AVSSGGSTYYVDSVKG

CDR3:
                               (SEQ ID NO: 48)
        ETGPYGPPKRDY;
```

(iii) a polypeptide comprising a first ISVD (a) comprising the following CDR sequences:

```
        CDR1:
                               (SEQ ID NO: 43)
        RYAVA

CDR2:
                               (SEQ ID NO: 44)
        AITWSSGRIDYADSVKG
```

CDR3:
DRRPRSTGRSGTGSPSTYDY, (SEQ ID NO: 45)

and a second ISVD (b) comprising the following CDR sequences:

CDR1:
IGAMG (SEQ ID NO: 46)

CDR2:
AVSSGGSTYYVDSVKG (SEQ ID NO: 47)

CDR3:
ETGPYGPPKRDY; (SEQ ID NO: 48)

and (iv) a polypeptide comprising a first ISVD (a) comprising the following CDR sequences:

CDR1:
RYAVA (SEQ ID NO: 43)

CDR2:
AITWSSGRIDYADSVKG (SEQ ID NO: 44)

CDR3:
DRRPRSTGRSGTGSPSTYDY, (SEQ ID NO: 45)

and a second ISVD (b) comprising the following CDR sequences:

CDR1:
INAMG (SEQ ID NO: 49)

CDR2:
AVSSGGSTYYVDSVKG (SEQ ID NO: 47)

CDR3:
ETGPYGPPKRDY; (SEQ ID NO: 48)

wherein the PD-1 antibody is selected from the group consisting of
(i) an anti-PD1 antibody comprising heavy chain CDRs comprising the amino acid sequence of SEQ ID NO:1 (HCDR1), SEQ ID NO:2 (HCDR2) and SEQ ID NO:3 (HCDR3) and light chain CDRs comprising the amino acid sequence of SEQ ID NO:4 (LCDR1), SEQ ID NO:5 (LCDR2) and SEQ ID NO:6 (LCDR3);
(ii) an anti-PD1 antibody comprising heavy chain CDRs comprising the amino acid sequence of SEQ ID NO:7 (HCDR1), SEQ ID NO:8 (HCDR2) and SEQ ID NO:9 (HCDR3) and light chain CDRs comprising the amino acid sequence of SEQ ID NO:10 (LCDR1), SEQ ID NO:11 (LCDR2) and SEQ ID NO:12 (LCDR3); and
(iii) an anti-PD1 antibody comprising heavy chain CDRs comprising the amino acid sequence of SEQ ID NO:13 (HCDR1), SEQ ID NO:14 (HCDR2) and SEQ ID NO:15 (HCDR3) and light chain CDRs comprising the amino acid sequence of SEQ ID NO:16 (LCDR1), SEQ ID NO:17 (LCDR2) and SEQ ID NO:18 (LCDR3).

In some embodiments, the kit according to the invention is for use in a method of treating and/or preventing a hyperproliferative disease, preferably cancer.

In preferred embodiments of the invention the LRP5 antagonist is selected from the group consisting of
(i) a polypeptide comprising a first ISVD comprising an amino acid sequence of SEQ ID NO:50, and a second ISVD comprising the sequence of SEQ ID NO:61;
(ii) a polypeptide comprising a first ISVG comprising an amino acid sequence of SEQ ID NO:51 and a second ISVD comprising the sequence of SEQ ID NO:52;
(iii) a polypeptide comprising a first ISVD comprising the sequence of SEQ ID NO:62, and a second ISVD comprising the sequence of SEQ ID NO:53;
(iv) a polypeptide comprising a first ISVD comprising an amino acid sequence of SEQ ID NO:50 and a second ISVD comprising the sequence of SEQ ID NO:53;
(v) a polypeptide comprising a first ISVD comprising an amino acid sequence of SEQ ID NO:62 and a second ISVD comprising the sequence of SEQ ID NO:61; and
(vi) a polypeptide comprising a first ISVD comprising an amino acid sequence of SEQ ID NO:51 and a second ISVD comprising the sequence of SEQ ID NO:53;
preferably the LRP5 antagonist further comprises an Alb11 domain comprising the amino acid sequence of SEQ ID NO:60.

In particularly preferred embodiments, the LRP5 antagonist comprises a polypeptide comprising an amino acid sequence selected from the group consisting of SEQ ID NO: 57, SEQ ID NO:58 and SEQ ID NO:59.

In preferred embodiments of the invention, the anti-PD1 antibody is selected from the group consisting of
(i) an antibody comprising a heavy chain variable domain comprising the amino acid sequence of SEQ ID NO:19 and a light chain variable domain comprising the amino acid sequence of SEQ ID NO:20;
(ii) an antibody comprising a heavy chain variable domain comprising the amino acid sequence of SEQ ID NO:21 and a light chain variable domain comprising the amino acid sequence of SEQ ID NO:22;
(iii) an antibody comprising a heavy chain variable domain comprising the amino acid sequence of SEQ ID NO:23 and a light chain variable domain comprising the amino acid sequence of SEQ ID NO:24;
(iv) an antibody comprising a heavy chain variable domain comprising the amino acid sequence of SEQ ID NO:25 and a light chain variable domain comprising the amino acid sequence of SEQ ID NO:26; and
(v) an antibody comprising a heavy chain variable domain comprising the amino acid sequence of SEQ ID NO:27 and a light chain variable domain comprising the amino acid sequence of SEQ ID NO:28.

In particularly preferred embodiments of the invention, the PD-1 antibody is selected from the group consisting of
(i) an antibody comprising a heavy chain comprising the amino acid sequence of SEQ ID NO: 29 and a light chain comprising the amino acid sequence of SEQ ID NO: 30;
(ii) an antibody comprising a heavy chain comprising the amino acid sequence of SEQ ID NO: 31 and a light chain comprising the amino acid sequence of SEQ ID NO: 32;

(iii) an antibody comprising a heavy chain comprising the amino acid sequence of SEQ ID NO: 33 and a light chain comprising the amino acid sequence of SEQ ID NO: 34;

(iv) an antibody comprising a heavy chain comprising the amino acid sequence of SEQ ID NO: 35 and a light chain comprising the amino acid sequence of SEQ ID NO: 36; and (v) an antibody comprising a heavy chain comprising the amino acid sequence of SEQ ID NO: 37 and a light chain comprising the amino acid sequence of SEQ ID NO: 38.

In some embodiments of the invention, the PD-1 antibody is to be administered simultaneously, concurrently, sequentially, successively, alternately or separately with the LRP5 antagonist.

In preferred embodiments, the LRP5 antagonist and the PD-1 antibody are to be administered according to the following treatment regimen:

(i) a first treatment period, wherein the LRP5 antagonist and the PD-1 antibody are to be administered simultaneously or concurrently, preferably every three or four weeks; and (ii) a second treatment period, wherein only the PD-1 antibody is to be administered and the LRP5 antagonist is not to be administered, preferably wherein the PD-1 antibody is to be administered every three or four weeks.

In preferred embodiments of the invention, the hyperproliferative disease to be treated is a cancer selected from the group consisting of gastrointestinal cancers, melanoma tumours, bladder cancer and lung cancer (e.g. NSCLC), even more preferably the cancer is an immunotherapy-resistant gastrointestinal cancer (including but not limited to esophageal cancer (e.g., gastroesophageal junction cancer), stomach (gastric) cancer, hepatocellularcarcinoma, biliary tract cancer (e.g., cholangiocarcinoma), gallbladder cancer, pancreatic cancer or colorectal cancer (CRC)), immunotherapy-resistant melanoma, immunotherapy-resistant bladder cancer or an immunotherapy-resistant lung cancer.

In alternative preferred embodiments of the invention, the hyperproliferative disease to be treated is a solid immunotherapy-resistant tumour.

BRIEF DESCRIPTION OF THE FIGURES

FIG. 1A-1H: shows the anti-tumor activity of the exemplary LRP5 antagonist as single agent and in combination with an exemplary antibody to PD-1, in a subcutaneous syngeneic mouse model derived from the breast cancer cell line EMT6 in Balb/c mice. FIG. 1A: Measurement of tumor volume over the indicated days after treatment with isotype matched antibody; 1B: with LRP5 antagonist; 1C: with PD-1 antibody; and 1D: with LRP5 antagonist+PD-1 antibodies. FIG. 1E: Measurement of tumor shrinkage response at the indicated days after treatment with isotype matched antibody; 1F: with LRP5 antagonist; 1G: with PD-1 antibody; and 1H: with LRP5 antagonist+PD-1 antibodies. The numbering indicated with * shows the number of mice out of the total investigated mice in which a response was observed, i.e. in which the ratio between the tumor volume at the end and the start of treatment is below 1 (i.e. indicating shrinkage of the tumor).

DETAILED DESCRIPTION OF THE INVENTION

Definitions

The above and other aspects and embodiments of the invention will become clear from the further description herein, in which:

Unless indicated or defined otherwise, all terms used have their usual meaning in the art, which will be clear to the person skilled in the art to which this invention belongs. In case of conflict, the patent specification, including definitions, will prevail. Reference is for example made to the standard handbooks, such as Sambrook et al, "Molecular Cloning: A Laboratory Manual" (2nd Ed.), Vols. 1-3, Cold Spring Harbor Laboratory Press (1989); Lewin, "Genes IV", Oxford University Press, New York, (1990), and Roitt et al., "Immunology" ($2^{nd}$ Ed.), Gower Medical Publishing, London, New York (1989), as well as to the general background art cited herein. Furthermore, unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein.

The term "antibody" encompasses antibodies, antibody fragments, antibody-like molecules and conjugates with any of the above. Antibodies include, but are not limited to, poly- or monoclonal, chimeric, humanized, human, mono-, bi- or multispecific antibodies. The term "antibody" shall encompass complete immunoglobulins as they are produced by lymphocytes and for example present in blood sera, monoclonal antibodies secreted by hybridoma cell lines, polypeptides produced by recombinant expression in host cells, which have the binding specificity of immunoglobulins or monoclonal antibodies, and molecules which have been derived from such immunoglobulins, monoclonal antibodies, or polypeptides by further processing while retaining their binding specificity. In particular, the term "antibody" includes complete immunoglobulins comprising two heavy chains and two light chains. In another embodiment, the term encompasses a fragment of an immunoglobulin, like Fab fragments. In another embodiment, the term "antibody" encompasses a polypeptide having one or more variable domains derived from an immunoglobulin, like single chain antibodies (scFv), single domain antibodies, and the like.

A "human antibody" is one which possesses an amino acid sequence which corresponds to that of an antibody produced by a human cell or derived from a non-human source that utilizes human antibody repertoires or other human antibody-encoding sequences. This definition of a human antibody specifically excludes a humanized antibody comprising non-human antigen-binding residues.

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

A "humanized" antibody refers to a chimeric antibody comprising amino acid residues from non-human hypervariable regions (HVRs) and amino acid residues from human framework regions (FRs). In certain embodiments, a humanized antibody will comprise substantially all of at least one, and typically two, variable domains, in which all or substantially all of the HVRs (e.g. complementary determining regions (CDRs)) correspond to those of a non-human antibody, and all or substantially the entire framework regions (FRs) correspond to those of a human antibody. A humanized antibody optionally may comprise at least a portion of an antibody constant region derived from a human antibody. A "humanized form" of an antibody, e.g. a non-human antibody, refers to an antibody that has undergone humanization.

The expressions "variable domain" or "variable region" or Fv as used herein denotes each of the pair of light and heavy chains which is involved directly in binding the antibody to the antigen. The variable domain of a light chain is abbreviated as "VL" and the variable domain of a heavy chain is abbreviated as "VH". The variable light and heavy chain domains have the same general structure and each domain comprises four framework (FR) regions whose sequences are widely conserved, connected by three HVRs (or CDRs). The framework regions adopt a beta-sheet conformation and the CDRs may form loops connecting the beta-sheet structure. The CDRs in each chain are held in their three-dimensional structure by the framework regions and form together with the CDRs from the other chain the antigen binding site. The antibody's heavy and light chain CDR regions play a particularly important role in the binding specificity/affinity of the antibodies according to the invention and therefore provide a further object of the invention.

Within the context of this invention, reference to CDR's in connection with antibodies (e.g. PD1 antibodies) is based on the definition of Chothia (Chothia and Lesk, J. Mol. Biol. 1987, 196: 901-917), together with Kabat (E. A. Kabat, T. T. Wu, H. Bilofsky, M. Reid-Miller and H. Perry, Sequence of Proteins of Immunological Interest, National Institutes of Health, Bethesda (1983)).

Unless indicated otherwise, the terms "immunoglobulin" and "immunoglobulin sequence"-whether used herein to refer to a heavy chain antibody or to a conventional 4-chain antibody—are used as general terms to include both the full-size antibody, the individual chains thereof, as well as all parts, domains or fragments thereof (including but not limited to antigen-binding domains or fragments such as VHH domains or VH/VL domains, respectively). In addition, the term "sequence" as used herein (for example in terms like "immunoglobulin sequence", "antibody sequence", "(single) variable domain sequence", "VHH sequence" or "protein sequence"), should generally be understood to include both the relevant amino acid sequence as well as nucleic acid sequences or nucleotide sequences encoding the same, unless the context requires a more limited interpretation.

The term "domain" (of a polypeptide or protein) as used herein refers to a folded protein structure which has the ability to retain its tertiary structure independently of the rest of the protein. Generally, domains are responsible for discrete functional properties of proteins, and in many cases can be added, removed or transferred to other proteins without loss of function of the remainder of the protein and/or of the domain.

The term "immunoglobulin domain" as used herein refers to a globular region of an antibody chain (such as e.g. a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a 2-layer sandwich of about 7 antiparallel beta-strands arranged in two beta-sheets, optionally stabilized by a conserved disulphide bond.

The term "immunoglobulin variable domain" as used herein means an immunoglobulin domain essentially consisting of four "framework regions" which are referred to in the art and herein as "framework region 1" or "FR1"; as "framework region 2" or"FR2"; as "framework region 3" or "FR3"; and as "framework region 4" or "FR4", respectively; which framework regions are interrupted by three "complementarity determining regions" or "CDRs", which are referred to in the art and herein as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confer specificity to an antibody for the antigen by carrying the antigen-binding site.

The term "immunoglobulin single variable domain" (or ISVD) as used herein means an immunoglobulin variable domain which is capable of specifically binding to an epitope of the antigen without pairing with an additional variable immunoglobulin domain. One example of ISVDs in the meaning of the present invention are "domain antibodies", such as the ISVDs VH and VL (VH domains and VL domains). Another important example of ISVDs are "VHH domains" (or simply "VHHs") from camelids, as defined hereinafter.

In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an ISVD, as, in these cases, binding to the respective epitope of an antigen would normally not occur by one (single) immunoglobulin domain but by a pair of (associating) immunoglobulin domains such as light and heavy chain variable domains, i.e. by a VH-VL pair of immunoglobulin domains, which jointly bind to an epitope of the respective antigen.

"VHH domains", also known as VHHs, $V_HH$ domains, VHH antibody fragments, and VHH antibodies, have originally been described as the antigen binding immunoglobulin (variable) domain of "heavy chain antibodies" (i.e. of "antibodies devoid of light chains"; Hamers-Casterman C, Atarhouch T, Muyldermans S, Robinson G, Hamers C, Songa E B, Bendahman N, Hamers R.: "Naturally occurring antibodies devoid of light chains"; Nature 363, 446-448 (1993)). The term "VHH domain" has been chosen in order to distinguish these variable domains from the heavy chain variable domains that are present in conventional 4-chain antibodies (which are referred to herein as "VH domains" or "VH domains") and from the light chain variable domains that are present in conventional 4-chain antibodies (which are referred to herein as "VL domains" or "VL domains"). VHH domains can specifically bind to an epitope without an additional antigen binding domain (as opposed to VH or VL domains in a conventional 4-chain antibody, in which case the epitope is recognized by a VL domain together with a VH domain). VHH domains are small, robust and efficient antigen recognition units formed by a single immunoglobulin domain.

In the context of the present invention, the terms VHH domain, VHH, $V_HH$ domain, VHH antibody fragment, VHH antibody, as well as "Nanobody®" and "Nanobody® domain" ("Nanobody" being a trademark of the company Ablynx N.V.; Ghent; Belgium) are used interchangeably and are representatives of ISVDs (having the structure: FR1-CDR1-FR2-CDR2-FR3-CDR3-FR4 and specifically binding to an epitope without requiring the presence of a second immunoglobulin variable domain), and which can also be distinguished from VH domains by the so-called "hallmark residues", as defined in e.g. WO2009/109635, FIG. 1.

The amino acid residues of a VHH domain are numbered according to the general numbering for VH domains given by Kabat et al. ("Sequence of proteins of immunological interest", US Public Health Services, NIH Bethesda, Md., Publication No. 91), as applied to VHH domains from Camelids, as shown e.g. in FIG. 2 of Riechmann and Muyldermans, J. Immunol. Methods 231, 25-38 (1999). According to this numbering, FR1 comprises the amino acid residues at positions 1-30,
CDR1 comprises the amino acid residues at positions 31-35,
FR2 comprises the amino acids at positions 36-49,
CDR2 comprises the amino acid residues at positions 50-65,
FR3 comprises the amino acid residues at positions 66-94,
CDR3 comprises the amino acid residues at positions 95-102, and
FR4 comprises the amino acid residues at positions 103-113.

However, it should be noted that—as is well known in the art for VH domains and for VHH domains—the total number of amino acid residues in each of the CDRs may vary and, consequently, may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that although the numbering of the amino acid residues of a VHH domain is based on the numbering according to Kabat, the actual numbering of the amino acid residues in the actual sequence can differ. As this kind of variation is well known in the art, the respective numbering and the allocation of framework regions and CDRs within such a sequence can be determined by the skilled person without further ado.

Alternative methods for numbering the amino acid residues of VH domains, which methods can also be applied in an analogous manner to VHH domains, are known in the art. However, in the present description, claims and figures in connection with ISVDs described herein, the numbering according to Kabat and applied to VHH domains as described above will be followed, unless indicated otherwise.

The total number of amino acid residues in a VHH domain will usually be in the range of from 110 to 120, often between 112 and 115. It should however be noted that smaller and longer sequences may also be suitable for the purposes described herein.

Methods of obtaining VHH domains binding to a specific antigen or epitope have been described earlier, e.g. in WO2006/040153 and WO2006/122786. VHH domains derived from camelids can be "humanized" by replacing one or more amino acid residues in the amino acid sequence of the original VHH sequence by one or more of the amino acid residues that occur at the corresponding position(s) in a VH domain from a conventional 4-chain antibody from a human being. A humanized VHH domain can contain one or more fully human framework region sequences, and, in an even more specific embodiment, can contain human framework region sequences derived from DP-29, DP-47, DP-51, or parts thereof, optionally combined with JH sequences, such as JH5.

The terms "epitope" and "antigenic determinant", which can be used interchangeably, refer to the part of a macromolecule, such as a polypeptide, that is recognized by antigen-binding molecules, such as conventional antibodies or the polypeptides of the invention, and more particularly by the antigen-binding site of said molecules. Epitopes define the minimum binding site for an immunoglobulin, and thus represent the target of specificity of an immunoglobulin.

The part of an antigen-binding molecule (such as a conventional antibody or a polypeptide disclosed herein) that recognizes the epitope is called a paratope.

The term "biparatopic" (antigen-)binding molecule or "biparatopic" polypeptide as used herein shall mean a polypeptide comprising a first ISVD and a second ISVD as herein defined, wherein these two variable domains are capable of binding to two different epitopes of one antigen, which epitopes are not normally bound at the same time by one monospecific immunoglobulin, such as e.g. a conventional antibody or one ISVD. The biparatopic polypeptides according to the invention are composed of variable domains which have different epitope specificities, and do not contain mutually complementary variable domain pairs which bind to the same epitope. They do therefore not compete with each other for binding to LRP5.

A polypeptide (such as an immunoglobulin, an antibody, an ISVD, or generally an antigen binding molecule or a fragment thereof) that can "bind", "bind to", "specifically bind", or "specifically bind to", that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein.

Generally, the term "specificity" refers to the number of different types of antigens or epitopes to which a particular antigen-binding molecule or antigen-binding protein (such as an immunoglobulin, an antibody, an ISVD) can bind. The specificity of an antigen-binding protein can be determined based on its affinity and/or avidity. The affinity, represented by the equilibrium constant for the dissociation of an antigen with an antigen-binding protein ($K_D$), is a measure for the binding strength between an epitope and an antigen-binding site on the antigen-binding protein: the lesser the value of the $K_D$, the stronger the binding strength between an epitope and the antigen-binding molecule (alternatively, the affinity can also be expressed as the affinity constant ($K_A$), which is $1/K_D$). As will be clear to the skilled person (for example on the basis of the further disclosure herein), affinity can be determined in a manner known per se, depending on the specific antigen of interest. Avidity is the measure of the strength of binding between an antigen-binding molecule (such as an immunoglobulin, an antibody, an ISVD,) and the pertinent antigen. Avidity is related to both the affinity between an epitope and its antigen binding site on the antigen-binding molecule and the number of pertinent binding sites present on the antigen-binding molecule.

Typically, antigen-binding molecules (such as the polypeptides capable of specifically binding to LRP5) will bind with a dissociation constant ($K_D$) of 10E-5 to 10E-14 moles/liter (M) or less, and preferably 10E-7 to 10E-14 moles/liter (M) or less, more preferably 10E-8 to 10E-14 moles/liter, and even more preferably 10E-11 to 10E-13 (as measured e.g. in a Kinexa assay; known in the art), and/or with an association constant ($K_D$) of at least 10E7 ME-1, preferably at least 10E8 ME-1, more preferably at least 10E9 ME-1, such as at least 10E11 ME-1. Any $K_D$ value greater than 10E-4 M is generally considered to indicate non-specific binding. Preferably, an antigen binding molecule (such as the polypeptides capable of specifically binding to LRP5) will bind to the desired antigen with a $K_D$ less than 500 nM, preferably less than 200 nM, more preferably less than 10 nM, such as less than 500 pM. Specific binding of an antigen-binding protein to an antigen or epitope can be determined in any suitable manner known per se, including, for example, the assays described herein, Scatchard analysis and/or competitive binding assays, such as radioimmunoassays (RIA), enzyme immunoassays (EIA) and sandwich competition assays, and the different variants thereof known per se in the art.

LRP5 antagonists (this term is used interchangeably with the terms "polypeptide specifically binding to LRP5" or "polypeptide capable of specifically binding to LRP5") described herein have specificity for LRP5, in that they comprise ISVDs that bind to epitopes of LRP5 but do not, or essentially do not, cross-react with an epitope with a structure similar to the epitopes of LRP5, or with an unrelated structure. In a preference, the LRP5 antagonists have an affinity and/or avidity for LRP5, especially human LRP5, that is at least 10 times, preferably at least 100 times, more preferably at least 1000 times, even more preferably at least 10000 times, yet even more preferably at least 100000 times or at least 1000000 times stronger than their affinity and/or avidity for any other antigen, in particular LRP6, and more specifically human LRP6 (Accession number: UniProtKB—O75581/LRP6_HUMAN). Most preferably, the LRP5 antagonists are not cross-reactive to LRP6, in particular human LRP6.

The LRP5 antagonists shall bind to the human forms of LRP5, and preferably also to counterparts in other species relevant for drug development, i.e. cynomolgus and mouse LRP5.

When used herein the term "comprising" and variations thereof such as "comprises" and "comprise" can be substituted with the term "containing" or "including" or "having." Furthermore, the term "comprising" also explicitly encompasses embodiments "consisting of" the recited elements.

Combination Therapy

It is a purpose of the present invention to provide novel therapies for treating or controlling various hyperproliferative diseases, in particular various malignancies.

The inventors of the present application, surprisingly, discovered that the use of an LRP5 antagonist in combination with an anti-PD-1 (Programmed cell Death 1) antibody, has the potential to improve clinical outcome compared to the use of a LRP5 antagonist or an anti-PD-1 antibody alone.

Specifically, in preclinical studies the inventors tested the immune modulatory function and anti-tumor activity of an LRP5 antagonist either alone or in combination with an anti-PD-1 antibody (see Example 1 below). Complete responses, as determined by histopathological analysis, and abundant T cell tumor infiltration was only observed for the combination of the LRP5 antagonist with the anti-PD-1 antibody. FACS analysis of the tumor draining lymph nodes further showed that this combination treatment led to an increased number of activated dendritic cells (DCs) in the draining lymph nodes. Without wishing to be bound by theory, these findings indicate that the combination treatment of a LRP5 antagonist with an anti-PD-1 antibody leads to inhibition of the Wnt signalling pathway in DCs, which subsequently leads to an upregulation of pro-inflammatory cytokines, restoration of cross-priming and promotion of tumor T cell infiltration and anti-tumour activity.

Although various combination therapies are known in the art and are currently under investigation (e.g. in preclinical or clinical trials), satisfying therapeutic concepts for the treatment of cancer diseases, in particular solid tumors such as lung cancer (e.g. NSCLC), melanoma, bladder and gastrointestinal cancers, are still lacking. Any therapy which shows advantages over standard therapies, such as for example better treatment outcome, beneficial effects, superior efficacy and/or improved tolerability, such as e.g. reduced side effect, would therefore represent an important development.

The surprising results shown in Example 1 below indicate that the combination of an LRP5 antagonist, which on its own had no therapeutic effect in the tumor model, with an anti-PD-1 antibody, which had only a limited therapeutic effect, resulted in a synergistic (i.e. more than additive) interaction of these two compounds that provides for superior results in that a complete response was obtainable.

Thus, the invention relates to methods for the treatment and/or prevention of hyperproliferative diseases, in particular cancer, comprising the combined administration of an LRP5 antagonist and an anti-PD-1 antibody, each as described herein, as well as to medical uses, to uses, to pharmaceutical compositions or combinations and kits comprising such therapeutic agents.

Further, the invention relates to anti-cancer therapies comprising using an LRP5 antagonist and an anti-PD-1 antibody, each as described herein, in combination.

Such a combined treatment may be given as a non-fixed (e.g. free) combination of the substances or in the form of a fixed combination, including kit-of-parts.

For the treatment of diseases of oncological nature, a large number of anti-cancer agents (including target-specific and non-target-specific anticancer agents) have already been suggested, which can be used as monotherapy or as combination therapy involving more than one agent (e.g. dual or triple combination therapy) and/or which may be combined with radiotherapy (e.g. irradiation treatment), radio-immunotherapy and/or surgery. Therefore, the combined treatment described herein may be given in addition to further therapeutic agents and/or treatments such as radiotherapy, radio-immunotherapy and surgery.

LRP5 Antagonist

A polypeptide capable of specifically binding to LRP5 (also referred to herein as an LRP5 antagonist) within the meaning of this invention and all of its embodiments is a polypeptide which binds to low-density lipoprotein receptor-like protein 5 (LRP5), the polypeptide comprising two or more ISVDs binding to LRP5 at different epitopes, preferably the first domain blocks a Wnt3a binding site of LRP5, and preferably inhibits Wnt3a-driven target gene transcription, and/or the second domain blocks a Wnt1 binding site of LRP5, and preferably inhibits Wnt1-driven target gene transcription.

In other words, LRP5 antagonists of the invention include:
- a first ISVD which is able to specifically bind to LRP5 via an epitope/in a manner that results in inhibition of the Wnt3a signaling pathway, so that Wnt3a-driven target gene transcription is inhibited, and
- a second ISVD which is able to specifically bind to LRP5 via an epitope/in a manner that results in inhibition of the Wnt1 signaling pathway, so that Wnt1-driven target gene transcription is inhibited.

Due to the two ISVDs present in LRP5 antagonists described above which have two domains that are binding to different epitopes (Wnt1/Wnt3a signaling related), these molecules are biparatopic binding molecules.

In some embodiments of the invention, the LRP5 antagonist comprises
a first ISVD (a) comprising the following CDR sequences:

```
                                    (SEQ ID NO: 40)
        CDR1: TYVMG (SEQ ID NO: 41)
        CDR2: AISWSGGSTYYADSVKG (SEQ ID NO: 42)
        CDR3: SRGTSTPSRASGVSRYDY,
``` and
a second ISVD (b) comprising the following CDR sequences:

```
                                    (SEQ ID NO: 46)
        CDR1: IGAMG (SEQ ID NO: 47)
        CDR2: AVSSGGSTYYVDSVKG (SEQ ID NO: 48)
        CDR3: ETGPYGPPKRDY.
```

This specific combination of CDR sequences is, for example, contained in the LRP5 antagonists termed LRP5#1, LRP5#2, LRP5#3, and LRP5#4 herein below.

In some embodiments of the invention, the LRP5 antagonist comprises
a first ISVD (a) comprising the following CDR sequences:

```
                                    (SEQ ID NO: 40)
        CDR1: TYVMG (SEQ ID NO: 41)
        CDR2: AISWSGGSTYYADSVKG (SEQ ID NO: 42)
        CDR3: SRGTSTPSRASGVSRYDY,
``` and
a second ISVD (b) comprising the following CDR sequences:

```
                                    (SEQ ID NO: 49)
        CDR1: INAMG (SEQ ID NO: 47)
        CDR2: AVSSGGSTYYVDSVKG (SEQ ID NO: 48)
        CDR3: ETGPYGPPKRDY.
```

This specific combination of CDR sequences is, for example, contained in the LRP5 antagonists termed LRP5#5 and LRP5#6 herein below.

In some embodiments of the invention, the LRP5 antagonist comprises
a first ISVD (a) comprising the following CDR sequences:

```
                                    (SEQ ID NO: 43)
        CDR1: RYAVA (SEQ ID NO: 44)
        CDR2: AITWSSGRIDYADSVKG (SEQ ID NO: 45)
        CDR3: DRRPRSTGRSGTGSPSTYDY,
``` and
a second ISVD (b) comprising the following CDR sequences:

```
                                    (SEQ ID NO: 46)
        CDR1: IGAMG (SEQ ID NO: 47)
        CDR2: AVSSGGSTYYVDSVKG (SEQ ID NO: 48)
        CDR3: ETGPYGPPKRDY.
```

This specific combination of CDR sequences is, for example, contained in the LRP5 antagonists termed LRP5#7 and LRP5#8 herein below.

In some embodiments of the invention, the LRP5 antagonist comprises
a first ISVD (a) comprising the following CDR sequences:

```
                                    (SEQ ID NO: 43)
        CDR1: RYAVA (SEQ ID NO: 44)
        CDR2: AITWSSGRIDYADSVKG (SEQ ID NO: 45)
        CDR3: DRRPRSTGRSGTGSPSTYDY,
``` and
a second ISVD (b) comprising the following CDR sequences:

```
                                    (SEQ ID NO: 49)
        CDR1: INAMG (SEQ ID NO: 47)
        CDR2: AVSSGGSTYYVDSVKG (SEQ ID NO: 48)
        CDR3: ETGPYGPPKRDY.
```

This specific combination of CDR sequences is, for example, contained in the LRP5 antagonist termed LRP5#9 herein below.

The terms "first" and "second" with respect to such ISVDs or domains in general, as used herein, is solely intended to indicate that these domains are two different domains (as they at least include different CDR sequences). Thus, these terms shall not be understood to refer to the exact order or sequence of the domains within such polypeptide chain. In other words, the above ISVDs (a) and (b) may either be arranged in the order (a)-(b) or in the order (b)-(a) within the polypeptides described herein.

Specifically, the ISVDs of the polypeptides described herein (e.g. ISVDs comprising the CDR sequences as defined above) are VHH domains, preferably humanized VHH domains.

In some embodiments of the invention, the LRP5 antagonist comprises a polypeptide with a first ISVD (a) and a second ISVD (b), said first ISVD comprising a VHH domain with a sequence selected from the group consisting of SEQ ID NO:50, SEQ ID NO:51 and SEQ ID NO:62, and said second ISVD comprising a VHH domain with a sequence selected from the group consisting of SEQ ID NO:52, SEQ ID NO:53 and SEQ ID NO:61.

In some embodiments, the first ISVD comprises the sequence of SEQ ID NO:50 and the second ISVD comprises the sequence of SEQ ID NO:52 (LRP5#1).

In some embodiments of the invention, the first ISVD of the LRP5 antagonist comprises the sequence of SEQ ID NO:50 and the second ISVD of the LRP5 antagonist comprises the sequence of SEQ ID NO:61 (LRP5#2).

In some embodiments, the first ISVD comprises the sequence of SEQ ID NO:62 and the second ISVD comprises the sequence of SEQ ID NO:52 (LRP5#3).

In some embodiments, the first ISVD comprises the sequence of SEQ ID NO:62 and the second ISVD comprises the sequence of SEQ ID NO:61 (LRP5#4).

In some embodiments, the first ISVD comprises the sequence of SEQ ID NO:50 and the second ISVD comprises the sequence of SEQ ID NO:53 (LRP5#5).

In some embodiments, the first ISVD comprises the sequence of SEQ ID NO:62, and the second ISVD comprises the sequence of SEQ ID NO:53 (LRP5#6).

In some embodiments of the invention, the first ISVG comprises the sequence of SEQ ID NO:51 and the second ISVD comprises the sequence of SEQ ID NO:52 (LRP5#7).

In some embodiments, the first ISVD comprises the sequence of SEQ ID NO:51 and the second ISVD comprises the sequence of SEQ ID NO:61 (LRP5#8).

In some embodiments, the first ISVD comprises the sequence of SEQ ID NO:51 and the second ISVD comprises the sequence of SEQ ID NO:53 (LRP5#9).

In preferred embodiments of the invention, the LRP5 antagonist is any of one LRP5#2, LRP5#6 or LRP5#7 as defined by the CDR and/or VHH sequences above.

According to a preferred aspect of the invention, the LRP5 antagonist comprises a polypeptide with a first (a) and a second (b) LRP5 binding ISVD and a third ISVD (c). Preferably, the LRP5 antagonist comprises a first and second ISVD as defined by the CDR sequences above and a third ISVD, which directly or indirectly links the first and second ISVD. In some embodiments, the first ISVD is covalently linked via a peptide linker to the third ISVD which is covalently linked to the second ISVD via a peptide linker. The two linkers can be identical or different linkers. Also encompassed is that only one linker is present. The terms "first" and "second", as noted above, do not indicate their position within the polypeptide, thus from N to C terminus the ISVD sequences within the polypeptide can be arranged either in the order ISVDs (a)-(c)-(b), (a)-[linker]-(c)-[linker]-(b), (b)-(c)-(a), (b)-[linker]-(c)-[linker]-(a), (a)-[linker]-(c)-(b), (a)-(c)-[linker]-(b), (b)-[linker]-(c)-(a), (b)-(c)-[linker]-(a).

Preferably, the third ISVD (c) is an albumin binding ISVD. A non-limiting example of such an albumin binding ISVD is the Alb11 domain, comprising the following CDRs:

```
                                       (=SEQ ID NO: 54)
    CDR(Alb11)1: SFGMS (=SEQ ID NO: 55)
    CDR(Alb11)2: SISGSGSDTLYADSVKG (=SEQ ID NO: 56)
    CDR(Alb11)3: GGSLSR
```

This results in a group of preferred LRP5 antagonists having the following structure:
FR(a)1-CDR(a)1-FR(a)2-CDR(a)2-FR(a)3-CDR(a)3-FR(a)4-[optional linker peptide]-FR(A1b11)1-CDR(A1b11)1-FR(A1b11)2-CDR(A1b11)2-FR(A1b11)3-CDR(A1b11)3-FR(A1b11)4-[optional linker peptide]-FR(b)1-CDR(b)1-FR(b)2-CDR(b)2-FR(b)3-CDR(b)3-FR(b)4, preferably wherein the CDRs comprise the sequences as set out above.

Again, the order of the three ISVDs (a), (b), and Alb11 is not fixed but polypeptides in which the above domains are arranged in the order:
(b)-Alb11-(a)
shall be encompassed as well. Furthermore, polypeptides having the Alb11 domain at the N- or C-terminal end of the polypeptide (e.g. Alb11-(a)-(b), Alb11-(b)-(a), (a)-(b)-Alb11, or (b)-(a)-Alb11) shall also be encompassed by the invention.

In some embodiments of the invention, the LRP5 antagonist comprises a polypeptide comprising
a first ISVD comprising the following CDR sequences:

```
                                       (SEQ ID NO: 40)
    CDR1: TYVMG (SEQ ID NO: 41)
    CDR2: AISWSGGSTYYADSVKG (SEQ ID NO: 42)
    CDR3: SRGTSTPSRASGVSRYDY,
``` a second ISVD comprising the following CDR sequences:

```
                                       (SEQ ID NO: 46)
    CDR1: IGAMG (SEQ ID NO: 47)
    CDR2: AVSSGGSTYYVDSVKG (SEQ ID NO: 48)
    CDR3: ETGPYGPPKRDY,
``` and
an albumin binding ISVD (a third ISVD) comprising the following CDR sequences:

```
                                       (SEQ ID NO: 54)
    CDR1: SFGMS (SEQ ID NO: 55)
    CDR2: SISGSGSDTLYADSVKG (SEQ ID NO: 56)
    CDR3: GGSLSR.
```

This specific combination of CDR sequences is, for example, contained in the LRP5 antagonists termed LRP5#1, LRP5#2, LRP5#3, and LRP5#4 herein below.

In some embodiments of the invention, the LRP5 antagonist comprises a polypeptide comprising a first ISVD comprising the following CDR sequences:

```
                                  (SEQ ID NO: 40)
CDR1: TYVMG
                                  (SEQ ID NO: 41)
CDR2: AISWSGGSTYYADSVKG
                                  (SEQ ID NO: 42)
CDR3: SRGTSTPSRASGVSRYDY,
``` a second ISVD comprising the following CDR sequences:

```
                                  (SEQ ID NO: 49)
CDR1: INAMG
                                  (SEQ ID NO: 47)
CDR2: AVSSGGSTYYVDSVKG
                                  (SEQ ID NO: 48)
CDR3: ETGPYGPPKRDY,
``` and an albumin binding ISVD comprising the following CDR sequences:

```
                                  (SEQ ID NO: 54)
CDR1: SFGMS
                                  (SEQ ID NO: 55)
CDR2: SISGSGSDTLYADSVKG
                                  (SEQ ID NO: 56)
CDR3: GGSLSR.
```

This specific combination of CDR sequences is, for example, contained in the LRP5 antagonists termed LRP5#5 and LRP5#6 herein below.

In some embodiments of the invention, the LRP5 antagonist comprises a polypeptide comprising a first ISVD comprising the following CDR sequences:

```
                                  (SEQ ID NO: 43)
CDR1: RYAVA
                                  (SEQ ID NO: 44)
CDR2: AITWSSGRIDYADSVKG
                                  (SEQ ID NO: 45)
CDR3: DRRPRSTGRSGTGSPSTYDY,
``` a second ISVD with the following CDR sequences:

```
                                  (SEQ ID NO: 46)
CDR1: IGAMG
                                  (SEQ ID NO: 47)
CDR2: AVSSGGSTYYVDSVKG
                                  (SEQ ID NO: 48)
CDR3: ETGPYGPPKRDY,
``` and an albumin binding ISVD comprising the following CDR sequences:

```
                                  (SEQ ID NO: 54)
CDR1: SFGMS
                                  (SEQ ID NO: 55)
CDR2: SISGSGSDTLYADSVKG
                                  (SEQ ID NO: 56)
CDR3: GGSLSR.
```

This specific combination of CDR sequences is, for example, contained in the LRP5 antagonists termed LRP5#7 and LRP5#8 herein below.

In some embodiments of the invention, the LRP5 antagonist comprises a polypeptide comprising a first ISVD comprising the following CDR sequences:

```
                                  (SEQ ID NO: 43)
CDR1: RYAVA
                                  (SEQ ID NO: 44)
CDR2: AITWSSGRIDYADSVKG
                                  (SEQ ID NO: 45)
CDR3: DRRPRSTGRSGTGSPSTYDY,
``` a second ISVD comprising the following CDR sequences:

```
                                  (SEQ ID NO: 49)
CDR1: INAMG
                                  (SEQ ID NO: 47)
CDR2: AVSSGGSTYYVDSVKG
                                  (SEQ ID NO: 48)
CDR3: ETGPYGPPKRDY,
``` and an albumin binding ISVD comprising the following CDR sequences:

```
                                  (SEQ ID NO: 54)
CDR1: SFGMS
                                  (SEQ ID NO: 55)
CDR2: SISGSGSDTLYADSVKG
                                  (SEQ ID NO: 56)
CDR3: GGSLSR.
```

This specific combination of CDR sequences is, for example, contained in the LRP5 antagonist termed LRP5#9 herein below.

In some embodiments, the ISVDs as defined by their CDR sequences in the above LRP5 antagonists are arranged such that the albumin binding ISVD directly or indirectly (e.g. via (a) linker peptide(s)) links the first and the second ISVD.

In preferred embodiments, the sequence of the above-mentioned Alb11 ISVD is as follows:

```
EVQLVESGGGLVQPGNSLRLSCAASGFTFSSFGMSWVRQAPGKGLE
WVSSISGSGSDTLYADSVKGRFTISRDNAKTTLYLQMNSLRPEDTA
VYYCTIGGSLSRSSQGTLVTVSS
(=Alb11 domain; =SEQ ID NO: 60)
```

The CDR sequences mentioned above are summarized in Tables 1A, 1B, and 10:

TABLE 1A

CDR sequences of ISVDs interfering with Wnt3a signaling:

|  | F0129097A08 | F0129093A02 |
|---|---|---|
| CDR1 | TYVMG (SEQ ID NO: 40) | RYAVA (SEQ ID NO: 43) |
| CDR2 | AISWSGGSTYYADSVKG (SEQ ID NO: 41) | AITWSSGRIDYADSVKG (SEQ ID NO: 44) |
| CDR3 | SRGTSTPSRASGVSRYDY (SEQ ID NO: 42) | DRRPRSTGRSGTGSPSTYDY (SEQ ID NO: 45) |

TABLE 1B

CDR sequences of ISVDs interfering with Wnt1 signaling:

|  | F012904 6C10(E1A, N32G) | F012904 6C10 |
|---|---|---|
| CDR1 | IGAMG (SEQ ID NO: 46) | INAMG (SEQ ID NO: 49) |
| CDR2 | AVSSGGSTYYVDSVKG (SEQ ID NO: 47) | AVSSGGSTYYVDSVKG (SEQ ID NO: 47) |
| CDR3 | ETGPYGPPKRDY (SEQ ID NO: 48) | ETGPYGPPKRDY (SEQ ID NO: 48) |

TABLE 1C

CDR sequences of ISVD binding to serum albumin (Alb11 domain):

|  | Alb11 domain |
|---|---|
| CDR1 | SFGMS (SEQ ID NO: 54) |
| CDR2 | SISGSGSDTLYADSVKG (SEQ ID NO: 55) |
| CDR3 | GGSLSR (SEQ ID NO: 56) |

Three preferred LRP5 antagonists described herein are as follows:

First preferred LRP5 antagonist (LRP5#6): Polypeptides comprising
- a first (LRP5 binding) ISVD comprising the amino acid sequence as shown in SEQ ID NO:62;
- an albumin binding ISVD comprising the amino acid sequence as shown in SEQ ID NO:60;
- a second (LRP5 binding) ISVD comprising the amino acid sequence as shown in SEQ ID NO:53;

either in this order, or the order of the above three domains being changed.

Second preferred LRP5 antagonist (LRP5#7): Polypeptides comprising
- a first (LRP5 binding) ISVD comprising the amino acid sequence as shown in SEQ ID NO:51;
- an albumin binding ISVD comprising the amino acid sequence as shown in SEQ ID NO:60;
- a second (LRP5 binding) ISVD comprising the amino acid sequence as shown in SEQ ID NO:52;

either in this order, or the order of the above three domains being changed.

Third preferred LRP5 antagonist (LRP5#2): Polypeptides comprising
- a first (LRP5 binding) ISVD comprising the amino acid sequence as shown in SEQ ID NO:50;
- an albumin binding ISVD comprising the amino acid sequence as shown in SEQ ID NO:60;
- a second (LRP5 binding) ISVD comprising the amino acid sequence as shown in SEQ ID NO:61;

either in this order, or the order of the above three domains being changed.

In even more specifically preferred embodiments, the albumin binding ISVD is located between the two LRP5 binding ISVDs.

The sequences of the VHHs mentioned above are summarized in Tables 2A, 2B, and 2C:

TABLE 2A

VHH sequences of ISVDs interfering with Wnt3a signaling:

| SEQ ID NO: | VHH sequences |
|---|---|
| F0129097A08 (E1A, V23A) SEQ ID NO: 50 | AVQLVESGGGLVQPGGSLRLSCAASGRTFST YVMGWFRQAPGKEREFVAAISWSGGSTYYAD SVKGRFTISRDNSKNTVYLQMNSLRPEDTAV YYCAASRGTSTPSRASGVSRYDYWGQGTLVT VSS |
| F0129093A02 SEQ ID NO: 51 | EVQLVESGGGLVQPGGSLRLSCAASGLTFSR YAVAWFRQAPGKEREFVAAITWSSGRIDYAD SVKGRFTISRDNSKNTVYLQMNSLRPEDTAV YYCAADRRPRSTGRSGTGSPSTYDYWGQGTL VTVSSA (SEQ ID NO: 12) |
| F0129097A08 SEQ ID NO: 62 | EVQLVESGGGLVQPGGSLRLSCVASGRTFST YVMGWFRQAPGKEREFVAAISWSGGSTYYAD SVKGRFTISRDNSKNTVYLQMNSLRPEDTAV YYCAASRGTSTPSRASGVSRYDYWGQGTLVT VSS |

TABLE 2B

VHH sequences of ISVDs interfering with Wnt1 signaling:

| SEQ ID NO: | VHH sequences |
|---|---|
| F0129046C10 (E1A, N32G) SEQ ID NO: 52 | AVQLVESGGGLVQPGGSLRLSCAASGSIFRI GAMGWYRQAPGKQRELVAAVSSGGSTYYVDS VKGRFTISRDNSKNTVYLQMNSLRPEDTAVY YCNRETGPYGPPKRDYWGQGTLVTVSS |
| F0129046C10 SEQ ID NO: 53 | EVQLVESGGGLVQPGGSLRLSCAASGSIFRI NAMGWYRQAPGKQRELVAAVSSGGSTYYVDS VKGRFTISRDNSKNTVYLQMNSLRPEDTAVY YCNRETGPYGPPKRDYWGQGTLVTVSS |
| F0129046C10 (N32G) SEQ ID NO: 61 | EVQLVESGGGLVQPGGSLRLSCAASGSIFRI GAMGWYRQAPGKQRELVAAVSSGGSTYYVDS VKGRFTISRDNSKNTVYLQMNSLRPEDTAVY YCNRETGPYGPPKRDYWGQGTLVTVSSA |

TABLE 2C

Sequence of ISVD binding to serum albumin (Alb11 domain):

| SEQ ID NO: | VHH sequences |
|---|---|
| Alb11 SEQ ID NO: 60 | EVQLVESGGGLVQPGNSLRLSCAASGFT FSSFGMSWVRQAPGKGLEWVSSISGSGS DTLYADSVKGRFTISRDNAKTTLYLQMN SLRPEDTAVYYCTIGGSLSRSSQGTLVT VSS |

In preferred embodiments of the invention, the LRP5 antagonist comprises a sequence selected from SEQ ID NOs: 57, 58 and 59 (these preferred LRP5 antagonist are also referred to herein as LRP5#6, LRP5#7, and LRP5#2, respectively) wherein the exact amino acid sequences can be taken from Table 2D below:

TABLE 2D

| SEQ ID NO: | Amino Acid Sequence (CDR sequences underlined) |
|---|---|
| SEQ ID NO: 57 | EVQLVESGGGLVQPGGSLRLSCVASGRTFS<u>TYVMG</u>WFRQAPGKEREFVA<u>AISWSGGSTYYADSVKG</u>RFTISRDNSKNTVYLQMNSLRPEDTAVYYCAA<u>SRGTSTPSRASGVSRYDY</u>WGQGTLVTVSSGGGGSGGGGSGGGGSGGGGSGGGGSGGGGSGGGGSEVQLVESGGGLVQPGNSLRLSCAASGFTFS<u>SFGMS</u>WVRQAPGKGLEWVS<u>SISGSGSDTLYADSVKG</u>RFTISRDNAKTTLYLQMNSLRPEDTAVYYCTI<u>GGSLSR</u>SSQGTLVTVSSGGGGSGGGGSGGGGSGGGGSGGGGSGGGGSEVQLVESGGGLVQPGGSLRLSCAASGSIFR<u>INAMG</u>WYRQAPGKQRELVA<u>AVSSGGSTYYVDSVKG</u>RFTISRDNSKNTVYLQMNSLRPEDTAVYYCNR<u>ETGPYGPPKRDY</u>WGQGTLVTVSS |
| SEQ ID NO: 58 | AVQLVESGGGLVQPGGSLRLSCAASGSIFR<u>IGAMGW</u>YRQAPGKQRELVA<u>AVSSGGSTYYVDSVKG</u>RFTISRDNSKNTVYLQMNSLRPEDTAVYYCNR<u>ETGPYGPPKRDY</u>WGQGTLVTVSSGGGGSGGGGSGGGGSGGGGSGGGGSGGGGSGGGGSGLVQPGNSLRLSCAASGFTFS<u>SFGMS</u>WVRQAPGKGLEWVS<u>SISGSGSDTLYADSVKG</u>RFTISRDNAKTTLYLQMNSLRPEDTAVYYCTI<u>GGSLSR</u>SSQGTLVTVSSGGGGSGGGGSGGGGSGGGGSGGGGSGGGGSGGGGSEVQLVESGGGLVQPGGSLRLSCAASGLTFS<u>RYAVAW</u>FRQAPGKEREFVA<u>AITWSSGRIDYADSV</u>KGRFTISRDNSKNTVYLQMNSLRPEDTAVYYCAA<u>DRRPRSTGRSGTGSPSTYDY</u>WGQGTLVTVSSA |
| SEQ ID NO: 59 | AVQLVESGGGLVQPGGSLRLSCAASGRTFS<u>TYVMG</u>WFRQAPGKEREFVA<u>AISWSGGSTYYADSVKG</u>RFTISRDNSKNTVYLQMNSLRPEDTAVYYCAA<u>SRGTSTPSRASGVSRYDY</u>WGQGTLVTVSSGGGGSGGGGSGGGGSGGGGSGGGGSGGGGSGGGGSEVQLVESGGGLVQPGNSLRLSCAASGFTFS<u>SFGMS</u>WVRQAPGKGLEWVS<u>SISGSGSDTLYADSVKG</u>RFTISRDNAKTTLYLQMNSLRPEDTAVYYCTI<u>GGSLSR</u>SSQGTLVTVSSGGGGSGGGGSGGGGSGGGGSGGGGSGGGGSEVQLVESGGGLVQPGGSLRLSCAASGSIFR<u>IGAMGW</u>YRQAPGKQRELVA<u>AVSSGGSTYYVDSVKG</u>RFTISRDNSKNTVYLQMNSLRPEDTAVYYCNR<u>ETGPYGPPKRDY</u>WGQGTLVTVSSA |

Manufacture and therapeutic use of the aforementioned LRP5 antagonists is disclosed in WO2018/220080A1. In particular, this document provides a sufficient disclosure of the method of preparing the LRP5 antagonists used in the present invention.

Anti-PD-1 Antibody

An anti-PD-1 antibody (also referred to as "PD-1 antibody" herein) within the meaning of this invention and all of its embodiments is a compound that inhibits the interaction of PD-1 with its ligand(s). Preferably, the anti-PD-1 antibody is a humanized or fully human anti-PD-1 antibody. Any one of these antibodies may be a recombinant human antibody.

The PD-1 gene encodes a 55 kDa type I transmembrane protein that is part of the Ig gene superfamily (Agata et al. (1996) Int Immunol. 8:765-72). The complete PD-1 sequence can be found under GenBank Accession No. U64863. Although structurally similar to CTLA-4, PD-1 lacks the MYPPY motif (SEQ ID NO:39) that is important for B7-1 and B7-2 binding.

PD-1 is an inhibitory member of the extended CD28/CTLA-4 family of T cell regulators. Other members of the CD28 family include CD28, CTLA-4, ICOS and BTLA. PD-1 is suggested to exist as a monomer, lacking the unpaired cysteine residue characteristic of other CD28 family members. PD-1 is expressed on activated B cells, T cells, and monocytes (Okazaki et al. (2002) Curr Opin Immunol 14:391779-82; Bennett et al. (2003) J. Immunol. 170:711-8). Two ligands for PD-1 have been identified, PD-L1 (B7-H1) and PD-L2 (B7-DC), that have been shown to downregulate T cell activation upon binding to PD-1 (Freeman et al. (2000) J. Exp. Med. 192:1027-34; Carter et al. (2002) Eur. J. Immunol. 32:634-43). Both PD-L1 and PD-L2 are B7 homologs that bind to PD-1. PD-L1 is abundant in a variety of human cancers (Dong et al. (2002) Nat. Med. 8:787-9).

PD-1 is known as an immuno-inhibitory protein that negatively regulates TCR signals (Ishida, Y. et al. (1992) EMBO J. 11:3887-3895; Blank, C. et al. (2006) Immunol. Immunother. 56(6):739-745). The interaction between PD-1 and PD-L1 can act as an immune checkpoint, which can lead to, e.g., a decrease in tumor infiltrating lymphocytes, a decrease in T-cell receptor mediated proliferation, and/or immuno-evasion by cancerous cells (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1 or PD-L2; the effect is additive when the interaction of PD-1 with both PD-L1 and PD-L2 is blocked (Iwai et al. (2002) Proc. Nat'l. Acad. Sci USA 99:12293-7; Brown et al. (2003) J. Immunol. 170:1257-66).

In one aspect of the invention, the anti-PD-1 antibody is any one of antibodies PD1-1, PD1-2, PD1-3, PD1-4 and PD1-5 defined by the sequences as shown in Table 3 by way of the SEQ ID numbers, wherein VH denotes the heavy chain variable domain, VL denotes the light chain variable domain, HC denotes the (full length) heavy chain and LC denotes the (full length) light chain:

TABLE 3

SEQ ID NOs of the CDR, VH, VL, HC and LC sequences

| anti-PD1 antibody | CDR sequences | VH sequences | VL sequences | HC sequences | LC sequences |
|---|---|---|---|---|---|
| PD1-1 | 1-6 | 19 | 20 | 29 | 30 |
| PD1-2 | 7-12 | 21 | 22 | 31 | 32 |
| PD1-3 | 13-18 | 23 | 24 | 33 | 34 |
| PD1-4 | 13-18 | 25 | 26 | 35 | 36 |
| PD1-5 | 13-18 | 27 | 28 | 37 | 38 | and wherein the amino acid sequences (and sequence names) of the SEQ ID numbers are as shown in Table 4:

TABLE 4

| SEQ ID NO: | Sequence name | Amino acid sequence |
|---|---|---|
| 1 | PD1-1HCDR1 | GFTFSASAMS |
| 2 | PD1-1HCDR2 | YISGGGGDTYYSSSVKG |

TABLE 4-continued

| SEQ ID NO: | Sequence name | Amino acid sequence |
|---|---|---|
| 3 | PD1-1HCDR3 | HSNVNYYAMDY |
| 4 | PD1-1LCDR1 | RASENIDTSGISFMN |
| 5 | PD1-1LCDR2 | VASNQGS |
| 6 | PD1-1LCDR3 | QQSKEVPWT |
| 7 | PD1-2HCDR1 | GFTFSASAMS |
| 8 | PD1-2HCDR2 | YISGGGGDTYYSSSVKG |
| 9 | PD1-2HCDR3 | HSNPNYYAMDY |
| 10 | PD1-2LCDR1 | RASENIDTSGISFMN |
| 11 | PD1-2LCDR2 | VASNQGS |
| 12 | PD1-2LCDR3 | QQSKEVPWT |
| 13 | PD1-3HCDR1 | GFTFSKSAMS |
| 14 | PD1-3HCDR2 | YISGGGGDTYYSSSVKG |
| 15 | PD1-3HCDR3 | HSNVNYYAMDY |
| 16 | PD1-3LCDR1 | RASENIDVSGISFMN |
| 17 | PD1-3LCDR2 | VASNQGS |
| 18 | PD1-3LCDR3 | QQSKEVPWT |
| 19 | PD1VH1 | EVMLVESGGGLVQPGGSLRLSCTASGFTFSASAMSWVRQAPGKGLEWV AYISGGGGDTYYSSSVKGRFTISRDNAKNSLYLQMNSLRAEDTAVYYC ARHSNVNYYAMDYWGQGTLVTVSS |
| 20 | PD1VL1 | EIVLTQSPATLSLSPGERATMSCRASENIDTSGISFMNWYQQKPGQAP KLLIYVASNQGSGIPARFSGSGSGTDFTLTISRLEPED FAVYYCQQSKEVPWTFGQGTKLEIK |
| 21 | PD1VH2 | EVMLVESGGGLVQPGGSLRLSCTASGFTFSASAMSWVRQAPGKGLEWV AYISGGGGDTYYSSSVKGRFTISRDNAKNSLYLQMNSLRAEDTAVYYC ARHSNPNYYAMDYWGQGTLVTVSS |
| 22 | PD1VL2 | EIVLTQSPATLSLSPGERATMSCRASENIDTSGISFMNWYQQ KPGQAPKLLIYVASNQGSGIPARFSGSGSGTDFTLTISRLEPED FAVYYCQQSKEVPWTFGQGTKLEIK |
| 23 | PD1VH3 | EVMLVESGGGLVQPGGSLRLSCTASGFTFSKSAMSWVRQAP GKGLEWVAYISGGGGDTYYSSSVKGRFTISRDNAKNSLYLQM NSLRAEDTAVYYCARHSNVNYYAMDYWGQGTLVTVSS |
| 24 | PD1VL3 | EIVLTQSPATLSLSPGERATMSCRASENIDVSGISFMNWYQQ KPGQAPKLLIYVASNQGSGIPARFSGSGSGTDFTLTISRLEPED FAVYYCQQSKEVPWTFGQGTKLEIK |
| 25 | PD1VH4 | EVMLVESGGGLVQPGGSLRLSCTASGFTFSKSAMSWVRQAP GKGLEWVAYISGGGGDTYYSSSVKGRFTISRDNAKNSLYLQM NSLRAEDTAVYYCARHSNVNYYAMDYWGQGTLVTVSS |
| 26 | PD1VL4 | EIVLTQSPATLSLSPGERATMSCRASENIDVSGISFMNWYQQ KPGQAPKLLIYVASNQGSGIPARFSGSGSGTDFTLTISRLEPED FAVYYCQQSKEVPWTFGQGTKLEIK |
| 27 | PD1VH5 | EVMLVESGGGLVQPGGSLRLSCTASGFTFSKSAMSWVRQAP GKGLEWVAYISGGGGDTYYSSSVKGRFTISRDNAKNSLYLQM NSLRAEDTAVYYCARHSNVNYYAMDYWGQGTLVTVSS |
| 28 | PD1VL5 | EIVLTQSPATLSLSPGERATMSCRASENIDVSGISFMNWYQQ KPGQAPKLLIYVASNQGSGIPARFSGSGSGTDFTLTISRLEPED FAVYYCQQSKEVPWTFGQGTKLEIK |
| 29 | PD1HC1 | EVMLVESGGGLVQPGGSLRLSCTASGFTFSASAMSWVRQAP GKGLEWVAYISGGGGDTYYSSSVKGRFTISRDNAKNSLYLQM NSLRAEDTAVYYCARHSNVNYYAMDYWGQGTLVTVSSASTK GPSVFPLAPCSRSTSESTAALGCLVKDYFPEPVTVSWNSGALT |

TABLE 4-continued

| SEQ ID NO: | Sequence name | Amino acid sequence |
|---|---|---|
| | | SGVHTFPAVLQSSGLYSLSSVVTVPSSSLGTKTYTCNVDHKPS NTKVDKRVESKYGPPCPPCPAPEFLGGPSVFLFPPKPKDTLMI SRTPEVTCVVVDVSQEDPEVQFNWYVDGVEVHNAKTKPREE QFNSTYRVVSVLTVLHQDWLNGKEYKCKVSNKGLPSSIEKTIS KAKGQPREPQVYTLPPSQEEMTKNQVSLTCLVKGFYPSDIAV EWESNGQPENNYKTTPPVLDSDGSFFLYSRLTVDKSRWQEG NVFSCSVMHEALHNHYTQKSLSLSLG |
| 30 | PD1LC1 | EIVLTQSPATLSLSPGERATMSCRASENIDTSGISFMNWYQQ KPGQAPKLLIYVASNQGSGIPARFSGSGSGTDFTLTISRLEPED FAVYYCQQSKEVPWTFGQGTKLEIKRTVAAPSVFIFPPSDEQL KSGTASVVCLLNNFYPREAKVQWKVDNALQSGNSQESVTEQ DSKDSTYSLSSTLTLSKADYEKHKVYACEVTHQGLSSPVTKSFN RGEC |
| 31 | PD1HC2 | EVMLVESGGGLVQPGGSLRLSCTASGFTFSASAMSWVRQAP GKGLEWVAYISGGGGDTYYSSSVKGRFTISRDNAKNSLYLQM NSLRAEDTAVYYCARHSNPNYYAMDYWGQGTLVTVSSASTK GPSVFPLAPCSRSTSESTAALGCLVKDYFPEPVTVSWNSGALT SGVHTFPAVLQSSGLYSLSSVVTVPSSSLGTKTYTCNVDHKPS NTKVDKRVESKYGPPCPPCPAPEFLGGPSVFLFPPKPKDTLMI SRTPEVTCVVVDVSQEDPEVQFNWYVDGVEVHNAKTKPREE QFNSTYRVVSVLTVLHQDWLNGKEYKCKVSNKGLPSSIEKTIS KAKGQPREPQVYTLPPSQEEMTKNQVSLTCLVKGFYPSDIAV EWESNGQPENNYKTTPPVLDSDGSFFLYSRLTVDKSRWQEG NVFSCSVMHEALHNHYTQKSLSLSLG |
| 32 | PD1LC2 | EIVLTQSPATLSLSPGERATMSCRASENIDTSGISFMNWYQQ KPGQAPKLLIYVASNQGSGIPARFSGSGSGTDFTLTISRLEPED FAVYYCQQSKEVPWTFGQGTKLEIKRTVAAPSVFIFPPSDEQL KSGTASVVCLLNNFYPREAKVQWKVDNALQSGNSQESVTEQ DSKDSTYSLSSTLTLSKADYEKHKVYACEVTHQGLSSPVTKSFN RGEC |
| 33 | PD1HC3 | EVMLVESGGGLVQPGGSLRLSCTASGFTFSKSAMSWVRQAP GKGLEWVAYISGGGGDTYYSSSVKGRFTISRDNAKNSLYLQM NSLRAEDTAVYYCARHSNVNYYAMDYWGQGTLVTVSSASTK GPSVFPLAPCSRSTSESTAALGCLVKDYFPEPVTVSWNSGALT SGVHTFPAVLQSSGLYSLSSVVTVPSSSLGTKTYTCNVDHKPS NTKVDKRVESKYGPPCPPCPAPEFLGGPSVFLFPPKPKDTLMI SRTPEVTCVVVDVSQEDPEVQFNWYVDGVEVHNAKTKPREE QFNSTYRVVSVLTVLHQDWLNGKEYKCKVSNKGLPSSIEKTIS KAKGQPREPQVYTLPPSQEEMTKNQVSLTCLVKGFYPSDIAV EWESNGQPENNYKTTPPVLDSDGSFFLYSRLTVDKSRWQEG NVFSCSVMHEALHNHYTQKSLSLSLG |
| 34 | PD1LC3 | EIVLTQSPATLSLSPGERATMSCRASENIDVSGISFMNWYQQ KPGQAPKLLIYVASNQGSGIPARFSGSGSGTDFTLTISRLEPED FAVYYCQQSKEVPWTFGQGTKLEIKRTVAAPSVFIFPPSDEQL KSGTASVVCLLNNFYPREAKVQWKVDNALQSGNSQESVTEQ DSKDSTYSLSSTLTLSKADYEKHKVYACEVTHQGLSSPVTKSFN RGEC |
| 35 | PD1HC4 | EVMLVESGGGLVQPGGSLRLSCTASGFTFSKSAMSWVRQAP GKGLEWVAYISGGGGDTYYSSSVKGRFTISRDNAKNSLYLQM NSLRAEDTAVYYCARHSNVNYYAMDYWGQGTLVTVSSASTK GPSVFPLAPCSRSTSESTAALGCLVKDYFPEPVTVSWNSGALT SGVHTFPAVLQSSGLYSLSSVVTVPSSSLGTKTYTCNVDHKPS NTKVDKRVESKYGPPCPPCPAPEFLGGPSVFLFPPKPKDTLMI SRTPEVTCVVVDVSQEDPEVQFNWYVDGVEVHNAKTKPREE QFNSTYRVVSVLTVLHQDWLNGKEYKCKVSNKGLPSSIEKTIS KAKGQPREPQVYTLPPSQEEMTKNQVSLTCLVKGFYPSDIAV EWESNGQPENNYKTTPPVLDSDGSFFLYSRLTVDKSRWQEG NVFSCSVMHEALHNHYTQKSLSLSLG |
| 36 | PD1LC4 | EIVLTQSPATLSLSPGERATMSCRASENIDVSGISFMNWYQQ KPGQAPKLLIYVASNQGSGIPARFSGSGSGTDFTLTISRLEPED FAVYYCQQSKEVPWTFGQGTKLEIKRTVAAPSVFIFPPSDEQL KSGTASVVCLLNNFYPREAKVQWKVDNALQSGNSQESVTEQ DSKDSTYSLSSTLTLSKADYEKHKVYACEVTHQGLSSPVTKSFN RGEC |
| 37 | PD1HC5 | EVMLVESGGGLVQPGGSLRLSCTASGFTFSKSAMSWVRQAP GKGLEWVAYISGGGGDTYYSSSVKGRFTISRDNAKNSLYLQM NSLRAEDTAVYYCARHSNVNYYAMDYWGQGTLVTVSSASTK GPSVFPLAPCSRSTSESTAALGCLVKDYFPEPVTVSWNSGALT SGVHTFPAVLQSSGLYSLSSVVTVPSSSLGTKTYTCNVDHKPS |

TABLE 4-continued

| SEQ ID NO: | Sequence name | Amino acid sequence |
|---|---|---|
| | | NTKVDKRVESKYGPPCPPCPAPEFLGGPSVFLFPPKPKDTLMI SRTPEVTCVVVDVSQEDPEVQFNWYVDGVEVHNAKTKPREE QFNSTYRVVSVLTVLHQDWLNGKEYKCKVSNKGLPSSIEKTIS KAKGQPREPQVYTLPPSQEEMTKNQVSLTCLVKGFYPSDIAV EWESNGQPENNYKTTPPVLDSDGSFFLYSRLTVDKSRWQEG NVFSCSVMHEALHNHYTQKSLSLSLG |
| 38 | PD1LC5 | EIVLTQSPATLSLSPGERATMSCRASENIDVSGISFMNWYQQ KPGQAPKLLIYVASNQGSGIPARFSGSGSGTDFTLTISRLEPED FAVYYCQQSKEVPWTFGQGTKLEIKRTVAAPSVFIFPPSDEQL KSGTASVVCLLNNFYPREAKVQWKVDNALQSGNSQESVTEQ DSKDSTYSLSSTLTLSKADYEKHKVYACEVTHQGLSSPVTKSFN RGEC |

Specifically, an anti-PD-1 antibody molecule described herein comprises:
(a) heavy chain CDRs comprising the amino acid sequence of SEQ ID NO:1 (HCDR1), SEQ ID NO:2 (HCDR2) and SEQ ID NO:3 (HCDR3) and light chain CDRs comprising the amino acid sequence of SEQ ID NO:4 (LCDR1), SEQ ID NO:5 (LCDR2) and SEQ ID NO:6 (LCDR3); or,
(b) heavy chain CDRs comprising the amino acid sequence of SEQ ID NO:7 (HCDR1), SEQ ID NO:8 (HCDR2) and SEQ ID NO:9 (HCDR3) and light chain CDRs comprising the amino acid sequence of SEQ ID NO:10 (LCDR1), SEQ ID NO:11 (LCDR2) and SEQ ID NO:12 (LCDR3); or
(c) heavy chain CDRs comprising the amino acid sequence of SEQ ID NO:13 (HCDR1), SEQ ID NO:14 (HCDR2) and SEQ ID NO:15 (HCDR3) and light chain CDRs comprising the amino acid sequence of SEQ ID NO:16 (LCDR1), SEQ ID NO:17 (LCDR2) and SEQ ID NO:18 (LCDR3).

In some embodiments, the anti-PD-1 antibody molecule comprises a heavy chain variable domain comprising an amino acid sequence selected from SEQ ID NOs: 19, 21, 23, 25 and 27.

In some embodiments, the anti-PD-1 antibody molecule comprises a light chain variable domain comprising an amino acid sequence selected from SEQ ID NOs: 20, 22, 24, 26 and 28.

In some embodiments, the anti-PD-1 antibody molecule comprises
(a) a heavy chain variable domain comprising the amino acid sequence of SEQ ID NO: 19 and a light chain variable domain comprising the amino acid sequence of SEQ ID NO: 20,
(b) a heavy chain variable domain comprising the amino acid sequence of SEQ ID NO: 21 and a light chain variable domain comprising the amino acid sequence of SEQ ID NO: 22,
(c) a heavy chain variable domain comprising the amino acid sequence of SEQ ID NO: 23 and a light chain variable domain comprising the amino acid sequence of SEQ ID NO: 24,
(d) a heavy chain variable domain comprising the amino acid sequence of SEQ ID NO: 25 and a light chain variable domain comprising the amino acid sequence of SEQ ID NO: 26, or
(e) a heavy chain variable domain comprising the amino acid sequence of SEQ ID NO: 27 and a light chain variable domain comprising the amino acid sequence of SEQ ID NO: 28.

In some embodiments, the anti-PD-1 antibody comprises
(a) a heavy chain comprising the amino acid sequence of SEQ ID NO: 29 and a light chain comprising the amino acid sequence of SEQ ID NO: 30,
(b) a heavy chain comprising the amino acid sequence of SEQ ID NO: 31 and a light chain comprising the amino acid sequence of SEQ ID NO: 32,
(c) a heavy chain comprising the amino acid sequence of SEQ ID NO: 33 and a light chain comprising the amino acid sequence of SEQ ID NO: 34,
(d) a heavy chain comprising the amino acid sequence of SEQ ID NO: 35 and a light chain comprising the amino acid sequence of SEQ ID NO: 36, or
(e) a heavy chain comprising the amino acid sequence of SEQ ID NO: 37 and a light chain comprising the amino acid sequence of SEQ ID NO: 38.

In a preferred embodiment the anti-PD-1 antibody is PD1-1.

In a preferred embodiment the anti-PD-1 antibody is PD1-2.

In a preferred embodiment the anti-PD-1 antibody is PD1-3.

In a preferred embodiment the anti-PD-1 antibody is PD1-4.

In a preferred embodiment the anti-PD-1 antibody is PD1-5.

In one aspect, the invention provides a method of treating and/or preventing a hyperproliferative disease, preferably cancer, comprising administering to a patient in need thereof a therapeutically effective amount of an LRP5 antagonist (e.g. any one of LRP5#1, LRP5#2, LRP5#3, LRP5#4, LRP5#5, LRP5#6, LRP5#7, LRP5#8, LRP5#9 as defined by the CDR and/or VHH sequences of Tables 1a, 1b, 1c, 2a, 2b, 2c) and a therapeutically effective amount of an anti-PD-1 antibody (e.g., any one of PD1-1, PD1-2, PD1-3, PD1-4, PD1-5 as defined by the CDR and/or VH/VL sequences of Tables 3 and 4). In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 29 and a light chain comprising the amino acid sequence of SEQ ID NO: 30. In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 31 and a light chain comprising the amino acid sequence of SEQ ID NO: 32. In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 33 and a light chain comprising the amino acid sequence of SEQ ID NO: 34.

In another aspect the invention provides a combination of an LRP5 antagonist as described herein (e.g. any one of LRP5#1, LRP5#2, LRP5#3, LRP5#4, LRP5#5, LRP5#6, LRP5#7, LRP5#8, LRP5#9 as defined by the CDR and/or VHH sequences of Tables 1a, 1b, 1c, 2a, 2b, 2c) and an anti-PD-1 antibody as described herein (e.g., any one of PD1-1, PD1-2, PD1-3, PD1-4, PD1-5 as defined by the CDR and/or VH/VL sequences of Tables 3 and 4), particularly for use in a method of treating and/or preventing a hyperproliferative disease, preferably cancer, wherein said method comprises that a therapeutically effective amount of the combination is to be administered to a patient in need thereof. In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 29 and a light chain comprising the amino acid sequence of SEQ ID NO: 30. In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 31 and a light chain comprising the amino acid sequence of SEQ ID NO: 32. In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 33 and a light chain comprising the amino acid sequence of SEQ ID NO: 34.

In another aspect the invention refers to an LRP5 antagonist as described herein (e.g. any one of LRP5#1, LRP5#2, LRP5#3, LRP5#4, LRP5#5, LRP5#6, LRP5#7, LRP5#8, LRP5#9 as defined by the CDR and/or VHH sequences of Tables 1a, 1b, 1c, 2a, 2b, 2c) for use in a method of treating and/or preventing a hyperproliferative disease, preferably cancer, wherein said method comprises that a therapeutically effective amount of the LRP5 antagonist in combination with an anti-PD-1 antibody as described herein (e.g., any one of PD1-1, PD1-2, PD1-3, PD1-4, PD1-5 as defined by the CDR and/or VH/VL sequences of Tables 3 and 4) is to be administered to a patient in need thereof. In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 29 and a light chain comprising the amino acid sequence of SEQ ID NO: 30. In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 31 and a light chain comprising the amino acid sequence of SEQ ID NO: 32. In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 33 and a light chain comprising the amino acid sequence of SEQ ID NO: 34.

In another aspect the invention refers to an anti-PD-1 antibody as described herein (e.g., any one of PD1-1, PD1-2, PD1-3, PD1-4, PD1-5 as defined by the CDR and/or VH/VL sequences of Tables 3 and 4) for use in a method of treating and/or preventing a hyperproliferative disease, preferably cancer, wherein said method comprises that a therapeutically effective amount of the anti-PD-1 antibody in combination with an LRP5 antagonist as described herein (e.g. any one of LRP5#1, LRP5#2, LRP5#3, LRP5#4, LRP5#5, LRP5#6, LRP5#7, LRP5#8, LRP5#9 as defined by the CDR and/or VHH sequences of Tables 1a, 1b, 1c, 2a, 2b, 2c) is to be administered to a patient in need thereof. In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 29 and a light chain comprising the amino acid sequence of SEQ ID NO: 30. In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 31 and a light chain comprising the amino acid sequence of SEQ ID NO: 32. In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 33 and a light chain comprising the amino acid sequence of SEQ ID NO: 34.

In another aspect the invention refers to a kit comprising in one or more containers a first pharmaceutical composition or dosage form comprising an LRP5 antagonist as described herein (e.g. any one of LRP5#1, LRP5#2, LRP5#3, LRP5#4, LRP5#5, LRP5#6, LRP5#7, LRP5#8, LRP5#9 as defined by the CDR and/or VHH sequences of Tables 1a, 1b, 1c, 2a, 2b, 2 c), and, optionally, one or more pharmaceutically acceptable carriers, excipients and/or vehicles, and a second pharmaceutical composition or dosage form comprising an anti-PD-1 antibody as described herein (e.g., any one of PD1-1, PD1-2, PD1-3, PD1-4, PD1-5 as defined by the CDR and/or VH/VL sequences of Tables 3 and 4), and, optionally, one or more pharmaceutically acceptable carriers, excipients and/or vehicles;

and optionally a package insert comprising printed instructions.

In preferred embodiments of the kits of the invention, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 29 and a light chain comprising the amino acid sequence of SEQ ID NO: 30. In preferred embodiments of the kits of the invention, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 31 and a light chain comprising the amino acid sequence of SEQ ID NO: 32. In preferred embodiments of the kits of the invention, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 33 and a light chain comprising the amino acid sequence of SEQ ID NO: 34.

Preferably, the package insert comprises printed instructions for simultaneous, concurrent, sequential, successive, alternate or separate use in the treatment and/or prevention of a hyperproliferative disease, in particular cancer, as described herein, in a patient in need thereof.

In another aspect the invention refers to the aforementioned kits for use in a method of treating and/or preventing a hyperproliferative disease, preferably cancer, as described herein.

In another aspect the invention refers to a pharmaceutical composition comprising an LRP5 antagonist as described herein (e.g. any one of LRP5#1, LRP5#2, LRP5#3, LRP5#4, LRP5#5, LRP5#6, LRP5#7, LRP5#8, LRP5#9 as defined by the CDR and/or VHH sequences of Tables 1a, 1b, 1c, 2a, 2b, 2c), an anti-PD-1 antibody as described herein (e.g., any one of PD1-1, PD1-2, PD1-3, PD1-4, PD1-5 as defined by the CDR and/or VH/VL sequences of Tables 3 and 4), and, optionally, one or more pharmaceutically acceptable carriers, excipients and/or vehicles.

In preferred embodiments of the pharmaceutical composition of the invention, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 29 and a light chain comprising the amino acid sequence of SEQ ID NO: 30. In preferred embodiments of the pharmaceutical composition, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 31 and a light chain comprising the amino acid sequence of SEQ ID NO: 32. In preferred embodiments of the pharmaceutical composition, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 33 and a light chain comprising the amino acid sequence of SEQ ID NO: 34.

In another aspect the invention refers to the use of an LRP5 antagonist as described herein (e.g. any one of LRP5#1, LRP5#2, LRP5#3, LRP5#4, LRP5#5, LRP5#6, LRP5#7, LRP5#8, LRP5#9 as defined by the CDR and/or VHH sequences of Tables 1a, 1b, 1c, 2a, 2b, 2c) for preparing a pharmaceutical composition for use in a method of treating and/or preventing a hyperproliferative disease, preferably cancer, as described herein, wherein the LRP5 antagonist is to be used in combination with a PD-1 antibody as described herein (e.g., any one of PD1-1, PD1-2, PD1-3, PD1-4, PD1-5 as defined by the CDR and/or VH/VL sequences of Tables 3 and 4). In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 29 and a light chain comprising the amino acid sequence of SEQ ID NO: 30. In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 31 and a light chain comprising the amino acid sequence of SEQ ID NO: 32. In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 33 and a light chain comprising the amino acid sequence of SEQ ID NO: 34.

In another aspect the invention refers to the use of a PD-1 antibody as described herein (e.g., any one of PD1-1, PD1-2, PD1-3, PD1-4, PD1-5 as defined by the CDR and/or VH/VL sequences of Tables 3 and 4) for preparing a pharmaceutical composition for use in a method of treating and/or preventing a hyperproliferative disease, preferably cancer, as described herein, wherein the PD-1 antagonist is to be used in combination with an LRP5 antagonist as described herein (e.g. any one of LRP5#1, LRP5#2, LRP5#3, LRP5#4, LRP5#5, LRP5#6, LRP5#7, LRP5#8, LRP5#9 as defined by the CDR and/or VHH sequences of Tables 1a, 1b, 1c, 2a, 2b, 2c). In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 29 and a light chain comprising the amino acid sequence of SEQ ID NO: 30. In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 31 and a light chain comprising the amino acid sequence of SEQ ID NO: 32. In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 33 and a light chain comprising the amino acid sequence of SEQ ID NO: 34.

In another aspect the invention refers to the use of an LRP5 antagonist (e.g. any one of LRP5#1, LRP5#2, LRP5#3, LRP5#4, LRP5#5, LRP5#6, LRP5#7, LRP5#8, LRP5#9 as defined by the CDR and/or VHH sequences of Tables 1a, 1b, 1c, 2a, 2b, 2c) and a PD-1 antibody (e.g., any one of PD1-1, PD1-2, PD1-3, PD1-4, PD1-5 as defined by the CDR and/or VH/VL sequences of Tables 3 and 4), for preparing a pharmaceutical composition for use in a method of treating and/or preventing a hyperproliferative disease, preferably cancer, as described herein. In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 29 and a light chain comprising the amino acid sequence of SEQ ID NO: 30. In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 31 and a light chain comprising the amino acid sequence of SEQ ID NO: 32. In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 33 and a light chain comprising the amino acid sequence of SEQ ID NO: 34.

In another aspect, the invention refers to a combination, a pharmaceutical composition or a kit according to the invention, each as described herein, comprising, consisting or consisting essentially of an LRP5 antagonist (e.g. any one of LRP5#1, LRP5#2, LRP5#3, LRP5#4, LRP5#5, LRP5#6, LRP5#7, LRP5#8, LRP5#9 as defined by the CDR and/or VHH sequences of Tables 1a, 1b, 1c, 2a, 2b, 2c) and an anti-PD-1 antibody, (e.g., any one of PD1-1, PD1-2, PD1-3, PD1-4, PD1-5 as defined by the CDR and/or VH/VL sequences of Tables 3 and 4), for use in a method of treating and/or preventing a or hyperproliferative disease preferably cancer, as described herein. In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 29 and a light chain comprising the amino acid sequence of SEQ ID NO: 30. In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 31 and a light chain comprising the amino acid sequence of SEQ ID NO: 32. In preferred embodiments, the LRP5 antagonist comprises an amino acid sequence of SEQ ID NO:57, SEQ ID NO:58 or SEQ ID NO:59 and the PD-1 antibody comprises a heavy chain comprising the amino acid sequence of SEQ ID NO: 33 and a light chain comprising the amino acid sequence of SEQ ID NO: 34.

The permutation of embodiments in respect of the LRP5 antagonists LRP5#1, LRP5#2, LRP5#3, LRP5#4, LRP5#5, LRP5#6, LRP5#7, LRP5#8, LRP5#9 with in respect of the PD-1 antagonist PD1-1, PD1-2, PD1-3, PD1-4, PD1-5 results in specific combinations which shall all be deemed to be specifically disclosed and to be embodiments of the invention and of all of its combinations, compositions, kits, methods, uses and compounds for use including methods applying specific administration/dosing regimens as detailed below and/or for treatment of specific cancers as detailed below.

Routes of administration for the LRP5 antagonist and/or the anti-PD1 antibody as described herein, include, but are not limited to parenteral (e.g. intramuscular, intraperitoneal, intravenous, transdermal or subcutaneous injection, or implant), oral, enterical, nasal, vaginal, rectal, or topical administration. In a preferred embodiment, the route of administration is intravenous administration, especially intravenous infusion or injection. The compounds of the present invention may be formulated, alone or together, in suitable dosage unit formulations containing conventional non-toxic pharmaceutically acceptable carriers, excipients and/or vehicles appropriate for each route of administration. More preferably, formulations include solid, semi-solid or liquid dosage forms, such as lyophilisation, liquid solutions (e.g. injectable and infusible solutions), dispersions or suspensions, liposomes and suppositories. The preferred mode depends on the intended mode of administration and therapeutic application. Especially preferred embodiments include liquid formulations and lyophilisation. In the case of a lyophilisation, the lyophilisate may be reconstituted in a liquid, preferably water.

Administration of the anti-PD-1 antibody, as described herein may e.g. be by injection (e.g. subcutaneously or intravenously) at a dose of about 0.1 to 30 mg/kg of patient body weight, e.g. about 0.5 to 25 mg/kg of patient body weight, about 1 to 20 mg/kg of patient body weight, about 2 to 5 mg/kg of patient body weight, or about 3 mg/kg of patient body weight.

In some embodiments, the anti-PD-1 antibody is administered at a dose from about 10 to 20 mg/kg of patient body weight every two weeks. The antibody molecule can be administered by intravenous infusion at a rate of more than 20 mg/min, e.g., 20-40 mg/min, and typically greater than or equal to 40 mg/min to reach a dose of about 35 to 440 mg/m$^2$, typically about 70 to 310 mg/m$^2$, and more typically, about 110 to 130 mg/m$^2$. In some embodiments, the infusion rate of about 110 to 130 mg/m$^2$ achieves a level of about 3 mg/kg of patient body weight. In other embodiments, the antibody molecule can be administered by intravenous infusion at a rate of less than 10 mg/min, e.g., less than or equal to 5 mg/min to reach a dose of about 1 to 100 mg/m$^2$, e.g., about 5 to 50 mg/m$^2$, about 7 to 25 mg/m$^2$, or, about 10 mg/m$^2$. In some embodiments, the antibody is infused over a period of about 30 min.

Preferred dosage regimens for an anti-PD-1 antibody described herein include 1 mg/kg of patient body weight or alternatively 3 mg/kg of patient body weight via intravenous administration, with the antibody being given every three weeks or every four weeks.

The LRP5 antagonist described herein or the compositions comprising the same can for example be administered intravenously (i.v.), subcutaneously (s.c.), intramuscularly (i.m.), intraperitoneally (i.p.), transdermally, orally, sublingually (e.g. in the form of a sublingual tablet, spray or drop placed under the tongue and adsorbed through the mucus membranes into the capillary network under the tongue), (intra-) nasally (e.g. in the form of a nasal spray and/or as an aerosol), topically, by means of a suppository, by inhalation, or any other suitable manner in an effective amount or dose.

The LRP5 antagonists described herein will generally be administered in an amount between 0.005 and 20.0 mg per kilogram of patient body weight and dose, preferably between 0.05 and 10.0 mg/kg/dose, and more preferably between 0.5 and 10 mg/kg/dose, but can vary, especially, depending on the specific disease, disorder or condition to be treated, the potency of the specific LRP5 antagonist to be used, the specific route of administration and the specific pharmaceutical formulation or composition used. Thus, in some cases it may be sufficient to use less than the minimum dose given above, whereas in other cases the upper limit may have to be exceeded. When administering large amounts it may be advisable to divide them up into a number of smaller doses spread over the day.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions.

The LRP5 antagonist and the anti-PD1 antibody as described herein may be administered at therapeutically effective amounts in single or divided doses administered at appropriate time intervals. A therapeutically effective amount refers to an amount effective at dosages and for periods of time necessary to achieve the desired therapeutic result and is the minimum amount necessary to prevent, ameliorate, or treat a disease or disorder. A therapeutically effective amount of the compounds described herein may vary according to factors such as the disease state, age, sex, and weight of the individual, and the ability of the compound to elicit a desired response in the individual. A therapeutically effective amount is also one in which any toxic or detrimental effects of the compound is outweighed by the therapeutically beneficial effects. A therapeutically effective dose preferably inhibits a measurable parameter, e.g. a tumor growth rate by at least about 20%, more preferably by at least about 40%, even more preferably by at least about 60%, and still more preferably by at least about 80% relative to untreated subjects or relative to a preceding untreated period of the same subject that is to be treated.

The active compounds may be administered in such doses which are therapeutically effective in monotherapy, or in such doses which are lower or higher than the doses used in monotherapy, but when combined result in a desired (jointly) therapeutically effective amount. This may for example be useful for avoiding, limiting or reducing any unwanted side-effects that are associated with the use of one or more of the substances or principles when they are used in their usual amounts, while still obtaining the desired pharmacological or therapeutic effect.

The amount of the compounds described herein required for use in treatment may be adapted to the particular compound selected, the route of administration, the nature of the condition being treated and the age and condition of the patient and will be ultimately at the discretion of the attendant physician or clinician. Also, the dosage of the compounds described herein may be adapted depending on the target cell, tumor, tissue, graft, or organ.

The desired dose of the LRP5 antagonist or anti-PD-1 antibody both as described herein may be administered as a fixed amount per administration or as bolus, to reach a set blood concentration in the patient.

Within this invention it will be appreciated that the LRP5 antagonist and the anti-PD1 antibody can be administered formulated either dependently (i.e. mixed together into one composition) or independently (i.e. as separate compositions), wherein such administration provides therapeutically effective levels of the two compounds in the body of the patient. The latter also applies to cocktail therapy, e.g. the administration of three or more active agents. In other words, the LRP5 antagonist and the anti-PD1 antibody may be administered either as part of the same pharmaceutical composition/dosage form or, preferably, in separate pharmaceutical compositions/dosage forms. In as far as the administration is in separate pharmaceutical compositions/dosage forms, it is to be understood that according to this invention said administration envisages the simultaneous, concurrent, sequential or alternate administration of the active agents or components.

The term "simultaneous" (also referred to as "concomitant" herein) refers to the administration of both compounds/compositions at substantially the same time.

Concurrent administration includes administering the active agents within the same general time period, for example on the same day(s) but not necessarily at the same time.

Sequential administration includes administration of one agent during a first time period (for example over the course of a few hours, days or a week) using one or more doses, followed by administration of the other agent during a second time period (for example over the course of a few hours, days or a week) using one or more doses. An overlapping schedule may also be employed, which includes administration of the active agents on different days over the treatment period, not necessarily according to a regular sequence. Alternatively, a successive administration is also envisaged, the second administration step is carried out immediately once the administration of the first compounds has been finished. The skilled person knows how to determine the finish of the first administration step, thereby enabling them to identify the suitable time point for initiation the second administration step.

Alternate administration includes administration of one agent during a time period, for example over the course of a few hours, days or a week, followed by administration of the other agent during a subsequent period of time, for example over the course of a few hours, days or a week, and then repeating the pattern for one or more cycles, wherein the overall number of repeats depends on the chosen dosage regimen.

Variations on these general guidelines may also be employed, e.g. according to the agents used and the condition of the subject.

In a preferred embodiment of the invention, in the method according to the present invention, the LRP5 antagonist and the anti-PD1 antibody each as described herein are administered simultaneously or concurrently (e.g., by intravenous infusion or subcutaneously) during a first period followed by a second period when the anti-PD1 antibody is administered (e.g., by intravenous infusion or subcutaneously) and the LRP5 antagonist is not administered.

In some embodiments, the first period is 3 or 6 weeks, when the LRP5 antagonist and the PD1 antibody are administered every three weeks.

In some embodiments, the first period is 4 or 8 weeks, when the LRP5 antagonist and the PD1 antibody are administered every four weeks.

It is particularly preferred that this administration schedule is employed with the LRP5 antagonist being LRP5#2 and the anti-PD-1 antibody being PD1-1, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies.

It is particularly preferred that this administration schedule is employed with the LRP5 antagonist being LRP5#6 and the anti-PD-1 antibody being PD1-1, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies.

It is particularly preferred that this administration schedule is employed with the LRP5 antagonist being LRP5#7 and the anti-PD-1 antibody being PD1-1, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies.

It is particularly preferred that this administration schedule is employed with the LRP5 antagonist being LRP5#2 and the anti-PD-1 antibody being PD1-2, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies.

It is particularly preferred that this administration schedule is employed with the LRP5 antagonist being LRP5#6 and the anti-PD-1 antibody being PD1-2, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies.

It is particularly preferred that this administration schedule is employed with the LRP5 antagonist being LRP5#7 and the anti-PD-1 antibody being PD1-2, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies.

It is particularly preferred that this administration schedule is employed with the LRP5 antagonist being LRP5#2 and the anti-PD-1 antibody being PD1-3, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies.

It is particularly preferred that this administration schedule is employed with the LRP5 antagonist being LRP5#6 and the anti-PD-1 antibody being PD1-3, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies.

It is particularly preferred that this administration schedule is employed with the LRP5 antagonist being LRP5#7 and the anti-PD-1 antibody being PD1-3, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies.

In another preferred embodiment of the invention, the LRP5 antagonist and the anti-PD1 antibody as described herein are both administered (simultaneously or concurrently by intravenous infusion or subcutaneously) every three weeks during a first period (of e.g. 3 or 6 weeks) and then the anti-PD1 antibody is administered, e.g., every three weeks during a second period (e.g., by intravenous infusion or subcutaneously). For example, the LRP5 antagonist and the anti-PD1 antibody are administered simultaneously or concurrently (e.g., by intravenous infusion or subcutaneously) in (i) week 1 or (ii) in week 1 and week 4, and then the PD1 antibody is administered, e.g., in week 7, 10, and any subsequent third week (week 13, 16, etc) until treatment is terminated. In case of option (i), the PD1 antibody is already administered alone in week 4 (i.e. instead of the combined administration with the LRP5 antagonist as in option (ii)).

It is particularly preferred that this administration schedule is employed with the LRP5 antagonist being LRP5#2 and the anti-PD-1 antibody being PD1-1, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#6 and the anti-PD-1 antibody being PD1-1, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#7 and the anti-PD-1 antibody being PD1-1, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#2 and the anti-PD-1 antibody being PD1-2, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#6 and the anti-PD-1 antibody being PD1-2, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#7 and the anti-PD-1 antibody being PD1-2, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#2 and the anti-PD-1 antibody being PD1-3, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#6 and the anti-PD-1 antibody being PD1-3, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#7 and the anti-PD-1 antibody being PD1-3, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies.

In another preferred embodiment of the invention, the LRP5 antagonist and the anti-PD1 antibody as described herein are both administered (simultaneously or concurrently by intravenous infusion or subcutaneously) every four weeks during a first period (of e.g. 4 or 8 weeks) and then the anti-PD1 antibody is administered, e.g., every four weeks, during a second period (e.g., by intravenous infusion or subcutaneously). For example, the LRP5 antagonist and the anti-PD1 antibody are administered simultaneously or concurrently (e.g., by intravenous infusion or subcutaneously) in (i) week 1 or (ii) in week 1 and week 5, and then the PD1 antibody is administered, e.g., in week 9, 13, and any subsequent fourth week (week 17, 21, etc) until treatment is terminated. In case of option (i), the PD1 antibody is already administered alone in week 5 (i.e. instead of the combined administration with the LRP5 antagonist as in option (ii)).

It is particularly preferred that this administration schedule is employed with the LRP5 antagonist being LRP5#2 and the anti-PD-1 antibody being PD1-1, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#6 and the anti-PD-1 antibody being PD1-1, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#7 and the anti-PD-1 antibody being PD1-1, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#2 and the anti-PD-1 antibody being PD1-2, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#6 and the anti-PD-1 antibody being PD1-2, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#7 and the anti-PD-1 antibody being PD1-2, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#2 and the anti-PD-1 antibody being PD1-3, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#6 and the anti-PD-1 antibody being PD1-3, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#7 and the anti-PD-1 antibody being PD1-3, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies.

Preferably, the LRP5 antagonist as described herein (e.g., at a dose of about 0.5 to 10 mg/kg of patient body weight) and the anti-PD1 antibody as described herein (e.g. at a dose of any one of 2, 3, 4, or 5 mg/kg of patient body weight) are both administered (simultaneously or concurrently by intravenous infusion or subcutaneously) every three or four weeks during a first period (e.g. corresponding to 1 or 2 dosages) and then the anti-PD1 antibody is administered, e.g., every three or four weeks during a second period (e.g., by intravenous infusion or subcutaneously).

It is particularly preferred that this administration schedule is employed with the LRP5 antagonist being LRP5#2 and the anti-PD-1 antibody being PD1-1, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#6 and the anti-PD-1 antibody being PD1-1, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#7 and the anti-PD-1 antibody being PD1-1, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#2 and the anti-PD-1 antibody being PD1-2, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#6 and the anti-PD-1 antibody being PD1-2, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#7 and the anti-PD-1 antibody being PD1-2, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#2 and the anti-PD-1 antibody being PD1-3, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#6 and the anti-PD-1 antibody being PD1-3, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies. It is particularly preferred that this administration schedule is employed with the LRP5 antagonist being LRP5#7 and the anti-PD-1 antibody being PD1-3, even more preferably it is employed for the treatment of gastrointestinal cancers, melanoma, bladder cancer or lung cancer (including gastrointestinal cancers, melanomas, bladder cancer and lung cancer that are refractory or resistant to checkpoint inhibitor therapies) or any solid tumor which is refractory or resistant to checkpoint inhibitor therapies.

In some embodiments of the invention, the LRP5 antagonist and the anti-PD1 antibody as described herein are both administered (simultaneously or concurrently by intravenous infusion or subcutaneously) every three or four weeks during a first period (e.g. corresponding to 1 or 2 dosages) and then the anti-PD1 antibody is administered weekly, every other week, every three weeks or monthly during a second period (e.g., by intravenous infusion or subcutaneously).

Depending on the disease to be treated, the combination therapy as defined herein may be used on its own or in further combination with one or more additional therapeutic agents, in particular selected from chemotherapeutic agents or therapeutically active compounds that inhibit angiogenesis, signal transduction pathways or mitotic checkpoints in cancer cells.

The additional therapeutic agent may be administered simultaneously with, optionally as a component of the same pharmaceutical preparation, or before or after administration of the LRP5 antagonist and/or the PD1 antibody.

This/these additional therapeutic agent(s) may (each) be selected from the following (without being limited thereto):
  an immunotherapeutic agent, such as modulators of the following checkpoint inhibitors: TIM3, PD-L1, PD-L2, CTLA-4, VISTA, BTLA, TIGIT, CD160, LAIR1, 2B4, CEACAM;
  a cancer vaccine;
  a DNA damaging agent;
  an inhibitor of angiogenesis;
  an inhibitor of signal transduction pathways;
  an inhibitor of mitotic checkpoints; and
hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor (PDGF)", "fibroblast growth factor (FGF)", "vascular endothelial growth factor (VEGF)", "epidermal growth factor (EGF)", "insuline-like growth factors (IGF)", "human epidermal growth factor (HER, e.g. HER2, HER3, HER4)" and "hepatocyte growth factor (HGF)"), inhibitors are for example "growth factor" antibodies, "growth factor receptor" antibodies and tyrosine kinase inhibitors, such as for example cetuximab, gefitinib, imatinib, lapatinib, bosutinib and trastuzumab); antimetabolites (e.g. antifolates such as methotrexate, raltitrexed, pyrimidine analogues such as 5-fluorouracil (5-FU), capecitabine and gemcitabine, purine and adenosine analogues such as mercaptopurine, thioguanine, cladribine and pentostatin, cytarabine (ara C), fludarabine); antitumour antibiotics (e.g. anthracyclins such as doxorubicin, doxil (pegylated liposomal doxorubicin hydrochloride, myocet (non-pegylated liposomal doxorubicin), daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); angiogenesis inhibitors (e.g. tasquinimod), tubuline inhibitors; DNA synthesis inhibitors (e.g. sapacitabine), PARP inhibitors, topoisomerase inhibitors (e.g. epipodophyllotoxins such as for example etoposide and etopophos, teniposide, amsacrin, topotecan, irinotecan, mitoxantrone), serine/threonine kinase inhibitors (e.g. PDK 1 inhibitors, Raf inhibitors, A-Raf inhibitros, B-Raf inhibitors, C-Raf inhibitors, mTOR inhibitors, mTORC1/2 inhibitors, PI3K inhibitors, PI3Kα inhibitors, dual mTOR/PI3K inhibitors, STK 33 inhibitors, AKT inhibitors, PLK 1 inhibitors, inhibitors of CDKs, Aurora kinase inhibitors), tyrosine kinase inhibitors (e.g. PTK2/FAK inhibitors), protein protein interaction inhibitors (e.g. IAP activator, Mcl-1, MDM2/MDMX), MEK inhibitors (e.g. pimasertib), ERK inhibitors, FLT3 inhibitors (e.g. quizartinib), BRD4 inhibitors, IGF-1R inhibitors, TRAILR2 agonists, Bcl-xL inhibitors, Bcl-2 inhibitors (e.g. venetoclax), Bcl-2/Bcl-xL inhibitors, ErbB receptor inhibitors, BCR-ABL inhibitors, ABL inhibitors, Src inhibitors, rapamycin analogs (e.g. everolimus, temsirolimus, ridaforolimus, sirolimus), androgen synthesis inhibitors (e.g. abiraterone, TAK-700), androgen receptor inhibitors (e.g. enzalutamide, ARN-509), immunotherapy (e.g. sipuleucel-T), DNMT inhibitors (e.g. SGI 110, temozolomide, vosaroxin), HDAC inhibitors (e.g. vorinostat, entinostat, pracinostat, panobinostat), ANG1/2 inhibitors (e.g. trebananib), CYP17 inhibitors (e.g. galeterone), radiopharmaceuticals (e.g. radium-223, alpharadin), immunotherapeutic agents (e.g. poxvirus-based vaccine, ipilimumab, immune checkpoint inhibitors) and various chemotherapeutic agents such as amifostin, anagrelid, clodronat, filgrastin, interferon, interferon alpha, leucovorin, rituximab, procarbazine, levamisole, mesna, mitotane, pamidronate and porfimer; 2-chlorodesoxyadenosine, 2-fluorodesoxy-cytidine, 2-methoxyoestradiol, 2C4, 3-alethine, 131-I-TM-601, 3CPA, 7-ethyl-10-hydroxycamptothecin, 16-aza-epothilone B, ABT-199, ABT-263/navitoclax, ABT-737, A 105972, A 204197, aldesleukin, alisertib/ MLN8237, alitretinoin, allovectin-7, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, AMG-479 (ganitumab), AMG-232, AMG-511, AMG 2520765, AMG 2112819, ARRY 162, ARRY 438162, ARRY-300, ARRY-142886/AZD-6244 (selumetinib), ARRY-704/AZD-8330, ATSP-7041, AR-12, AR-42, AS-703988, AXL-1717, AZD-1480, AZD-4547, AZD-8055, AZD-5363, AZD-6244, AZD-7762, ARQ-736, ARQ 680, AS-703026 (primasertib), avastin, AZD-2014, azacitidine (5-aza), azaepothilone B, azonafide, barasertib/AZD1152, BAY-43-9006, BAY 80-6946, BBR-3464, BBR-3576, bevacizumab, BEZ-235/ dactolisib, biricodar dicitrate, birinapant, BCX-1777, BKM-120/buparlisib, bleocin, BLP-25, BMS-184476, BMS-247550, BMS-188797, BMS-275291, BMS-663513, BMS-754807, BNP-1350, BNP-7787, BIBW 2992/afatinib, BIBF 1120/nintedanib, BI 836845, BI 2536, BI 6727/volasertib, BI 836845, BI 847325, BI 853520, BIIB-022, bleomycinic acid, bleomycin A, bleomycin B, brivanib, bryostatin-1, bortezomib, brostallicin, busulphan, BYL-719/alpelisib, CA-4 prodrug, CA-4, cabazitaxel, cabozantinib, CapCell, calcitriol, canertinib, canfosfamide, capecitabine, carboxyphthalatoplatin, CCI-779, CC-115, CC-223, CEP-701, CEP-751, CBT-1 cefixime, ceflatonin, ceftriaxone, celecoxib, celmoleukin, cemadotin, CGM-097, CH4987655/ RO-4987655, chlorotrianisene, cilengitide, ciclosporin, CD20 antibodies, CDA-II, CDC-394, CKD-602, CKI-27, clofarabine, colchicin, combretastatin A4, COT inhibitors, CHS-828, CH-5132799, CLL-Thera, CMT-3 cryptochycin 52, CPI-613, CTP-37, CTLA-4 monoclonal antibodies (e.g. ipilimumab), CP-461, crizotinib, CV-247, cyanomorpholinodoxorubicin, cytarabine, D 24851, dasatinib, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, DS-7423, DS-3032, E7010, E-6201, edatrexat, edotreotide, efaproxiral, eflornithine, EGFR inhibitors, EKB-569, EKB-509, enzastaurin, elesclomol, elsamitrucin, epothilone B, epratuzumab, EPZ-004777, ER-86526, erlotinib, ET-18-OCH3, ethynylcytidine, ethynyloestradiol, exatecan, exatecan mesylate, exemestane, exisulind, fenretinide, figitumumab, floxuridine, folic acid, FOLFOX, FOLFOX4, FOLFIRI, formestane, fostamatinib, fotemustine, galarubicin, gallium maltolate, ganetespib, gefinitib, gemtuzumab, gemtuzumab ozogamicin, gimatecan, glufosfamide, GCS-100, GDC-0623, GDC-0941 (pictrelisib), GDC-0980, GDC-0032, GDC-0068, GDC-0349, GDC-0879, G17DT immunogen, GMK, GMX-1778, GPX-100, gp100-peptide vaccines, GSK-5126766, GSK-690693, GSK-1120212 (trametinib), GSK-1995010, GSK-2118436 (dabrafenib), GSK-2126458, GSK-2132231A, GSK-2334470, GSK-2110183, GSK-2141795, GSK-2636771, GSK-525762A/I-BET-762, GW2016, granisetron, herceptine, hexamethylmelamine, histamine, homoharringtonine, hyaluronic acid, hydroxyurea, hydroxyprogesterone caproate, HDM-201, ibandronate, ibritumomab, ibrutinib/PCI-32765, idasanutlin, idatrexate, idelalisib/CAL-101, idenestrol, IDN-5109, IGF-1R inhibitors, IMC-1C11, IMC-A12 (cixutumumab), immunol, indisulam, interferon alpha-2a, interferon alpha-2b, pegylated interferon alpha-2b, interleukin-2, INK-1117, INK-128, INSM-18, ionafarnib, iproplatin, irofulven, isohomohalichondrin-B, isoflavone, isotretinoin, ixabepilone, JRX-2, JSF-154, JQ-1, J-107088, conjugated oestrogens, kahalid F, ketoconazole, KW-2170, KW-2450, KU-55933, LCL-161, lobaplatin, leflunomide, lenalidomide, lenograstim, leuprolide, leuporelin, lexidronam, LGD-1550, linezolid, lovastatin, lutetium texaphyrin, lometrexol, lonidamine, losoxantrone, LU 223651, lurbinectedin, lurtotecan, LY-S6AKT1, LY-2780301, LY-2109761/galunisertib, mafosfamide, marimastat, masoprocol, mechloroethamine, MEK inhibitors, MEK-162, methyltestosteron, methylprednisolone, MEDI-573, MEN-10755, MDX-H210, MDX-447, MDX-1379, MGV, midostaurin, minodronic acid, mitomycin, mivobulin, MK-2206, MK-0646 (dalotuzumab), MLN518, MLN-0128, MLN-2480, motexafin gadolinium, MS-209, MS-275, MX6, neridronate, neratinib, Nexavar, neovastat, nilotinib, nimesulide, nitroglycerin, nolatrexed, norelin, N-acetylcysteine, NU-7441 06-benzylguanine, oblimersen, omeprazole, olaparib, oncophage, oncoVEX$^{GM-CSF}$, ormiplatin, ortataxel, OX44 antibodies, OSI-027, OSI-906 (linsitinib), 4-1 BB antibodies, oxantrazole, oestrogen, onapristone, palbociclib/PD-0332991, panitumumab, panobinostat, patupilone, pazopanib, pegfilgrastim, PCK-3145, pegfilgrastim, PB1-1402, PBI-05204, PD0325901, PD-1 and PD-L1 antibodies (e.g. pembrolizumab, nivolumab, pidilizumab, MEDI-4736/durvalumab, RG-7446/atezolizumab), PD-616, PEG-paclitaxel, albumin-stabilized paclitaxel, PEP-005, PF-05197281, PF-05212384, PF-04691502, PF-3758309, PHA-665752, PHT-427, P-04, PKC412, P54, PI-88, pelitinib, pemetrexed, pentrix, perifosine, perillylalcohol, pertuzumab, pevonedistat, PI3K inhibitors, PI3K/mTOR inhibitors, PG-TXL, PG2, PLX-4032/RO-5185426 (vemurafenib), PLX-3603/RO-5212054, PT-100, PWT-33597, PX-866, picoplatin, pivaloyloxymethylbutyrate, pixantrone, phenoxodiol O, PKI166, plevitrexed, plicamycin, polyprenic acid, ponatinib, porfiromycin, posaconazole, prednisone, prednisolone, PRT-062607, quinamed, quinupristin, quizartinib/AC220, R115777, RAF-265, ramosetron, ranpirnase, RDEA-119/BAY 869766, RDEA-436, rebeccamycin analogues, receptor tyrosine kinase (RTK) inhibitors, revimid, RG-7167, RG-7112, RG-7304, RG-7421, RG-7321, RG-7356, RG 7440, RG-7775, rhizoxin, rhu-MAb, rigosertib rinf abate, risedronate, rituximab, robatumumab, rofecoxib, romidepsin, RO-4929097, RO-31-7453, RO-5126766, RO-5068760, RPR 109881A, rubidazone, rubitecan, R-flurbiprofen, RX-0201, ruxolitinib, S-9788, sabarubicin, SAHA, sapacitabine, SAR-405838, sargramostim, satraplatin, SB-408075, SB-431542, Se-015/Ve-015, SU5416, SU6668, SDX-101, selinexor, semustin, seocalcitol, SM-11355, SN-38, SN-4071, SR-27897, SR-31747, SR-13668, SRL-172, sorafenib, spiroplatin, squalamine, STF-31, suberanilohydroxamic acid, sutent, T 900607, T 138067, TAE-684, TAK-733, TAS-103, tacedinaline, talaporfin, tanespimycin, Tarceva, tariquitar, tasisulam, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymalfasin, thymectacin, tiazofurin, tipifarnib, tirapazamine, tocladesine, tomudex, toremofin, tosedostat, trabectedin, TransMID-107, transretinic acid, traszutumab, tremelimumab, tretinoin, triacetyluridine, triapine, triciribine, trimetrexate, TLK-286TXD 258, tykerb/tyverb, urocidin, valproic acid, valrubicin, vandetanib, vatalanib, vincristine, vinflunine, virulizin, vismodegib, vosaroxin, WX-UK1, WX-554, vectibix, XAV-939, xeloda, XELOX, XL-147, XL-228, XL-281, XL-518/R-7420/GDC-0973, XL-765, YM-511, YM-598, ZD-4190, ZD-6474, ZD-4054, ZD-0473, ZD-6126, ZD-9331, ZD1839, ZSTK-474, zoledronat and zosuquidar.

In some embodiments, the combination therapy as described involves the LRP5 antagonist and the anti-PD-1 antibody as described herein without any additional chemotherapeutic agent.

Hyperproliferative Diseases/Cancers

The combinations, compositions, kits, uses, methods and compounds for use according to the present invention (including all embodiments) are useful for the treatment and/or prevention of hyperproliferative disorders, in particular cancer.

In certain embodiments the combinations, compositions, kits, uses, methods and compounds for use according to the present invention (including all embodiments) are useful for the treatment of hyperproliferative disorders, in particular cancer.

As used herein, "hyperproliferative disease" refers to conditions wherein cell growth is increased over normal levels. For example, hyperproliferative diseases or disorders include malignant diseases (e.g. esophageal cancer, colon cancer, biliary cancer) and non-malignant diseases (e.g. atherosclerosis, benign hyperplasia, benign prostatic hypertrophy).

In preferred embodiments, the hyperproliferative disorder is cancer.

Cancers are classified in two ways: by the type of tissue in which the cancer originates (histological type) and by primary site, or the location in the body, where the cancer first developed. The most common sites in which cancer develops include the skin, lung, breast, prostate, colon and rectum, cervix and uterus as well as the hematological compartment The combinations, compositions, kits, uses, methods and compounds for use according to the invention (including all embodiments) may be useful in the treatment of a variety of hyperproliferative disorders, in particular cancers, including, for example, but not limited to the following:
- gastrointestinal cancers such as esophageal cancer (e.g., gastroesophageal junction cancer), stomach (gastric) cancer, hepatocellular carcinoma, biliary tract cancer (e.g., cholangiocarcinoma), gallbladder cancer, pancreatic cancer or colorectal cancer (CRC);
- melanoma;
- bladder cancer; and
- lung cancer (e.g. NSCLC).

In some embodiments of the invention, the combinations, compositions, kits, uses, methods and compounds for use according to the invention (including all embodiments) are used to treat gastrointestinal cancers, preferably esophageal cancer (e.g., gastroesophageal junction cancer), stomach (gastric) cancer, hepatocellular carcinoma, biliary tract cancer (e.g., cholangiocarcinoma), gallbladder cancer, pancreatic cancer or colorectal cancer (CRC). It is particularly preferred that these cancers are treated with LRP5#2 as the LRP5 antagonist and PD1-1 as the anti-PD-1 antibody. It is particularly preferred that these cancers are treated with LRP5#6 as the LRP5 antagonist and PD1-1 as the anti-PD-1 antibody. It is particularly preferred that these cancers are treated with LRP5#7 as the LRP5 antagonist and PD1-1 as the anti-PD-1 antibody. It is particularly preferred that these cancers are treated with LRP5#2 as the LRP5 antagonist and PD1-2 as the anti-PD-1 antibody. It is particularly preferred that these cancers are treated with LRP5#6 as the LRP5 antagonist and PD1-2 as the anti-PD-1 antibody. It is particularly preferred that these cancers are treated with LRP5#7 as the LRP5 antagonist and PD1-2 as the anti-PD-1 antibody. It is particularly preferred that these cancers are treated with LRP5#2 as the LRP5 antagonist and PD1-3 as the anti-PD-1 antibody. It is particularly preferred that these cancers are treated with LRP5#6 as the LRP5 antagonist and PD1-3 as the anti-PD-1 antibody. It is particularly preferred that these cancers are treated with LRP5#7 as the LRP5 antagonist and PD1-3 as the anti-PD-1 antibody.

In some embodiments of the invention, the combinations, compositions, kits, uses, methods and compounds for use according to the invention (including all embodiments) are used in the treatment of melanoma. It is particularly preferred that these cancers are treated with LRP5#2 as the LRP5 antagonist and PD1-1 as the anti-PD-1 antibody. It is particularly preferred that these cancers are treated with LRP5#6 as the LRP5 antagonist and PD1-1 as the anti-PD-1 antibody. It is particularly preferred that these cancers are treated with LRP5#7 as the LRP5 antagonist and PD1-1 as the anti-PD-1 antibody. It is particularly preferred that these cancers are treated with LRP5#2 as the LRP5 antagonist and PD1-2 as the anti-PD-1 antibody. It is particularly preferred that these cancers are treated with LRP5#6 as the LRP5 antagonist and PD1-2 as the anti-PD-1 antibody. It is particularly preferred that these cancers are treated with LRP5#7 as the LRP5 antagonist and PD1-2 as the anti-PD-1 antibody. It is particularly preferred that these cancers are treated with LRP5#2 as the LRP5 antagonist and PD1-3 as the anti-PD-1 antibody. It is particularly preferred that these cancers are treated with LRP5#6 as the LRP5 antagonist and PD1-3 as the anti-PD-1 antibody. It is particularly preferred that these cancers are treated with LRP5#7 as the LRP5 antagonist and PD1-3 as the anti-PD-1 antibody.

In some embodiments of the invention, the combinations, compositions, kits, uses, methods and compounds for use according to the invention (including all embodiments) are used in the treatment of bladder cancer. It is particularly preferred that these cancers are treated with LRP5#2 as the LRP5 antagonist and PD1-1 as the anti-PD-1 antibody. It is particularly preferred that these cancers are treated with LRP5#6 as the LRP5 antagonist and PD1-1 as the anti-PD-1 antibody. It is particularly preferred that these cancers are treated with LRP5#7 as the LRP5 antagonist and PD1-1 as the anti-PD-1 antibody. It is particularly preferred that these cancers are treated with LRP5#2 as the LRP5 antagonist and PD1-2 as the anti-PD-1 antibody. It is particularly preferred that these cancers are treated with LRP5#6 as the LRP5 antagonist and PD1-2 as the anti-PD-1 antibody. It is particularly preferred that these cancers are treated with LRP5#7 as the LRP5 antagonist and PD1-2 as the anti-PD-1 antibody. It is particularly preferred that these cancers are treated with LRP5#2 as the LRP5 antagonist and PD1-3 as the anti-PD-1 antibody. It is particularly preferred that these cancers are treated with LRP5#6 as the LRP5 antagonist and PD1-3 as the anti-PD-1 antibody. It is particularly preferred that these cancers are treated with LRP5#7 as the LRP5 antagonist and PD1-3 as the anti-PD-1 antibody.

In some embodiment of the invention, the combinations, compositions, kits, uses, methods and compounds for use according to the invention (including all embodiments) are used in the treatment of lung cancer (e.g. Non-small-cell lung carcinoma (NSCLC)). It is particularly preferred that these cancers are treated with LRP5#2 as the LRP5 antagonist and PD1-1 as the anti-PD-1 antibody. It is particularly preferred that these cancers are treated with LRP5#6 as the LRP5 antagonist and PD1-1 as the anti-PD-1 antibody. It is particularly preferred that these cancers are treated with LRP5#7 as the LRP5 antagonist and PD1-1 as the anti-PD-1 antibody. It is particularly preferred that these cancers are treated with LRP5#2 as the LRP5 antagonist and PD1-2 as the anti-PD-1 antibody. It is particularly preferred that these cancers are treated with LRP5#6 as the LRP5 antagonist and PD1-2 as the anti-PD-1 antibody. It is particularly preferred that these cancers are treated with LRP5#7 as the LRP5 antagonist and PD1-2 as the anti-PD-1 antibody. It is particularly preferred that these cancers are treated with LRP5#2 as the LRP5 antagonist and PD1-3 as the anti-PD-1 antibody. It is particularly preferred that these cancers are treated with LRP5#6 as the LRP5 antagonist and PD1-3 as the anti-PD-1 antibody. It is particularly preferred that these cancers are treated with LRP5#7 as the LRP5 antagonist and PD1-3 as the anti-PD-1 antibody.

In a further embodiment of the invention, the combinations, compositions, kits, uses, methods and compounds for use according to the invention (including all embodiments) are used in the treatment of cancer patients (e.g. patients suffering from (i) a gastrointestinal cancer such as esophageal cancer gastric cancer, hepatocellular carcinoma, biliary tract cancer gallbladder cancer, pancreatic cancer or colorectal cancer, (ii) melanoma, (iii) bladder cancer or (iv) lung cancer) who are treatment naïve in respect of treatment with a checkpoint inhibitor or immunomodulator, i.e., e.g., patients who are treatment naïve in respect of treatment with an anti-PD-1 antibody. It is particularly preferred that these cancers are treated with LRP5#2 as the LRP5 antagonist and PD1-1 as the anti-PD-1 antibody. It is particularly preferred that these cancers are treated with LRP5#6 as the LRP5 antagonist and PD1-1 as the anti-PD-1 antibody. It is particularly preferred that these cancers are treated with LRP5#7 as the LRP5 antagonist and PD1-1 as the anti-PD-1 antibody. It is particularly preferred that these cancers are treated with LRP5#2 as the LRP5 antagonist and PD1-2 as the anti-PD-1 antibody. It is particularly preferred that these cancers are treated with LRP5#6 as the LRP5 antagonist and PD1-2 as the anti-PD-1 antibody. It is particularly preferred that these cancers are treated with LRP5#7 as the LRP5 antagonist and PD1-2 as the anti-PD-1 antibody. It is particularly preferred that these cancers are treated with LRP5#2 as the LRP5 antagonist and PD1-3 as the anti-PD-1 antibody. It is particularly preferred that these cancers are treated with LRP5#6 as the LRP5 antagonist and PD1-3 as the anti-PD-1 antibody. It is particularly preferred that these cancers are treated with LRP5#7 as the LRP5 antagonist and PD1-3 as the anti-PD-1 antibody.

In a further embodiment of the invention, the combinations, compositions, kits, uses, methods and compounds for use according to the invention (including all embodiments) are used in the treatment of cancer patients (e.g. patients suffering from (i) a gastrointestinal cancer such as esophageal cancer gastric cancer, hepatocellularcarcinoma, biliary tract cancer gallbladder cancer, pancreatic cancer or colorectal cancer, (ii) melanoma, (iii) bladder cancer or (iv) lung cancer) who relapsed during, subsequently or after treatment with a checkpoint inhibitor or immunomodulator, i.e., e.g., patients who relapsed during, subsequently or after treatment with a PD-1 antagonist such as an anti-PD-1 antibody. It is particularly preferred that these cancers are treated with LRP5#2 as the LRP5 antagonist and PD1-1 as the anti-PD-1 antibody. It is particularly preferred that these cancers are treated with LRP5#6 as the LRP5 antagonist and PD1-1 as the anti-PD-1 antibody. It is particularly preferred that these cancers are treated with LRP5#7 as the LRP5 antagonist and PD1-1 as the anti-PD-1 antibody. It is particularly preferred that these cancers are treated with LRP5#2 as the LRP5 antagonist and PD1-2 as the anti-PD-1 antibody. It is particularly preferred that these cancers are treated with LRP5#6 as the LRP5 antagonist and PD1-2 as the anti-PD-1 antibody. It is particularly preferred that these cancers are treated with LRP5#7 as the LRP5 antagonist and PD1-2 as the anti-PD-1 antibody. It is particularly preferred that these cancers are treated with LRP5#2 as the LRP5 antagonist and PD1-3 as the anti-PD-1 antibody. It is particularly preferred that these cancers are treated with LRP5#6 as the LRP5 antagonist and PD1-3 as the anti-PD-1 antibody. It is particularly preferred that these cancers are treated with LRP5#7 as the LRP5 antagonist and PD1-3 as the anti-PD-1 antibody.

The therapeutic applicability of the combination therapy according to this invention may include first line, second line, third line or further lines of treatment of patients (e.g. patients suffering from (i) a gastrointestinal cancer such as esophageal cancer, gastric cancer, hepatocellularcarcinoma, biliary tract cancer gallbladder cancer, pancreatic cancer or colorectal cancer, (ii) melanoma, (iii) bladder cancer or (iv) lung cancer). The cancer may be metastatic, recurrent, relapsed, resistant or refractory to one or more anti-cancer treatments. Thus, the patients may be treatment naïve, or may have received one or more previous anti-cancer therapies, which have not completely cured the disease.

Patients with relapse and/or with resistance to one or more anti-cancer agents (e.g. the single components of the combination, or standard chemotherapeutics) are also amenable for combined treatment according to this invention, e.g. for second or third line treatment cycles (optionally in further combination with one or more other anti-cancer agents), e.g. as add-on combination or as replacement treatment.

Accordingly, some of the disclosed combination therapies of this invention are effective at treating subjects (e.g. patients suffering from (i) a gastrointestinal cancer such as esophageal cancer, gastric cancer, hepatocellularcarcinoma, biliary tract cancer gallbladder cancer, pancreatic cancer or colorectal cancer, (ii) melanoma, (iii) bladder cancer or (iv) lung cancer) whose cancer has relapsed, or whose cancer has become drug resistant or multi-drug resistant, or whose cancer has failed one, two or more lines of mono- or combination therapy with one or more anti-cancer agents (e.g. the single components of the combination, or standard chemotherapeutics).

A cancer which initially responded to an anti-cancer drug can relapse and it can become resistant to the anti-cancer drug when the anti-cancer drug is no longer effective in treating the subject with the cancer, e.g. despite the administration of increased dosages of the anti-cancer drug. Cancers that have developed resistance to two or more anti-cancer drugs are said to be multi-drug resistant.

In preferred embodiments the combinations, compositions, kits, uses, methods and compounds for use according to the invention (including all embodiments) are used in the treatment of cancer patients (e.g. patients suffering from (i) a gastrointestinal cancer such as esophageal cancer, gastric cancer, hepatocellularcarcinoma, biliary tract cancer gallbladder cancer, pancreatic cancer or colorectal cancer, (ii) melanoma, (iii) bladder cancer or (iv) lung cancer) who have been previously treated with one or more immune checkpoint inhibitor and/or immuno modulator, e.g. one or more PD-1 antagonist(s) such as an anti-PD1 antibody It is particularly preferred that these cancers are treated with LRP5#2 as the LRP5 antagonist and PD1-1 as the anti-PD-1 antibody. It is particularly preferred that these cancers are treated with LRP5#6 as the LRP5 antagonist and PD1-1 as the anti-PD-1 antibody. It is particularly preferred that these cancers are treated with LRP5#7 as the LRP5 antagonist and PD1-1 as the anti-PD-1 antibody. It is particularly preferred that these cancers are treated with LRP5#2 as the LRP5 antagonist and PD1-2 as the anti-PD-1 antibody. It is particularly preferred that these cancers are treated with LRP5#6 as the LRP5 antagonist and PD1-2 as the anti-PD-1 antibody. It is particularly preferred that these cancers are treated with LRP5#7 as the LRP5 antagonist and PD1-2 as the anti-PD-1 antibody. It is particularly preferred that these cancers are treated with LRP5#2 as the LRP5 antagonist and PD1-3 as the anti-PD-1 antibody. It is particularly preferred that these cancers are treated with LRP5#6 as the LRP5 antagonist and PD1-3 as the anti-PD-1 antibody. It is particularly preferred that these cancers are treated with LRP5#7 as the LRP5 antagonist and PD1-3 as the anti-PD-1 antibody.

In a further preferred embodiment, the combinations, compositions, kits, uses, methods and compounds for use according to the invention (including all embodiments) are used in the treatment of cancer patients (e.g. patients suffering from (i) a gastrointestinal cancer such as esophageal cancer, gastric cancer, hepatocellularcarcinoma, biliary tract cancer gallbladder cancer, pancreatic cancer or colorectal cancer, (ii) melanoma, (iii) bladder cancer or (iv) lung cancer) who are refractory or resistant to checkpoint inhibitor therapies (e.g. to treatment with one or more immune checkpoint inhibitor and/or immuno modulators, e.g. one or more PD-1 antagonist(s) such as an anti-PD1 antibody). It is particularly preferred that these cancers are treated with LRP5#2 as the LRP5 antagonist and PD1-1 as the anti-PD-1 antibody. It is particularly preferred that these cancers are treated with LRP5#6 as the LRP5 antagonist and PD1-1 as the anti-PD-1 antibody. It is particularly preferred that these cancers are treated with LRP5#7 as the LRP5 antagonist and PD1-1 as the anti-PD-1 antibody. It is particularly preferred that these cancers are treated with LRP5#2 as the LRP5 antagonist and PD1-2 as the anti-PD-1 antibody. It is particularly preferred that these cancers are treated with LRP5#6 as the LRP5 antagonist and PD1-2 as the anti-PD-1 antibody. It is particularly preferred that these cancers are treated with LRP5#7 as the LRP5 antagonist and PD1-2 as the anti-PD-1 antibody. It is particularly preferred that these cancers are treated with LRP5#2 as the LRP5 antagonist and PD1-3 as the anti-PD-1 antibody. It is particularly preferred that these cancers are treated with LRP5#6 as the LRP5 antagonist and PD1-3 as the anti-PD-1 antibody. It is particularly preferred that these cancers are treated with LRP5#7 as the LRP5 antagonist and PD1-3 as the anti-PD-1 antibody.

In an alternative preferred embodiment, the combinations, compositions, kits, uses, methods and compounds for use according to the invention (including all embodiments) are used in the treatment of cancer patients suffering from any solid tumor that is refractory or resistant to checkpoint inhibitor therapies (e.g. to treatment with one or more immune checkpoint inhibitor and/or immuno modulators, e.g. one or more PD-1 antagonist(s) such as an anti-PD1 antibody). It is particularly preferred that these cancers are treated with LRP5#2 as the LRP5 antagonist and PD1-1 as the anti-PD-1 antibody. It is particularly preferred that these cancers are treated with LRP5#6 as the LRP5 antagonist and PD1-1 as the anti-PD-1 antibody. It is particularly preferred that these cancers are treated with LRP5#7 as the LRP5 antagonist and PD1-1 as the anti-PD-1 antibody. It is particularly preferred that these cancers are treated with LRP5#2 as the LRP5 antagonist and PD1-2 as the anti-PD-1 antibody. It is particularly preferred that these cancers are treated with LRP5#6 as the LRP5 antagonist and PD1-2 as the anti-PD-1 antibody. It is particularly preferred that these cancers are treated with LRP5#7 as the LRP5 antagonist and PD1-2 as the anti-PD-1 antibody. It is particularly preferred that these cancers are treated with LRP5#2 as the LRP5 antagonist and PD1-3 as the anti-PD-1 antibody. It is particularly preferred that these cancers are treated with LRP5#6 as the LRP5 antagonist and PD1-3 as the anti-PD-1 antibody. It is particularly preferred that these cancers are treated with LRP5#7 as the LRP5 antagonist and PD1-3 as the anti-PD-1 antibody. Examples for solid tumors are sufficiently known in the art. Similarly, the terms refractory or resistant are also known to the skilled person and are used herein in accordance with the definitions employed in the art.

Tumors which are refractory or resistant to checkpoint inhibitor therapies are also referred to herein as "immunotherapy-resistant tumors" or "immunotherapy-resistant non-T cell inflamed tumors". It has recently been found that in the microenvironment of many tumors a high expression of specific immune cells can be found. This is referred to in the art "T cell-inflamed phenotype" and it has been observed that this phenotype correlates with said tumors being amenable to treatment with multiple immunotherapies including therapeutic vaccines and checkpoint blocking antibodies, such as anti-PD-1 antibodies. On the other hand, certain tumors lack this expression of immune cells in their microenvironment. These tumors are referred to in the art as "non-T cell inflamed tumors" and they were found to lack clinical benefit to immunotherapy, particularly with anti-PD-1 antibodies. In accordance with the present invention, the latter type of tumors with active Wnt signalling are a preferred target for the claimed combination therapy. It is particularly preferred that these cancers are treated with LRP5#2 as the LRP5 antagonist and PD1-1 as the anti-PD-1 antibody. It is particularly preferred that these cancers are treated with LRP5#6 as the LRP5 antagonist and PD1-1 as the anti-PD-1 antibody. It is particularly preferred that these cancers are treated with LRP5#7 as the LRP5 antagonist and PD1-1 as the anti-PD-1 antibody. It is particularly preferred that these cancers are treated with LRP5#2 as the LRP5 antagonist and PD1-2 as the anti-PD-1 antibody. It is particularly preferred that these cancers are treated with LRP5#6 as the LRP5 antagonist and PD1-2 as the anti-PD-1 antibody. It is particularly preferred that these cancers are treated with LRP5#7 as the LRP5 antagonist and PD1-2 as the anti-PD-1 antibody. It is particularly preferred that these cancers are treated with LRP5#2 as the LRP5 antagonist and PD1-3 as the anti-PD-1 antibody. It is particularly preferred that these cancers are treated with LRP5#6 as the LRP5 antagonist and PD1-3 as the anti-PD-1 antibody. It is particularly preferred that these cancers are treated with LRP5#7 as the LRP5 antagonist and PD1-3 as the anti-PD-1 antibody.

The present invention is not to be limited in scope by the specific embodiments described herein. Various modifications of the invention in addition to those described herein may become apparent to those skilled in the art from the present disclosure. Such modifications are intended to fall within the scope of the appended claims.

All patent applications cited herein are hereby incorporated by reference in their entireties.

Example 1

Anti-Tumor Activity of the Exemplary LRP5 Antagonist in Combination with a Mouse Antibody to PD-1, in a Subcutaneous Syngeneic Mouse Model Derived from the Breast Cancer Cell Line EMT6 in Balb/c Mice The efficacy of the exemplary LRP5 antagonist was tested in a s.c. cell line derived syngeneic model of mouse breast cancer (EMT6) as single agent and in combination with a mouse antibody to PD-1.

BALB/cJBomTac mice were used in this study. $1\times10^6$ EMT6 breast cancer cells were injected per mouse to establish a tumor. Tumor volume was measured at least three times per week using a caliper. Treatment started when tumors had reached a median tumor volume of around 120 mm$^3$ and was terminated after 30 days.

Ten tumor-bearing animals were treated with the exemplary LRP5 antagonist intravenously (i.v.) twice a week and twice weekly i.p. with the anti-PD-1 antibody or a combination of both compounds. Ten animals were used in the vehicle/isotype control-treated group. Animals were euthanized at the end of the study for ethical reasons based on the tumor mass (tumor≥1.5 cm$^3$).

Cells

EMT6 cells were obtained from ATCC (catalog number ATCC® CRL2755™). A master cell bank (MCB) and a working cell bank (WCB) were established. Cells were cultured in Ti 75 tissue culture flasks at 37° C. and 5% $CO_2$. The medium used was Waymouth's MB 752/1 supplemented with 15% fetal calf serum (HyClone® Fetal Bovine Serum Characterized; Cat No SH30071.03; by Thermo Scientific), and 2 mM L-Glutamine (L-Glutamine 200 mM (100×); Ref 25030-024; by Gibco by Life Technologies). Cultures were split every two-three days with a ratio of 1:10/1:15.

Mice

Mice were 7-8 week-old BALB/cJBomTac purchased from Taconic, Denmark. After arrival at the animal facility, mice were allowed to adjust to ambient conditions for at least 5 days before they were used for experiments. They were housed in Macrolon® type III cages in groups of ten under standardized conditions at 21.5±1.5° C. and 55±10% humidity. Standardized irradiated diet (PROVIMI KLIBA) and autoclaved tap water were provided ad libitum. Microchips implanted subcutaneously under isoflurane anesthesia were used to identify each mouse. Cage cards showing the study number, the animal number, the compound and dose level, the administration route as well as the schedule remained with the animals throughout the study.

Administration of Test Compounds

LRP5 antagonist was suspended in histidine buffer pH 6.5 and administered i.v. an application volume of 10 mL/kg at the dose of 15 mg/kg twice weekly for the first two weeks. The PD-1 antibody was diluted in PBS and injected intraperitoneal with a volume of 10 mL/kg per mouse twice weekly at the dose of 10 mg/kg until the end of the study.

Monitoring Tumor Growth and Disease Progression

The tumor diameter was measured three times a week (Monday, Wednesday and Friday) with a caliper. The volume of each tumor [in mm$^3$] was calculated according to the formula "tumor volume=length*diameter2*π/6". To monitor side effects of treatment, mice were inspected daily for abnormalities and body weight was determined daily. Animals were sacrificed at the end of the study. Animals with necrotic tumors or tumor sizes exceeding 1500 mm$^3$ were sacrificed early during the studies for ethical reasons.

Results

Treatment of ETM6 tumors with the mouse antibody against PD-1 or LRP5 antagonist resulted in moderate tumor growth inhibition. Combination of the LRP5 antagonist with the PD-1 antibody resulted in significantly increased efficacy when compared with single agent administrations, inducing tumor regressions in 5 out of 10 mice when compared to the single treatments when tumor regression was observed in a lower number of mice (1 and 3 out of 10 mice treated with the single agent PD-1 antibody or LRP5 antagonist, respectively). The results demonstrating a synergistic effect of the combined administration compared to the single treatments are shown in FIG. 1. Furthermore, increased survival, reported in Table 5 as the interval in days from start of treatment to the time when the tumor volume reached at least 500 mm$^3$, was increased by the combination of the LRP5 antagonist with the PD-1 antibody when compared to the single treatments.

Table 5 shows the anti-tumor activity of the LRP5 antagonist as single agent and in combination with a mouse antibody to PD-1. The median refers to the interval (days) from start of treatment to the time when the tumor volume reached at least 500 mm$^3$.

TABLE 5

| Median (days) Time to ≥500 mm$^3$ tumor volume | LRP5 Start of treatment: median tumor volume 120 mm$^3$ |
|---|---|
| Isotype | 13 |
| Anti-PD-1 | 20 |
| LRP antagonist | 14 |
| Combination | Undefined (>30 days) |

The invention claimed is:

1. A method of treating a Wnt-ligand-mediated hyperproliferative disease, including cancer, comprising administering to a patient in need thereof a therapeutically effective amount of a LRP5 antagonist and a therapeutically effective amount of a PD-1 antibody, wherein the LRP5 antagonist comprises a polypeptide comprising the amino acid sequence of SEQ ID NO:59 and wherein the PD-1 antibody comprises heavy chain CDRs comprising the amino acid sequence of SEQ ID NO:13 (HCDR1), SEQ ID NO:14 (HCDR2) and SEQ ID NO:15 (HCDR3) and light chain CDRs comprising the amino acid sequence of SEQ ID NO:16 (LCDR1), SEQ ID NO:17 (LCDR2) and SEQ ID NO:18 (LCDR3).

2. The method of treating according to claim 1, wherein the anti-PD1 antibody is an antibody having a heavy chain variable domain comprising the amino acid sequence of SEQ ID NO:23 and a light chain variable domain comprising the amino acid sequence of SEQ ID NO:24.

3. The method of treating according to claim 1, wherein the PD-1 antibody is an antibody having a heavy chain comprising the amino acid sequence of SEQ ID NO:33 and a light chain comprising the amino acid sequence of SEQ ID NO: 34.

4. The method of treating according to claim 1, wherein the PD-1 antibody is administered simultaneously, concurrently, sequentially, successively or alternately with or separately from the LRP5 antagonist.

5. The method of treating according to claim 1, wherein the LRP5 antagonist and the PD-1 antibody are administered according to the following treatment regimen:

(i) a first treatment period, wherein the LRP5 antagonist and the PD-1 antibody are administered simultaneously or concurrently every three or four weeks; and
(ii) a second treatment period, wherein only the PD-1 antibody is administered and the LRP5 antagonist is not administered, wherein the PD-1 antibody is administered every three or four weeks.

6. The method of treating according to claim 5, wherein the first treatment period is 3 or 6 weeks when the LRP5 antagonist and PD-1 antibody are administered every three weeks or the first treatment period is 4 or 8 weeks when the LRP5 antagonist and PD-1 antibody are administered every four weeks.

7. The method of treating according to claim 5, wherein the administration is an intravenous administration.

8. The method of treating according to claim 1, wherein the hyperproliferative disease to be treated is a cancer selected from the group consisting of gastrointestinal cancer, melanoma tumours, bladder cancer and lung cancer, including NSCLC.

9. The method of treatment treating according to claim 8, wherein the gastrointestinal cancer is esophageal cancer, including gastroesophageal junction cancer, stomach (gastric) cancer, hepatocellular carcinoma, biliary tract cancer, including cholangiocarcinoma, gallbladder cancer or pancreatic cancer or colorectal cancer (CRC).

10. The method of treating according to claim 8, wherein the cancer is an immunotherapy-resistant tumour.

11. The method of treating according to claim 1, wherein the hyperproliferative disease to be treated is a solid immunotherapy-resistant tumour.

* * * * *

SEQUENCE LISTING

```
<160> NUMBER OF SEQ ID NOS: 62

<210> SEQ ID NO 1
<211> LENGTH: 10
<212> TYPE: PRT
<213> ORGANISM: Artificial Sequence
<220> FEATURE:
<223> OTHER INFORMATION: PD1-1HCDR1

<400> SEQUENCE: 1

Gly Phe Thr Phe Ser Ala Ser Ala Met Ser
1               5                   10

<210> SEQ ID NO 2
<211> LENGTH: 17
```

```
<212> TYPE: PRT
<213> ORGANISM: Artificial Sequence
<220> FEATURE:
<223> OTHER INFORMATION: PD1-1HCDR2

<400> SEQUENCE: 2

Tyr Ile Ser Gly Gly Gly Gly Asp Thr Tyr Tyr Ser Ser Val Lys
1               5                   10                  15
Gly

<210> SEQ ID NO 3
<211> LENGTH: 11
<212> TYPE: PRT
<213> ORGANISM: Artificial Sequence
<220> FEATURE:
<223> OTHER INFORMATION: PD1-1HCDR3

<400> SEQUENCE: 3

His Ser Asn Val Asn Tyr Tyr Ala Met Asp Tyr
1               5                   10

<210> SEQ ID NO 4
<211> LENGTH: 15
<212> TYPE: PRT
<213> ORGANISM: Artificial Sequence
<220> FEATURE:
<223> OTHER INFORMATION: PD1-1LCDR1

<400> SEQUENCE: 4

Arg Ala Ser Glu Asn Ile Asp Thr Ser Gly Ile Ser Phe Met Asn
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: PD1-1LCDR2

<400> SEQUENCE: 5

Val Ala Ser Asn Gln Gly Ser
1               5

<210> SEQ ID NO 6
<211> LENGTH: 9
<212> TYPE: PRT
<213> ORGANISM: Artificial Sequence
<220> FEATURE:
<223> OTHER INFORMATION: PD1-1LCDR3

<400> SEQUENCE: 6

Gln Gln Ser Lys Glu Val Pro Trp Thr
1               5

<210> SEQ ID NO 7
<211> LENGTH: 10
<212> TYPE: PRT
<213> ORGANISM: Artificial Sequence
<220> FEATURE:
<223> OTHER INFORMATION: PD1-2HCDR1

<400> SEQUENCE: 7

Gly Phe Thr Phe Ser Ala Ser Ala Met Ser
1               5                   10

<210> SEQ ID NO 8
```

```
<211> LENGTH: 17
<212> TYPE: PRT
<213> ORGANISM: Artificial Sequence
<220> FEATURE:
<223> OTHER INFORMATION: PD1-2HCDR2

<400> SEQUENCE: 8

Tyr Ile Ser Gly Gly Gly Gly Asp Thr Tyr Tyr Ser Ser Ser Val Lys
1               5                   10                  15
Gly

<210> SEQ ID NO 9
<211> LENGTH: 11
<212> TYPE: PRT
<213> ORGANISM: Artificial Sequence
<220> FEATURE:
<223> OTHER INFORMATION: PD1-2HCDR3

<400> SEQUENCE: 9

His Ser Asn Pro Asn Tyr Tyr Ala Met Asp Tyr
1               5                   10

<210> SEQ ID NO 10
<211> LENGTH: 15
<212> TYPE: PRT
<213> ORGANISM: Artificial Sequence
<220> FEATURE:
<223> OTHER INFORMATION: PD1-2LCDR1

<400> SEQUENCE: 10

Arg Ala Ser Glu Asn Ile Asp Thr Ser Gly Ile Ser Phe Met Asn
1               5                   10                  15

<210> SEQ ID NO 11
<211> LENGTH: 7
<212> TYPE: PRT
<213> ORGANISM: Artificial Sequence
<220> FEATURE:
<223> OTHER INFORMATION: PD1-2LCDR2

<400> SEQUENCE: 11

Val Ala Ser Asn Gln Gly Ser
1               5

<210> SEQ ID NO 12
<211> LENGTH: 9
<212> TYPE: PRT
<213> ORGANISM: Artificial Sequence
<220> FEATURE:
<223> OTHER INFORMATION: PD1-2LCDR3

<400> SEQUENCE: 12

Gln Gln Ser Lys Glu Val Pro Trp Thr
1               5

<210> SEQ ID NO 13
<211> LENGTH: 10
<212> TYPE: PRT
<213> ORGANISM: Artificial Sequence
<220> FEATURE:
<223> OTHER INFORMATION: PD1-3HCDR1

<400> SEQUENCE: 13

Gly Phe Thr Phe Ser Lys Ser Ala Met Ser
1               5                   10
```

```
<210> SEQ ID NO 14
<211> LENGTH: 17
<212> TYPE: PRT
<213> ORGANISM: Artificial Sequence
<220> FEATURE:
<223> OTHER INFORMATION: PD1-3HCDR2

<400> SEQUENCE: 14

Tyr Ile Ser Gly Gly Gly Gly Asp Thr Tyr Tyr Ser Ser Ser Val Lys
1               5                   10                  15

Gly

<210> SEQ ID NO 15
<211> LENGTH: 11
<212> TYPE: PRT
<213> ORGANISM: Artificial Sequence
<220> FEATURE:
<223> OTHER INFORMATION: PD1-3HCDR3

<400> SEQUENCE: 15

His Ser Asn Val Asn Tyr Tyr Ala Met Asp Tyr
1               5                   10

<210> SEQ ID NO 16
<211> LENGTH: 15
<212> TYPE: PRT
<213> ORGANISM: Artificial Sequence
<220> FEATURE:
<223> OTHER INFORMATION: PD1-3LCDR1

<400> SEQUENCE: 16

Arg Ala Ser Glu Asn Ile Asp Val Ser Gly Ile Ser Phe Met Asn
1               5                   10                  15

<210> SEQ ID NO 17
<211> LENGTH: 7
<212> TYPE: PRT
<213> ORGANISM: Artificial Sequence
<220> FEATURE:
<223> OTHER INFORMATION: PD1-3LCDR2

<400> SEQUENCE: 17

Val Ala Ser Asn Gln Gly Ser
1               5

<210> SEQ ID NO 18
<211> LENGTH: 9
<212> TYPE: PRT
<213> ORGANISM: Artificial Sequence
<220> FEATURE:
<223> OTHER INFORMATION: PD1-3LCDR3

<400> SEQUENCE: 18

Gln Gln Ser Lys Glu Val Pro Trp Thr
1               5

<210> SEQ ID NO 19
<211> LENGTH: 120
<212> TYPE: PRT
<213> ORGANISM: Artificial Sequence
<220> FEATURE:
<223> OTHER INFORMATION: PD1VH1

<400> SEQUENCE: 19

Glu Val Met Leu Val Glu Ser Gly Gly Gly Leu Val Gln Pro Gly Gly
1               5                   10                  15
```

Ser Leu Arg Leu Ser Cys Thr Ala Ser Gly Phe Thr Phe Ser Ala Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser
        115                 120

<210> SEQ ID NO 20
<211> LENGTH: 111
<212> TYPE: PRT
<213> ORGANISM: Artificial Sequence
<220> FEATURE:
<223> OTHER INFORMATION: PD1VL1

<400> SEQUENCE: 20

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Thr Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys
            100                 105                 110

<210> SEQ ID NO 21
<211> LENGTH: 120
<212> TYPE: PRT
<213> ORGANISM: Artificial Sequence
<220> FEATURE:
<223> OTHER INFORMATION: PD1VH2

<400> SEQUENCE: 21

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ala Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

```
Ala Arg His Ser Asn Pro Asn Tyr Tyr Ala Met Asp Tyr Trp Gly Gln
            100                 105                 110

Gly Thr Leu Val Thr Val Ser Ser
        115                 120

<210> SEQ ID NO 22
<211> LENGTH: 111
<212> TYPE: PRT
<213> ORGANISM: Artificial Sequence
<220> FEATURE:
<223> OTHER INFORMATION: PD1VL2

<400> SEQUENCE: 22

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Thr Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys
            100                 105                 110

<210> SEQ ID NO 23
<211> LENGTH: 120
<212> TYPE: PRT
<213> ORGANISM: Artificial Sequence
<220> FEATURE:
<223> OTHER INFORMATION: PD1VH3

<400> SEQUENCE: 23

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser
        115                 120

<210> SEQ ID NO 24
<211> LENGTH: 111
<212> TYPE: PRT
<213> ORGANISM: Artificial Sequence
<220> FEATURE:
<223> OTHER INFORMATION: PD1VL3
```

<400> SEQUENCE: 24

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys
            100                 105                 110

<210> SEQ ID NO 25
<211> LENGTH: 120
<212> TYPE: PRT
<213> ORGANISM: Artificial Sequence
<220> FEATURE:
<223> OTHER INFORMATION: PD1VH4

<400> SEQUENCE: 25

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser
        115                 120

<210> SEQ ID NO 26
<211> LENGTH: 111
<212> TYPE: PRT
<213> ORGANISM: Artificial Sequence
<220> FEATURE:
<223> OTHER INFORMATION: PD1VL4

<400> SEQUENCE: 26

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

```
Arg Phe Ser Gly Ser Gly Ser Gly Thr Asp Phe Thr Leu Thr Ile Ser
 65                  70                  75                  80

Arg Leu Glu Pro Glu Asp Phe Ala Val Tyr Tyr Cys Gln Gln Ser Lys
                 85                  90                  95

Glu Val Pro Trp Thr Phe Gly Gln Gly Thr Lys Leu Glu Ile Lys
            100                 105                 110

<210> SEQ ID NO 27
<211> LENGTH: 120
<212> TYPE: PRT
<213> ORGANISM: Artificial Sequence
<220> FEATURE:
<223> OTHER INFORMATION: PD1VH5

<400> SEQUENCE: 27

Glu Val Met Leu Val Glu Ser Gly Gly Gly Leu Val Gln Pro Gly Gly
 1               5                   10                  15

Ser Leu Arg Leu Ser Cys Thr Ala Ser Gly Phe Thr Phe Ser Lys Ser
             20                  25                  30

Ala Met Ser Trp Val Arg Gln Ala Pro Gly Lys Gly Leu Glu Trp Val
         35                  40                  45

Ala Tyr Ile Ser Gly Gly Gly Asp Thr Tyr Tyr Ser Ser Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg His Ser Asn Val Asn Tyr Tyr Ala Met Asp Tyr Trp Gly Gln
            100                 105                 110

Gly Thr Leu Val Thr Val Ser Ser
            115                 120

<210> SEQ ID NO 28
<211> LENGTH: 111
<212> TYPE: PRT
<213> ORGANISM: Artificial Sequence
<220> FEATURE:
<223> OTHER INFORMATION: PD1VL5

<400> SEQUENCE: 28

Glu Ile Val Leu Thr Gln Ser Pro Ala Thr Leu Ser Leu Ser Pro Gly
 1               5                   10                  15

Glu Arg Ala Thr Met Ser Cys Arg Ala Ser Glu Asn Ile Asp Val Ser
             20                  25                  30

Gly Ile Ser Phe Met Asn Trp Tyr Gln Gln Lys Pro Gly Gln Ala Pro
         35                  40                  45

Lys Leu Leu Ile Tyr Val Ala Ser Asn Gln Gly Ser Gly Ile Pro Ala
     50                  55                  60

Arg Phe Ser Gly Ser Gly Ser Gly Thr Asp Phe Thr Leu Thr Ile Ser
 65                  70                  75                  80

Arg Leu Glu Pro Glu Asp Phe Ala Val Tyr Tyr Cys Gln Gln Ser Lys
                 85                  90                  95

Glu Val Pro Trp Thr Phe Gly Gln Gly Thr Lys Leu Glu Ile Lys
            100                 105                 110

<210> SEQ ID NO 29
<211> LENGTH: 446
<212> TYPE: PRT
```

<213> ORGANISM: Artificial Sequence
<220> FEATURE:
<223> OTHER INFORMATION: PD1HC1

<400> SEQUENCE: 29

```
Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ala Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
```

```
385                 390                 395                 400
Asp Gly Ser Phe Phe Leu Tyr Ser Arg Leu Thr Val Asp Lys Ser Arg
                    405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly
            435                 440                 445
```

<210> SEQ ID NO 30
<211> LENGTH: 218
<212> TYPE: PRT
<213> ORGANISM: Artificial Sequence
<220> FEATURE:
<223> OTHER INFORMATION: PD1LC1

<400> SEQUENCE: 30

```
Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Thr Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 31
<211> LENGTH: 446
<212> TYPE: PRT
<213> ORGANISM: Artificial Sequence
<220> FEATURE:
<223> OTHER INFORMATION: PD1HC2

<400> SEQUENCE: 31

```
Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ala Ser
            20                  25                  30
```

Ala Met Ser Trp Val Arg Gln Ala Pro Gly Lys Gly Leu Glu Trp Val
         35                  40                  45

Ala Tyr Ile Ser Gly Gly Gly Asp Thr Tyr Tyr Ser Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg His Ser Asn Pro Asn Tyr Tyr Ala Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

```
<210> SEQ ID NO 32
<211> LENGTH: 218
<212> TYPE: PRT
<213> ORGANISM: Artificial Sequence
<220> FEATURE:
<223> OTHER INFORMATION: PD1LC2

<400> SEQUENCE: 32

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Thr Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 33
<211> LENGTH: 446
<212> TYPE: PRT
<213> ORGANISM: Artificial Sequence
<220> FEATURE:
<223> OTHER INFORMATION: PD1HC3

<400> SEQUENCE: 33

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

```
Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 34
<211> LENGTH: 218
<212> TYPE: PRT
<213> ORGANISM: Artificial Sequence
<220> FEATURE:
<223> OTHER INFORMATION: PD1LC3

<400> SEQUENCE: 34

Glu Ile Val Leu Thr Gln Ser Pro Ala Thr Leu Ser Leu Ser Pro Gly
1               5                   10                  15
```

Glu Arg Ala Thr Met Ser Cys Arg Ala Ser Glu Asn Ile Asp Val Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215

<210> SEQ ID NO 35
<211> LENGTH: 446
<212> TYPE: PRT
<213> ORGANISM: Artificial Sequence
<220> FEATURE:
<223> OTHER INFORMATION: PD1HC4

<400> SEQUENCE: 35

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

```
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Leu Gly
        435                 440                 445

<210> SEQ ID NO 36
<211> LENGTH: 218
<212> TYPE: PRT
<213> ORGANISM: Artificial Sequence
<220> FEATURE:
<223> OTHER INFORMATION: PD1LC4

<400> SEQUENCE: 36

Glu Ile Val Leu Thr Gln Ser Pro Ala Thr Leu Ser Leu Ser Pro Gly
1               5                   10                  15
Glu Arg Ala Thr Met Ser Cys Arg Ala Ser Glu Asn Ile Asp Val Ser
            20                  25                  30
Gly Ile Ser Phe Met Asn Trp Tyr Gln Gln Lys Pro Gly Gln Ala Pro
        35                  40                  45
Lys Leu Leu Ile Tyr Val Ala Ser Asn Gln Gly Ser Gly Ile Pro Ala
    50                  55                  60
Arg Phe Ser Gly Ser Gly Ser Gly Thr Asp Phe Thr Leu Thr Ile Ser
65                  70                  75                  80
```

```
Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 37
<211> LENGTH: 446
<212> TYPE: PRT
<213> ORGANISM: Artificial Sequence
<220> FEATURE:
<223> OTHER INFORMATION: PD1HC5

<400> SEQUENCE: 37

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220
```

```
Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
            435                 440                 445

<210> SEQ ID NO 38
<211> LENGTH: 218
<212> TYPE: PRT
<213> ORGANISM: Artificial Sequence
<220> FEATURE:
<223> OTHER INFORMATION: PD1LC5

<400> SEQUENCE: 38

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
            85                  90                  95

Glu Val Pro Trp Thr Phe Gly Gln Gly Thr Lys Leu Glu Ile Lys Arg
        100                 105                 110

Thr Val Ala Ala Pro Ser Val Phe Ile Phe Pro Pro Ser Asp Glu Gln
    115                 120                 125

Leu Lys Ser Gly Thr Ala Ser Val Val Cys Leu Leu Asn Asn Phe Tyr
130                 135                 140
```

```
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 39
<211> LENGTH: 5
<212> TYPE: PRT
<213> ORGANISM: Artificial Sequence
<220> FEATURE:
<223> OTHER INFORMATION: motif for B7-1 and B7-2 binding

<400> SEQUENCE: 39

Met Tyr Pro Pro Tyr
1               5

<210> SEQ ID NO 40
<211> LENGTH: 5
<212> TYPE: PRT
<213> ORGANISM: Artificial Sequence
<220> FEATURE:
<223> OTHER INFORMATION: F0129097A08 CDR1

<400> SEQUENCE: 40

Thr Tyr Val Met Gly
1               5

<210> SEQ ID NO 41
<211> LENGTH: 17
<212> TYPE: PRT
<213> ORGANISM: Artificial Sequence
<220> FEATURE:
<223> OTHER INFORMATION: F0129097A08 CDR2

<400> SEQUENCE: 41

Ala Ile Ser Trp Ser Gly Gly Ser Thr Tyr Tyr Ala Asp Ser Val Lys
1               5                   10                  15

Gly

<210> SEQ ID NO 42
<211> LENGTH: 18
<212> TYPE: PRT
<213> ORGANISM: Artificial Sequence
<220> FEATURE:
<223> OTHER INFORMATION: F0129097A08 CDR3

<400> SEQUENCE: 42

Ser Arg Gly Thr Ser Thr Pro Ser Arg Ala Ser Gly Val Ser Arg Tyr
1               5                   10                  15

Asp Tyr

<210> SEQ ID NO 43
<211> LENGTH: 5
<212> TYPE: PRT
<213> ORGANISM: Artificial Sequence
<220> FEATURE:
<223> OTHER INFORMATION: F0129093A02 CDR1
```

```
<400> SEQUENCE: 43

Arg Tyr Ala Val Ala
1               5

<210> SEQ ID NO 44
<211> LENGTH: 17
<212> TYPE: PRT
<213> ORGANISM: Artificial Sequence
<220> FEATURE:
<223> OTHER INFORMATION: F0129093A02 CDR2

<400> SEQUENCE: 44

Ala Ile Thr Trp Ser Ser Gly Arg Ile Asp Tyr Ala Asp Ser Val Lys
1               5                   10                  15

Gly

<210> SEQ ID NO 45
<211> LENGTH: 20
<212> TYPE: PRT
<213> ORGANISM: Artificial Sequence
<220> FEATURE:
<223> OTHER INFORMATION: F0129093A02 CDR3

<400> SEQUENCE: 45

Asp Arg Arg Pro Arg Ser Thr Gly Arg Ser Gly Thr Gly Ser Pro Ser
1               5                   10                  15

Thr Tyr Asp Tyr
            20

<210> SEQ ID NO 46
<211> LENGTH: 5
<212> TYPE: PRT
<213> ORGANISM: Artificial Sequence
<220> FEATURE:
<223> OTHER INFORMATION: F012904 6C10(E1A,N32G) CDR1

<400> SEQUENCE: 46

Ile Gly Ala Met Gly
1               5

<210> SEQ ID NO 47
<211> LENGTH: 16
<212> TYPE: PRT
<213> ORGANISM: Artificial Sequence
<220> FEATURE:
<223> OTHER INFORMATION: F012904 6C10(E1A,N32G) CDR2 / F012904 6C10 CDR2

<400> SEQUENCE: 47

Ala Val Ser Ser Gly Gly Ser Thr Tyr Tyr Val Asp Ser Val Lys Gly
1               5                   10                  15

<210> SEQ ID NO 48
<211> LENGTH: 12
<212> TYPE: PRT
<213> ORGANISM: Artificial Sequence
<220> FEATURE:
<223> OTHER INFORMATION: F012904 6C10(E1A,N32G) CDR3 / F012904 6C10 CDR3

<400> SEQUENCE: 48

Glu Thr Gly Pro Tyr Gly Pro Pro Lys Arg Asp Tyr
1               5                   10

<210> SEQ ID NO 49
<211> LENGTH: 5
<212> TYPE: PRT
```

<213> ORGANISM: Artificial Sequence
<220> FEATURE:
<223> OTHER INFORMATION: F012904 6C10 CDR1

<400> SEQUENCE: 49

Ile Asn Ala Met Gly
1               5

<210> SEQ ID NO 50
<211> LENGTH: 127
<212> TYPE: PRT
<213> ORGANISM: Artificial Sequence
<220> FEATURE:
<223> OTHER INFORMATION: F0129097A08(E1A,V23A) VHH

<400> SEQUENCE: 50

Ala Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Thr Tyr
            20                  25                  30

Val Met Gly Trp Phe Arg Gln Ala Pro Gly Lys Glu Arg Glu Phe Val
        35                  40                  45

Ala Ala Ile Ser Trp Ser Gly Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Ser Arg Gly Thr Ser Thr Pro Ser Arg Ala Ser Gly Val Ser
            100                 105                 110

Arg Tyr Asp Tyr Trp Gly Gln Gly Thr Leu Val Thr Val Ser Ser
        115                 120                 125

<210> SEQ ID NO 51
<211> LENGTH: 130
<212> TYPE: PRT
<213> ORGANISM: Artificial Sequence
<220> FEATURE:
<223> OTHER INFORMATION: F0129093A02 VHH

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Arg Tyr
            20                  25                  30

Ala Val Ala Trp Phe Arg Gln Ala Pro Gly Lys Glu Arg Glu Phe Val
        35                  40                  45

Ala Ala Ile Thr Trp Ser Gly Arg Ile Asp Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Asp Arg Arg Pro Arg Ser Thr Gly Arg Ser Gly Thr Gly Ser
            100                 105                 110

Pro Ser Thr Tyr Asp Tyr Trp Gly Gln Gly Thr Leu Val Thr Val Ser
        115                 120                 125

Ser Ala
    130

<210> SEQ ID NO 52
<211> LENGTH: 120
<212> TYPE: PRT
<213> ORGANISM: Artificial Sequence
<220> FEATURE:
<223> OTHER INFORMATION: F0129046C10(E1A,N32G) VHH

<400> SEQUENCE: 52

Ala Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Arg Ile Gly
            20                  25                  30

Ala Met Gly Trp Tyr Arg Gln Ala Pro Gly Lys Gln Arg Glu Leu Val
        35                  40                  45

Ala Ala Val Ser Ser Gly Gly Ser Thr Tyr Tyr Val Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Arg Glu Thr Gly Pro Tyr Gly Pro Pro Lys Arg Asp Tyr Trp Gly Gln
            100                 105                 110

Gly Thr Leu Val Thr Val Ser Ser
        115                 120

<210> SEQ ID NO 53
<211> LENGTH: 120
<212> TYPE: PRT
<213> ORGANISM: Artificial Sequence
<220> FEATURE:
<223> OTHER INFORMATION: F0129046C10 VHH

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Arg Ile Asn
            20                  25                  30

Ala Met Gly Trp Tyr Arg Gln Ala Pro Gly Lys Gln Arg Glu Leu Val
        35                  40                  45

Ala Ala Val Ser Ser Gly Gly Ser Thr Tyr Tyr Val Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Arg Glu Thr Gly Pro Tyr Gly Pro Pro Lys Arg Asp Tyr Trp Gly Gln
            100                 105                 110

Gly Thr Leu Val Thr Val Ser Ser
        115                 120

<210> SEQ ID NO 54
<211> LENGTH: 5
<212> TYPE: PRT
<213> ORGANISM: Artificial Sequence
<220> FEATURE:
<223> OTHER INFORMATION: Alb11 domain CDR1

<400> SEQUENCE: 54

```
Ser Phe Gly Met Ser
1               5

<210> SEQ ID NO 55
<211> LENGTH: 17
<212> TYPE: PRT
<213> ORGANISM: Artificial Sequence
<220> FEATURE:
<223> OTHER INFORMATION: Alb11 domain CDR2

<400> SEQUENCE: 55

Ser Ile Ser Gly Ser Gly Ser Asp Thr Leu Tyr Ala Asp Ser Val Lys
1               5                   10                  15

Gly

<210> SEQ ID NO 56
<211> LENGTH: 6
<212> TYPE: PRT
<213> ORGANISM: Artificial Sequence
<220> FEATURE:
<223> OTHER INFORMATION: Alb11 domain CDR3

<400> SEQUENCE: 56

Gly Gly Ser Leu Ser Arg
1               5

<210> SEQ ID NO 57
<211> LENGTH: 432
<212> TYPE: PRT
<213> ORGANISM: Artificial Sequence
<220> FEATURE:
<223> OTHER INFORMATION: Polypeptide capable of specifically binding to
      LRP5 (1)

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Val Ala Ser Gly Arg Thr Phe Ser Thr Tyr
            20                  25                  30

Val Met Gly Trp Phe Arg Gln Ala Pro Gly Lys Glu Arg Glu Phe Val
        35                  40                  45

Ala Ala Ile Ser Trp Ser Gly Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Ser Arg Gly Thr Ser Thr Pro Ser Arg Ala Ser Gly Val Ser
            100                 105                 110

Arg Tyr Asp Tyr Trp Gly Gln Gly Thr Leu Val Thr Val Ser Ser Gly
        115                 120                 125

Gly Gly Gly Ser Gly Gly Gly Ser Gly Gly Gly Gly Ser Gly Gly Gly
    130                 135                 140

Gly Gly Ser Gly Gly Gly Gly Ser Gly Gly Gly Gly Ser Gly Gly Gly
145                 150                 155                 160

Gly Ser Glu Val Gln Leu Val Glu Ser Gly Gly Gly Leu Val Gln Pro
                165                 170                 175

Gly Asn Ser Leu Arg Leu Ser Cys Ala Ala Ser Gly Phe Thr Phe Ser
            180                 185                 190

Ser Phe Gly Met Ser Trp Val Arg Gln Ala Pro Gly Lys Gly Leu Glu
```

```
                195                 200                 205
Trp Val Ser Ser Ile Ser Gly Ser Gly Ser Asp Thr Leu Tyr Ala Asp
    210                 215                 220

Ser Val Lys Gly Arg Phe Thr Ile Ser Arg Asp Asn Ala Lys Thr Thr
225                 230                 235                 240

Leu Tyr Leu Gln Met Asn Ser Leu Arg Pro Glu Asp Thr Ala Val Tyr
                245                 250                 255

Tyr Cys Thr Ile Gly Gly Ser Leu Ser Arg Ser Ser Gln Gly Thr Leu
            260                 265                 270

Val Thr Val Ser Ser Gly Gly Gly Ser Gly Gly Gly Ser Gly
        275                 280                 285

Gly Gly Gly Ser Gly Gly Gly Ser Gly Gly Gly Ser Gly Gly
    290                 295                 300

Gly Gly Ser Gly Gly Gly Ser Glu Val Gln Leu Val Glu Ser Gly
305                 310                 315                 320

Gly Gly Leu Val Gln Pro Gly Gly Ser Leu Arg Leu Ser Cys Ala Ala
                325                 330                 335

Ser Gly Ser Ile Phe Arg Ile Asn Ala Met Gly Trp Tyr Arg Gln Ala
            340                 345                 350

Pro Gly Lys Gln Arg Glu Leu Val Ala Ala Val Ser Ser Gly Gly Ser
        355                 360                 365

Thr Tyr Tyr Val Asp Ser Val Lys Gly Arg Phe Thr Ile Ser Arg Asp
    370                 375                 380

Asn Ser Lys Asn Thr Val Tyr Leu Gln Met Asn Ser Leu Arg Pro Glu
385                 390                 395                 400

Asp Thr Ala Val Tyr Tyr Cys Asn Arg Glu Thr Gly Pro Tyr Gly Pro
                405                 410                 415

Pro Lys Arg Asp Tyr Trp Gly Gln Gly Thr Leu Val Thr Val Ser Ser
            420                 425                 430

<210> SEQ ID NO 58
<211> LENGTH: 435
<212> TYPE: PRT
<213> ORGANISM: Artificial Sequence
<220> FEATURE:
<223> OTHER INFORMATION: Polypeptide capable of specifically binding to
      LRP5 (2)

<400> SEQUENCE: 58

Ala Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Arg Ile Gly
            20                  25                  30

Ala Met Gly Trp Tyr Arg Gln Ala Pro Gly Lys Gln Arg Glu Leu Val
        35                  40                  45

Ala Ala Val Ser Ser Gly Gly Ser Thr Tyr Tyr Val Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Arg Glu Thr Gly Pro Tyr Gly Pro Pro Lys Arg Asp Tyr Trp Gly Gln
            100                 105                 110

Gly Thr Leu Val Thr Val Ser Ser Gly Gly Gly Ser Gly Gly Gly
        115                 120                 125
```

Gly Ser Gly Gly Gly Ser Gly Gly Gly Ser Gly Gly Gly
        130                 135                 140

Ser Gly Gly Gly Ser Gly Gly Gly Ser Glu Val Gln Leu Val
145                 150                 155                 160

Glu Ser Gly Gly Gly Leu Val Gln Pro Gly Asn Ser Leu Arg Leu Ser
                165                 170                 175

Cys Ala Ala Ser Gly Phe Thr Phe Ser Ser Phe Gly Met Ser Trp Val
                180                 185                 190

Arg Gln Ala Pro Gly Lys Gly Leu Glu Trp Val Ser Ser Ile Ser Gly
            195                 200                 205

Ser Gly Ser Asp Thr Leu Tyr Ala Asp Ser Val Lys Gly Arg Phe Thr
210                 215                 220

Ile Ser Arg Asp Asn Ala Lys Thr Thr Leu Tyr Leu Gln Met Asn Ser
225                 230                 235                 240

Leu Arg Pro Glu Asp Thr Ala Val Tyr Tyr Cys Thr Ile Gly Gly Ser
                245                 250                 255

Leu Ser Arg Ser Ser Gln Gly Thr Leu Val Thr Val Ser Ser Gly Gly
            260                 265                 270

Gly Gly Ser Gly Gly Gly Gly Ser Gly Gly Gly Gly Ser Gly Gly Gly
            275                 280                 285

Gly Ser Gly Gly Gly Gly Ser Gly Gly Gly Gly Ser Gly Gly Gly Gly
    290                 295                 300

Ser Glu Val Gln Leu Val Glu Ser Gly Gly Gly Leu Val Gln Pro Gly
305                 310                 315                 320

Gly Ser Leu Arg Leu Ser Cys Ala Ala Ser Gly Leu Thr Phe Ser Arg
                325                 330                 335

Tyr Ala Val Ala Trp Phe Arg Gln Ala Pro Gly Lys Glu Arg Glu Phe
            340                 345                 350

Val Ala Ala Ile Thr Trp Ser Ser Gly Arg Ile Asp Tyr Ala Asp Ser
                355                 360                 365

Val Lys Gly Arg Phe Thr Ile Ser Arg Asp Asn Ser Lys Asn Thr Val
370                 375                 380

Tyr Leu Gln Met Asn Ser Leu Arg Pro Glu Asp Thr Ala Val Tyr Tyr
385                 390                 395                 400

Cys Ala Ala Asp Arg Arg Pro Arg Ser Thr Gly Arg Ser Gly Thr Gly
                405                 410                 415

Ser Pro Ser Thr Tyr Asp Tyr Trp Gly Gln Gly Thr Leu Val Thr Val
            420                 425                 430

Ser Ser Ala
    435

<210> SEQ ID NO 59
<211> LENGTH: 433
<212> TYPE: PRT
<213> ORGANISM: Artificial Sequence
<220> FEATURE:
<223> OTHER INFORMATION: Polypeptide capable of specifically binding to
      LRP5 (3)

<400> SEQUENCE: 59

Ala Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Thr Tyr
            20                  25                  30

Val Met Gly Trp Phe Arg Gln Ala Pro Gly Lys Glu Arg Glu Phe Val
        35                  40                  45

```
Ala Ala Ile Ser Trp Ser Gly Ser Thr Tyr Tyr Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Val Tyr Tyr Cys
                 85                  90                  95

Ala Ala Ser Arg Gly Thr Ser Thr Pro Ser Arg Ala Ser Gly Val Ser
            100                 105                 110

Arg Tyr Asp Tyr Trp Gly Gln Gly Thr Leu Val Thr Val Ser Ser Gly
            115                 120                 125

Gly Gly Gly Ser Gly Gly Gly Ser Gly Gly Gly Ser Gly Gly Gly Gly
130                 135                 140

Gly Gly Ser Gly Gly Gly Ser Gly Gly Gly Ser Gly Gly Gly Ser Gly
145                 150                 155                 160

Gly Ser Glu Val Gln Leu Val Glu Ser Gly Gly Gly Leu Val Gln Pro
            165                 170                 175

Gly Asn Ser Leu Arg Leu Ser Cys Ala Ala Ser Gly Phe Thr Phe Ser
            180                 185                 190

Ser Phe Gly Met Ser Trp Val Arg Gln Ala Pro Gly Lys Gly Leu Glu
            195                 200                 205

Trp Val Ser Ser Ile Ser Gly Ser Gly Ser Asp Thr Leu Tyr Ala Asp
210                 215                 220

Ser Val Lys Gly Arg Phe Thr Ile Ser Arg Asp Asn Ala Lys Thr Thr
225                 230                 235                 240

Leu Tyr Leu Gln Met Asn Ser Leu Arg Pro Glu Asp Thr Ala Val Tyr
                245                 250                 255

Tyr Cys Thr Ile Gly Gly Ser Leu Ser Arg Ser Ser Gln Gly Thr Leu
            260                 265                 270

Val Thr Val Ser Ser Gly Gly Gly Ser Gly Gly Gly Gly Ser Gly
            275                 280                 285

Gly Gly Gly Ser Gly Gly Gly Ser Gly Gly Gly Gly Ser Gly Gly
290                 295                 300

Gly Gly Ser Gly Gly Gly Ser Glu Val Gln Leu Val Glu Ser Gly
305                 310                 315                 320

Gly Gly Leu Val Gln Pro Gly Gly Ser Leu Arg Leu Ser Cys Ala Ala
            325                 330                 335

Ser Gly Ser Ile Phe Arg Ile Gly Ala Met Gly Trp Tyr Arg Gln Ala
            340                 345                 350

Pro Gly Lys Gln Arg Glu Leu Val Ala Ala Val Ser Ser Gly Gly Ser
            355                 360                 365

Thr Tyr Tyr Val Asp Ser Val Lys Gly Arg Phe Thr Ile Ser Arg Asp
            370                 375                 380

Asn Ser Lys Asn Thr Val Tyr Leu Gln Met Asn Ser Leu Arg Pro Glu
385                 390                 395                 400

Asp Thr Ala Val Tyr Tyr Cys Asn Arg Glu Thr Gly Pro Tyr Gly Pro
                405                 410                 415

Pro Lys Arg Asp Tyr Trp Gly Gln Gly Thr Leu Val Thr Val Ser Ser
            420                 425                 430

Ala
```

<210> SEQ ID NO 60
<211> LENGTH: 115
<212> TYPE: PRT

```
<213> ORGANISM: Artificial Sequence
<220> FEATURE:
<223> OTHER INFORMATION: Alb11 VHH

<400> SEQUENCE: 60

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 61
<211> LENGTH: 121
<212> TYPE: PRT
<213> ORGANISM: Artificial Sequence
<220> FEATURE:
<223> OTHER INFORMATION: F0129046C10(N32G) VHH

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Arg Ile Gly
            20                  25                  30

Ala Met Gly Trp Tyr Arg Gln Ala Pro Gly Lys Gln Arg Glu Leu Val
        35                  40                  45

Ala Ala Val Ser Ser Gly Gly Ser Thr Tyr Tyr Val Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Arg Glu Thr Gly Pro Tyr Gly Pro Pro Lys Arg Asp Tyr Trp Gly Gln
            100                 105                 110

Gly Thr Leu Val Thr Val Ser Ser Ala
        115                 120

<210> SEQ ID NO 62
<211> LENGTH: 127
<212> TYPE: PRT
<213> ORGANISM: Artificial Sequence
<220> FEATURE:
<223> OTHER INFORMATION: F0129097A08 VHH

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Val Ala Ser Gly Arg Thr Phe Ser Thr Tyr
            20                  25                  30
```

```
Val Met Gly Trp Phe Arg Gln Ala Pro Gly Lys Glu Arg Glu Phe Val
        35              40              45
Ala Ala Ile Ser Trp Ser Gly Gly Ser Thr Tyr Tyr Ala Asp Ser Val
    50              55              60
Lys Gly Arg Phe Thr Ile Ser Arg Asp Asn Ser Lys Asn Thr Val Tyr
65              70              75              80
Leu Gln Met Asn Ser Leu Arg Pro Glu Asp Thr Ala Val Tyr Tyr Cys
            85              90              95
Ala Ala Ser Arg Gly Thr Ser Thr Pro Ser Arg Ala Ser Gly Val Ser
            100             105             110
Arg Tyr Asp Tyr Trp Gly Gln Gly Thr Leu Val Thr Val Ser Ser
        115             120             125
```